US010987208B2

(12) United States Patent
Schaefer et al.

(10) Patent No.: US 10,987,208 B2
(45) Date of Patent: Apr. 27, 2021

(54) DEVICES AND METHODS FOR TREATING AN ANEURYSM

(71) Applicant: MERLIN MD PTE LTD., Singapore (SG)

(72) Inventors: Dean Schaefer, Singapore (SG); Felizardo Gratila Batiao, Singapore (SG); Siew Yin Lee, Singapore (SG); J. Christopher Flaherty, Auburndale, FL (US); Dhirendra Singh, Singapore (SG)

(73) Assignee: MERLIN MD PTE LTD., Singapore (SG)

( * ) Notice: Subject to any disclaimer, the term of this patent is extended or adjusted under 35 U.S.C. 154(b) by 0 days.

(21) Appl. No.: 14/391,002

(22) PCT Filed: Apr. 5, 2013

(86) PCT No.: PCT/US2013/035517
§ 371 (c)(1),
(2) Date: Feb. 24, 2015

(87) PCT Pub. No.: WO2013/152327
PCT Pub. Date: Oct. 10, 2013

(65) Prior Publication Data
US 2015/0190221 A1 Jul. 9, 2015

Related U.S. Application Data

(60) Provisional application No. 61/621,434, filed on Apr. 6, 2012.

(51) Int. Cl.
*A61F 2/958* (2013.01)
*A61F 2/07* (2013.01)
(Continued)

(52) U.S. Cl.
CPC .......... *A61F 2/07* (2013.01); *A61F 2/90* (2013.01); *A61F 2/915* (2013.01); *A61F 2/958* (2013.01);
(Continued)

(58) Field of Classification Search
CPC ...... A61F 2/90; A61F 2/65; A61F 2002/9505; A61F 2002/9511; A61F 2002/9522;
(Continued)

(56) References Cited

U.S. PATENT DOCUMENTS

| 4,100,309 A | 7/1978 | Micklus et al. |
| 4,416,028 A | 11/1983 | Eriksson et al. |

(Continued)

FOREIGN PATENT DOCUMENTS

| EP | 815806 A2 | 1/1998 |
| EP | 0754435 B1 | 11/2000 |

(Continued)

OTHER PUBLICATIONS

Chatterjee, S., Lactosylceramide Stimulates Aortic Smooth Muscle Cell Proliferation, Biochemical and Biophysical Research Communications, Dec. 16, 1991, pp. 554-561, vol. 181, No. 2.

(Continued)

*Primary Examiner* — Wade Miles
(74) *Attorney, Agent, or Firm* — McDermott Will & Emery LLP

(57) ABSTRACT

A system and method are provided for treating an aneurysm or other vessel disease or defect. The present disclosure includes an expandable device for placement in a vessel, where the mechanically expandable device includes a membrane. Also disclosed is a delivery device constructed and arranged to position the expandable device such that the (Continued)

exterior surface of the expandable device engages with the inner surface of the vessel and maintains a fluid pathway through said vessel.

32 Claims, 24 Drawing Sheets

(51) Int. Cl.
    *A61F 2/915* (2013.01)
    *A61F 2/90* (2013.01)
    *A61F 2/82* (2013.01)

(52) U.S. Cl.
    CPC ............... *A61F 2002/823* (2013.01); *A61F 2002/91575* (2013.01); *A61F 2210/0004* (2013.01); *A61F 2210/0014* (2013.01); *A61F 2250/0023* (2013.01); *A61F 2250/0035* (2013.01); *A61F 2250/0097* (2013.01); *A61F 2250/0098* (2013.01)

(58) Field of Classification Search
    CPC .. A61F 2/962; A61F 2/966; A61F 2002/9665; A61F 2/958; A61F 2002/9583; A61F 2002/9586; A61F 2/07; A61F 2/075; A61F 2/954; A61F 2/848; A61F 2002/8483; A61F 2002/8486; A61F 2002/9517; A61M 25/0029
    See application file for complete search history.

(56) References Cited

U.S. PATENT DOCUMENTS

| | | |
|---|---|---|
| 4,503,569 A | 3/1985 | Dotter |
| 5,026,607 A | 6/1991 | Kiezulas |
| 5,041,441 A | 8/1991 | Radin et al. |
| 5,234,457 A | 8/1993 | Andersen |
| 5,348,553 A * | 9/1994 | Whitney .............. A61F 2/82 604/913 |
| 5,356,423 A | 10/1994 | Tihon et al. |
| 5,405,377 A | 4/1995 | Cragg |
| D359,802 S | 6/1995 | Fontaine |
| 5,421,955 A | 6/1995 | Lau et al. |
| 5,443,458 A | 8/1995 | Eury |
| 5,514,154 A | 5/1996 | Lau et al. |
| 5,562,725 A | 10/1996 | Schmitt et al. |
| 5,589,563 A | 12/1996 | Ward et al. |
| 5,601,593 A | 2/1997 | Freitag |
| 5,620,763 A | 4/1997 | House et al. |
| 5,630,840 A | 5/1997 | Mayer |
| 5,632,840 A | 5/1997 | Campbell |
| 5,637,113 A | 6/1997 | Tartaglia et al. |
| 5,639,278 A | 6/1997 | Dereume et al. |
| 5,658,331 A | 8/1997 | Della Valle et al. |
| 5,700,285 A | 12/1997 | Myers et al. |
| D390,957 S | 2/1998 | Fontaine |
| 5,716,393 A | 2/1998 | Lindenberg et al. |
| 5,718,973 A | 2/1998 | Lewis et al. |
| 5,735,893 A | 4/1998 | Lau et al. |
| 5,744,515 A | 4/1998 | Clapper |
| 5,766,238 A | 6/1998 | Lau et al. |
| 5,769,884 A | 6/1998 | Solovay |
| 5,810,870 A | 9/1998 | Myers et al. |
| 5,843,027 A | 12/1998 | Stone et al. |
| 5,843,172 A | 12/1998 | Yan |
| 5,858,556 A | 1/1999 | Eckert et al. |
| 5,866,217 A | 2/1999 | Stenoien et al. |
| 5,902,475 A | 5/1999 | Trozera et al. |
| 5,925,061 A | 7/1999 | Ogi et al. |
| 5,925,075 A | 7/1999 | Myers et al. |
| 5,948,018 A | 9/1999 | Dereume et al. |
| 5,951,599 A | 9/1999 | McCrory |
| 5,993,489 A | 11/1999 | Lewis et al. |
| 6,001,123 A | 12/1999 | Lau |
| 6,010,530 A | 1/2000 | Goicoechea |
| 6,017,577 A | 1/2000 | Hostetter et al. |
| 6,024,765 A | 2/2000 | Wallace et al. |
| 6,027,811 A | 2/2000 | Campbell et al. |
| 6,033,435 A | 3/2000 | Penn et al. |
| 6,036,720 A | 3/2000 | Abrams et al. |
| 6,056,775 A | 5/2000 | Borghi et al. |
| 6,056,776 A | 5/2000 | Lau et al. |
| 6,066,167 A | 5/2000 | Lau et al. |
| 6,093,199 A | 7/2000 | Brown et al. |
| 6,139,564 A | 10/2000 | Teoh |
| 6,140,127 A | 10/2000 | Sprague |
| 6,168,610 B1 | 1/2001 | Marin et al. |
| 6,174,328 B1 | 1/2001 | Cragg |
| 6,217,607 B1 | 4/2001 | Alt |
| 6,240,616 B1 | 6/2001 | Yan |
| 6,240,948 B1 | 6/2001 | Hansen, III et al. |
| 6,248,190 B1 | 6/2001 | Stinson |
| 6,258,120 B1 | 7/2001 | McKenzie et al. |
| 6,265,016 B1 | 7/2001 | Hostettler et al. |
| 6,270,523 B1 | 8/2001 | Herweck et al. |
| 6,309,367 B1 | 10/2001 | Boock |
| 6,312,463 B1 | 11/2001 | Rourke et al. |
| 6,315,791 B1 | 11/2001 | Gingras et al. |
| 6,371,980 B1 | 4/2002 | Rudakov et al. |
| 6,379,382 B1 | 4/2002 | Yang |
| 6,409,754 B1 | 6/2002 | Smith et al. |
| 6,416,474 B1 | 7/2002 | Penner et al. |
| 6,436,132 B1 | 8/2002 | Patel et al. |
| 6,451,050 B1 | 9/2002 | Rudakov et al. |
| 6,451,052 B1 | 9/2002 | Burmeister |
| 6,454,780 B1 | 9/2002 | Wallace |
| 6,485,507 B1 | 11/2002 | Walak et al. |
| 6,488,701 B1 | 12/2002 | Nolting et al. |
| 6,508,832 B1 | 1/2003 | Jalisi et al. |
| 6,511,979 B1 | 1/2003 | Chatterjee |
| 6,517,571 B1 | 2/2003 | Brauker et al. |
| 6,527,802 B1 | 3/2003 | Mayer |
| 6,533,905 B2 | 3/2003 | Johnson et al. |
| 6,547,815 B2 | 4/2003 | Myers |
| 6,582,461 B1 | 6/2003 | Burmeister et al. |
| 6,582,652 B2 | 6/2003 | Craig |
| 6,602,281 B1 | 8/2003 | Klein |
| 6,613,072 B2 | 9/2003 | Lau et al. |
| 6,613,074 B1 | 9/2003 | Mitelberg et al. |
| 6,623,520 B2 | 9/2003 | Jalisi |
| 6,652,574 B1 | 11/2003 | Jayaraman |
| D484,979 S | 1/2004 | Fontaine |
| 6,673,108 B2 | 1/2004 | Zilla et al. |
| 6,676,701 B2 | 1/2004 | Rourke et al. |
| 6,679,910 B1 | 1/2004 | Granada |
| 6,695,833 B1 | 2/2004 | Frantzen |
| 6,695,876 B1 | 2/2004 | Marotta et al. |
| 6,699,276 B2 | 3/2004 | Sogard et al. |
| 6,706,061 B1 | 3/2004 | Fischell et al. |
| 6,719,782 B1 | 4/2004 | Chuter |
| 6,733,523 B2 | 5/2004 | Shaolian et al. |
| 6,736,844 B1 | 5/2004 | Glatt et al. |
| 6,796,997 B1 | 9/2004 | Penn et al. |
| 6,802,851 B2 | 10/2004 | Jones et al. |
| 6,805,706 B2 | 10/2004 | Solovay et al. |
| 6,818,013 B2 | 11/2004 | Mitelberg et al. |
| 6,821,293 B2 | 11/2004 | Pinchasik |
| 6,855,154 B2 | 2/2005 | Abdel-Gawwad |
| 6,899,727 B2 | 5/2005 | Armstrong et al. |
| 6,936,055 B1 | 8/2005 | Ken et al. |
| 6,949,116 B2 | 9/2005 | Solymar et al. |
| 6,979,349 B1 | 12/2005 | Dang et al. |
| 7,029,493 B2 | 4/2006 | Majercak et al. |
| 7,041,127 B2 | 5/2006 | Ledergerber |
| 7,041,129 B2 | 5/2006 | Rourke et al. |
| 7,060,091 B2 | 6/2006 | Killion et al. |
| 7,105,019 B2 | 9/2006 | Hojeibane |
| 7,125,419 B2 | 10/2006 | Sequin et al. |
| 7,153,322 B2 | 12/2006 | Alt |
| 7,169,174 B2 | 1/2007 | Fischell et al. |
| 7,258,697 B1 | 8/2007 | Cox et al. |
| D553,746 S | 10/2007 | Fliedner |
| D553,747 S | 10/2007 | Fliedner |

(56) References Cited

U.S. PATENT DOCUMENTS

| | | |
|---|---|---|
| 7,306,622 B2 | 12/2007 | Jones et al. |
| 7,311,726 B2 | 12/2007 | Mitelberg et al. |
| 7,491,226 B2 | 2/2009 | Palmaz et al. |
| 8,075,609 B2 | 12/2011 | Penn et al. |
| 8,262,692 B2 | 9/2012 | Rudakov |
| 8,333,798 B2 | 12/2012 | Gandhi et al. |
| 8,500,751 B2 | 8/2013 | Rudakov et al. |
| 8,715,340 B2 | 5/2014 | Rudakov et al. |
| 8,915,952 B2 | 12/2014 | Rudakov |
| 8,920,430 B2 | 12/2014 | Rudakov et al. |
| 2002/0035394 A1 | 3/2002 | Fierens et al. |
| 2002/0042646 A1 | 4/2002 | Wall |
| 2002/0045931 A1 | 4/2002 | Sogard et al. |
| 2002/0049495 A1 | 4/2002 | Kutryk et al. |
| 2002/0062149 A1* | 5/2002 | Jang .................. A61F 2/91 623/1.16 |
| 2002/0065546 A1 | 5/2002 | Machan et al. |
| 2002/0111543 A1 | 8/2002 | Penner et al. |
| 2002/0120276 A1 | 8/2002 | Greene et al. |
| 2002/0123788 A1 | 9/2002 | Sanders Millare et al. |
| 2002/0123801 A1* | 9/2002 | Pacetti .................. A61F 2/07 623/1.46 |
| 2002/0133224 A1 | 9/2002 | Bajgar et al. |
| 2002/0151968 A1 | 10/2002 | Zilla et al. |
| 2003/0014075 A1 | 1/2003 | Rosenbluth et al. |
| 2003/0018294 A1 | 1/2003 | Cox |
| 2003/0040772 A1 | 2/2003 | Hyodoh et al. |
| 2003/0060782 A1 | 3/2003 | Bose et al. |
| 2003/0060871 A1 | 3/2003 | Hill et al. |
| 2003/0074049 A1 | 4/2003 | Hoganson et al. |
| 2003/0074053 A1 | 4/2003 | Palmaz et al. |
| 2003/0093111 A1 | 5/2003 | Ken et al. |
| 2003/0100945 A1 | 5/2003 | Yodfat et al. |
| 2003/0124279 A1 | 7/2003 | Sridharan et al. |
| 2003/0171801 A1 | 9/2003 | Bates |
| 2003/0229286 A1 | 12/2003 | Lenker |
| 2003/0229393 A1 | 12/2003 | Kutryk et al. |
| 2003/0233141 A1 | 12/2003 | Israel |
| 2004/0029268 A1 | 2/2004 | Colb et al. |
| 2004/0078071 A1 | 4/2004 | Escamilla et al. |
| 2004/0087998 A1 | 5/2004 | Lee et al. |
| 2004/0116998 A1 | 6/2004 | Erbel et al. |
| 2004/0138736 A1 | 7/2004 | Obara |
| 2004/0170685 A1 | 9/2004 | Carpenter et al. |
| 2004/0172121 A1 | 9/2004 | Eidenschink et al. |
| 2004/0186562 A1 | 9/2004 | Cox |
| 2004/0193206 A1 | 9/2004 | Gerberding et al. |
| 2004/0204754 A1 | 10/2004 | Kaplan et al. |
| 2004/0220665 A1 | 11/2004 | Hossainy et al. |
| 2005/0008869 A1 | 1/2005 | Clark |
| 2005/0010281 A1 | 1/2005 | Yodfat et al. |
| 2005/0043787 A1 | 2/2005 | Kutryk et al. |
| 2005/0075716 A1 | 4/2005 | Yan |
| 2005/0090888 A1 | 4/2005 | Hines et al. |
| 2005/0096725 A1 | 5/2005 | Pomeranz et al. |
| 2005/0124896 A1 | 6/2005 | Richter et al. |
| 2005/0137677 A1 | 6/2005 | Rush |
| 2005/0137680 A1 | 6/2005 | Ortiz et al. |
| 2005/0154447 A1 | 7/2005 | Goshgarian |
| 2005/0154448 A1 | 7/2005 | Cully et al. |
| 2005/0171593 A1 | 8/2005 | Whirley et al. |
| 2005/0240210 A1* | 10/2005 | Park .................... A61F 2/95 606/192 |
| 2005/0267568 A1 | 12/2005 | Berez et al. |
| 2005/0283220 A1 | 12/2005 | Gobran et al. |
| 2006/0020322 A1 | 1/2006 | Leynov et al. |
| 2006/0036308 A1 | 2/2006 | Goshgarian |
| 2006/0036311 A1 | 2/2006 | Nakayama et al. |
| 2006/0106421 A1 | 5/2006 | Teoh |
| 2006/0121080 A1 | 6/2006 | Lye et al. |
| 2006/0136037 A1 | 6/2006 | DeBeer et al. |
| 2006/0142849 A1 | 6/2006 | Killion |
| 2006/0149355 A1 | 7/2006 | Mitelberg et al. |
| 2006/0155355 A1 | 7/2006 | Jung |
| 2006/0173530 A1 | 8/2006 | Das |
| 2006/0200230 A1 | 9/2006 | Richter |
| 2006/0200234 A1 | 9/2006 | Hines |
| 2006/0206199 A1 | 9/2006 | Churchwell et al. |
| 2006/0217799 A1 | 9/2006 | Mailander et al. |
| 2006/0224237 A1 | 10/2006 | Furst et al. |
| 2006/0259123 A1 | 11/2006 | Dorn |
| 2006/0265051 A1 | 11/2006 | Caro et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0287710 A1 | 12/2006 | Lendlein et al. |
| 2007/0038288 A1 | 2/2007 | Lye et al. |
| 2007/0083258 A1 | 4/2007 | Falotico et al. |
| 2007/0088387 A1 | 4/2007 | Eskridge et al. |
| 2007/0088425 A1 | 4/2007 | Schaeffer |
| 2007/0100321 A1 | 5/2007 | Rudakov et al. |
| 2007/0100430 A1 | 5/2007 | Rudakov et al. |
| 2007/0112415 A1 | 5/2007 | Bartlett |
| 2007/0150045 A1 | 6/2007 | Ferrera |
| 2007/0173921 A1 | 7/2007 | Wholey et al. |
| 2007/0198048 A1* | 8/2007 | Behan ................. A61F 2/04 606/194 |
| 2007/0203573 A1 | 8/2007 | Rudakov et al. |
| 2007/0213800 A1 | 9/2007 | Fierens et al. |
| 2007/0276477 A1 | 11/2007 | Lee et al. |
| 2007/0288083 A1 | 12/2007 | Hines |
| 2008/0004653 A1 | 1/2008 | Sherman et al. |
| 2009/0054966 A1 | 2/2009 | Rudakov et al. |
| 2009/0132022 A1 | 5/2009 | Banas |
| 2010/0063531 A1 | 3/2010 | Rudakov et al. |
| 2010/0063582 A1 | 3/2010 | Rudakov |
| 2010/0217234 A1* | 8/2010 | Grovender ............ A61L 29/06 604/523 |
| 2011/0152998 A1 | 6/2011 | Berez et al. |
| 2015/0196405 A1 | 7/2015 | Rudakov et al. |

FOREIGN PATENT DOCUMENTS

| | | |
|---|---|---|
| EP | 1086663 A1 | 3/2001 |
| EP | 1 129 666 | 9/2001 |
| EP | 1391184 A1 | 2/2004 |
| EP | 1470795 A1 | 10/2004 |
| EP | 1254623 B1 | 1/2005 |
| EP | 0864301 B1 | 3/2005 |
| EP | 0947204 B1 | 5/2005 |
| EP | 1543798 A3 | 10/2005 |
| EP | 1121911 B1 | 12/2006 |
| EP | 1797844 A1 | 6/2007 |
| EP | 1550477 A4 | 11/2010 |
| JP | 1-254623 | 10/1989 |
| JP | 08-047540 | 2/1996 |
| JP | 08-141090 | 6/1996 |
| JP | H 11-509130 A | 8/1999 |
| JP | 11-299901 A | 11/1999 |
| JP | 2002-516706 A | 6/2002 |
| JP | 2002-529193 A | 9/2002 |
| JP | 2002-345972 A | 12/2002 |
| JP | 2003-250880 A | 9/2003 |
| JP | 2003-250907 A | 9/2003 |
| JP | 2003-265620 A | 9/2003 |
| JP | 2003-528690 A | 9/2003 |
| JP | 2004-049584 A | 2/2004 |
| JP | 2008-506503 A | 3/2008 |
| JP | 2009-525775 A | 7/2009 |
| JP | 2010-268950 A | 12/2010 |
| JP | 2011-067663 A | 4/2011 |
| JP | 2011-516158 A | 5/2011 |
| WO | WO-94/16646 A1 | 8/1994 |
| WO | WO-97/17913 A1 | 5/1997 |
| WO | WO-98/14137 A1 | 4/1998 |
| WO | WO-99/02092 A1 | 1/1999 |
| WO | WO-99/62432 A1 | 12/1999 |
| WO | WO-00/01308 A1 | 1/2000 |
| WO | WO-00/06145 A1 | 2/2000 |
| WO | WO-00/28922 A1 | 5/2000 |
| WO | WO-99/58084 A9 | 5/2000 |
| WO | WO-00/47134 A1 | 8/2000 |
| WO | WO-00/48517 A1 | 8/2000 |
| WO | WO-00/51522 A1 | 9/2000 |

(56) References Cited

FOREIGN PATENT DOCUMENTS

| WO | WO-00/56247 A1 | 9/2000 |
| WO | WO-01/03607 A3 | 7/2001 |
| WO | WO-01/87184 A1 | 11/2001 |
| WO | WO-01/93782 A1 | 12/2001 |
| WO | WO-02/22024 A2 | 3/2002 |
| WO | WO-02/051336 A1 | 7/2002 |
| WO | WO-02/069783 A2 | 9/2002 |
| WO | WO-02/078762 A1 | 10/2002 |
| WO | WO-02/078764 A1 | 10/2002 |
| WO | WO-03/026713 A1 | 4/2003 |
| WO | WO-03/049600 A2 | 6/2003 |
| WO | WO-01/66167 A3 | 8/2003 |
| WO | WO-03/065881 A2 | 8/2003 |
| WO | WO-03/082152 A1 | 10/2003 |
| WO | WO-2004/022150 A1 | 3/2004 |
| WO | WO-2004/028405 A3 | 6/2004 |
| WO | WO-2004/000379 A8 | 8/2004 |
| WO | WO-2005/000165 A1 | 1/2005 |
| WO | WO-2005/065580 A1 | 7/2005 |
| WO | WO-2005/086831 | 9/2005 |
| WO | WO-2005/094725 A1 | 10/2005 |
| WO | WO-2005/094726 A1 | 10/2005 |
| WO | WO-2006/033641 A1 | 3/2006 |

OTHER PUBLICATIONS

Reul, J. et al., Long-Term Angiographic and Histopathalogic Findings in Experimental Aneurysms of the Carotid Bifurcation Embolized with Platinum and Tungsten Coils, American Journal of Neuroradiology, Jan. 1997, pp. 35-42, vol. 18.

International Search Report, dated Jul. 29, 2013, for PCT Application PCT/US2013/035517, entitled "Devices and Methods for Treating an Aneurysm," filed Apr. 15, 2013.

Office Action issued in corresponding European Patent Application No. 13773098.2, dated Apr. 25, 2018.

* cited by examiner

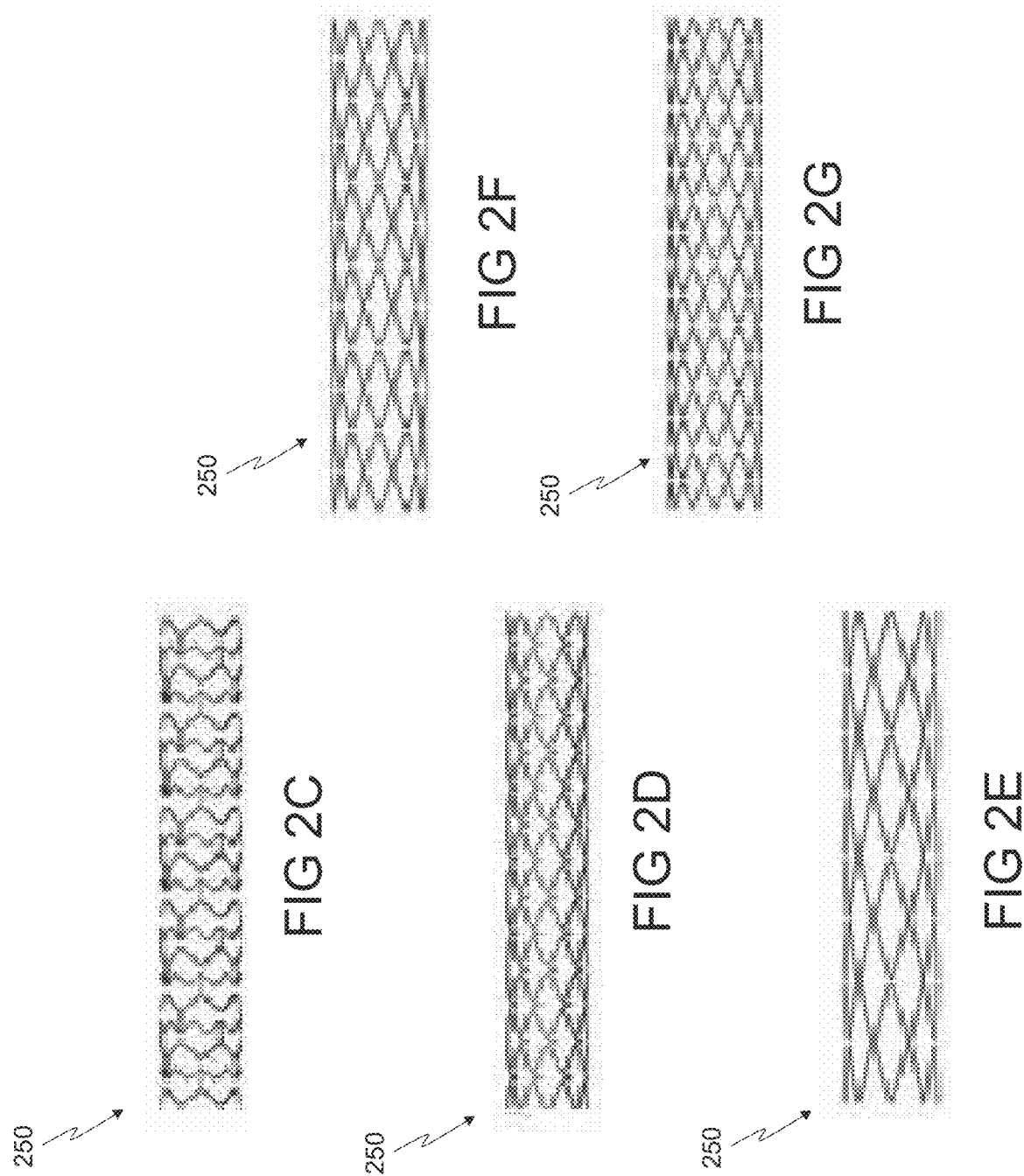

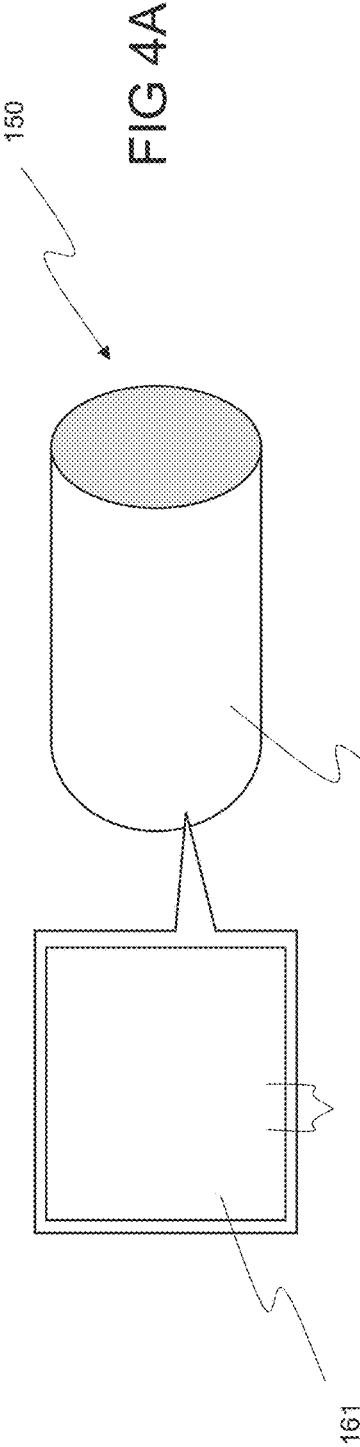
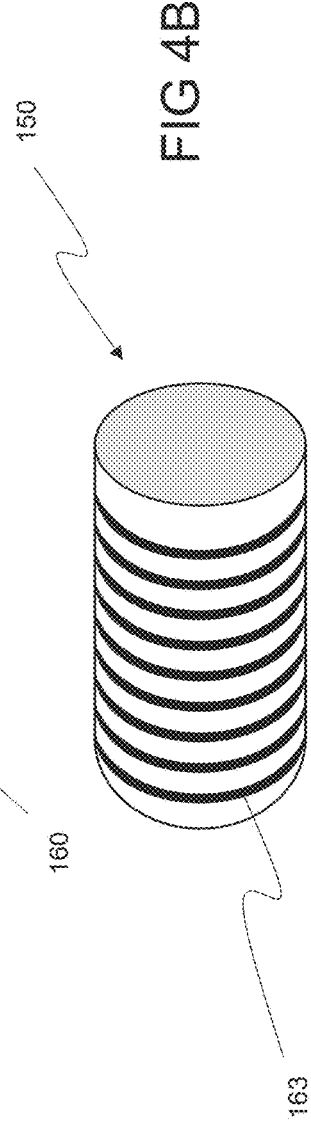
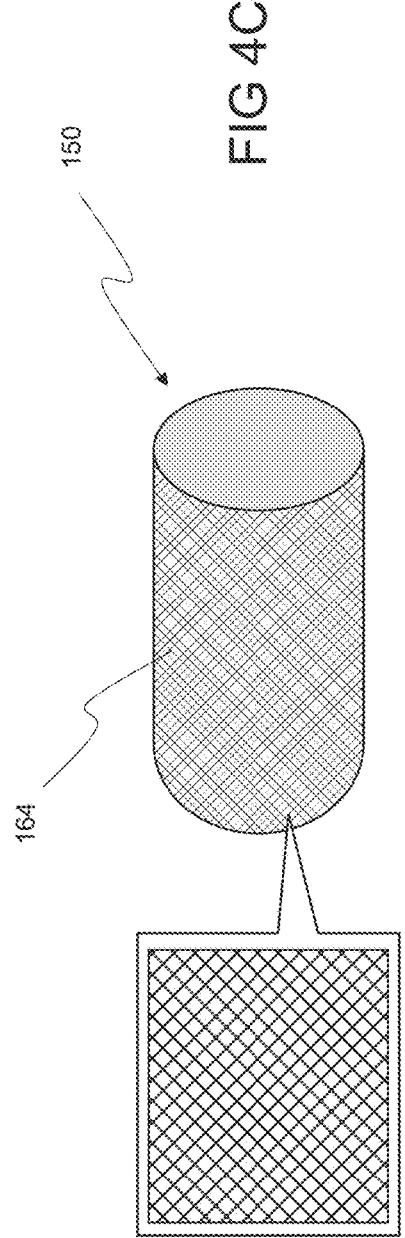
FIG 4A
FIG 4B
FIG 4C

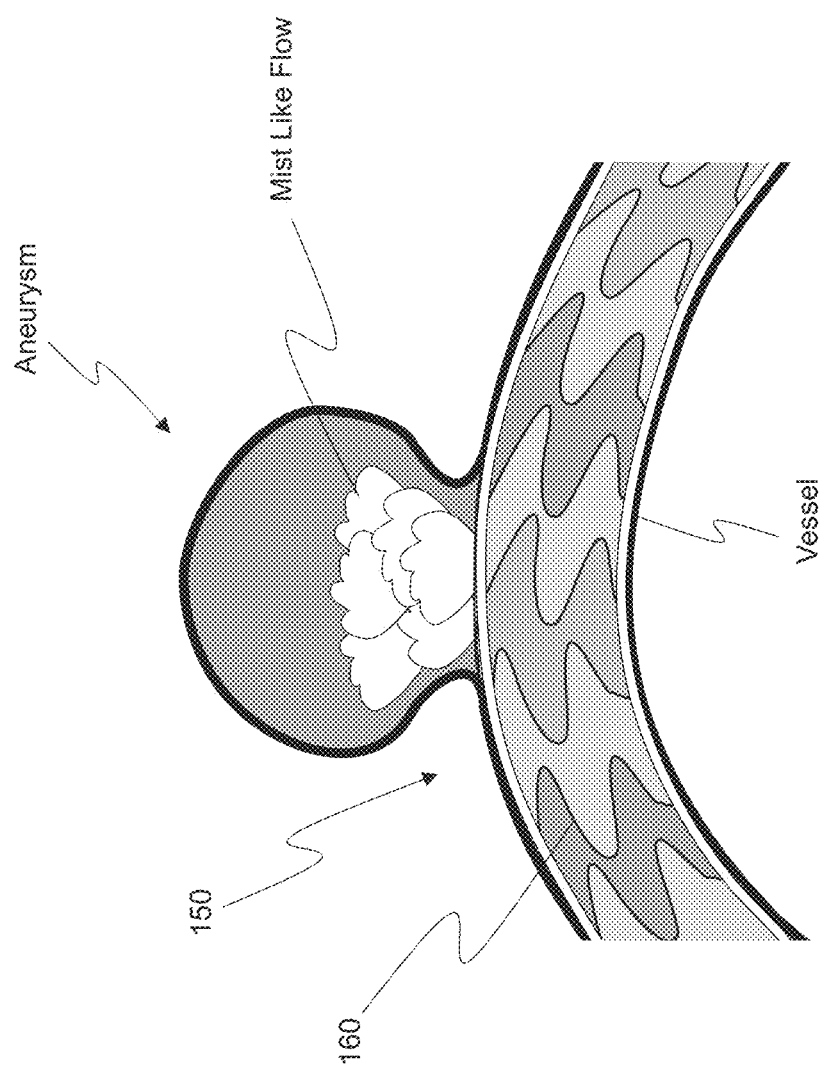

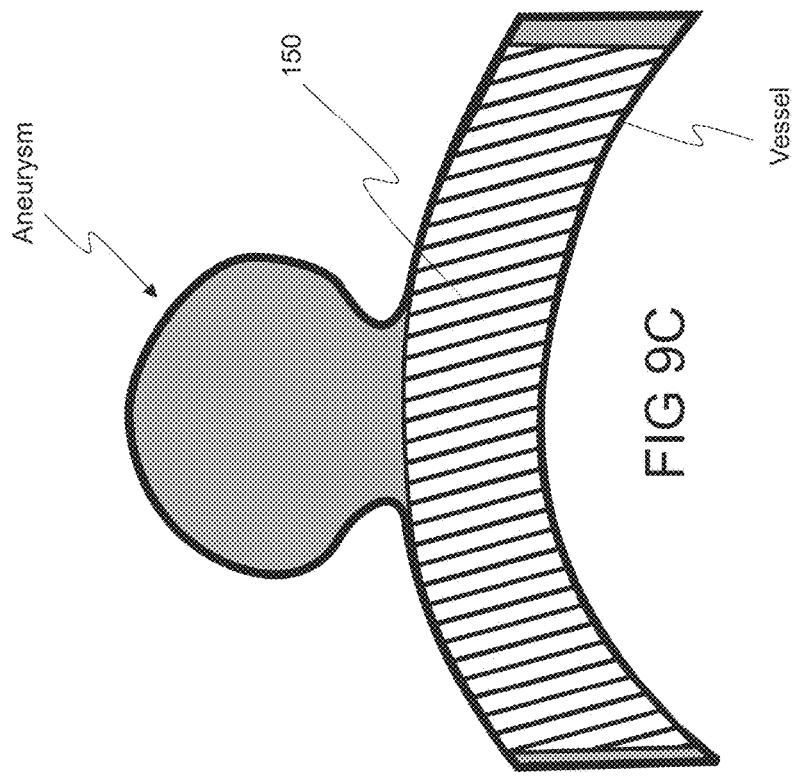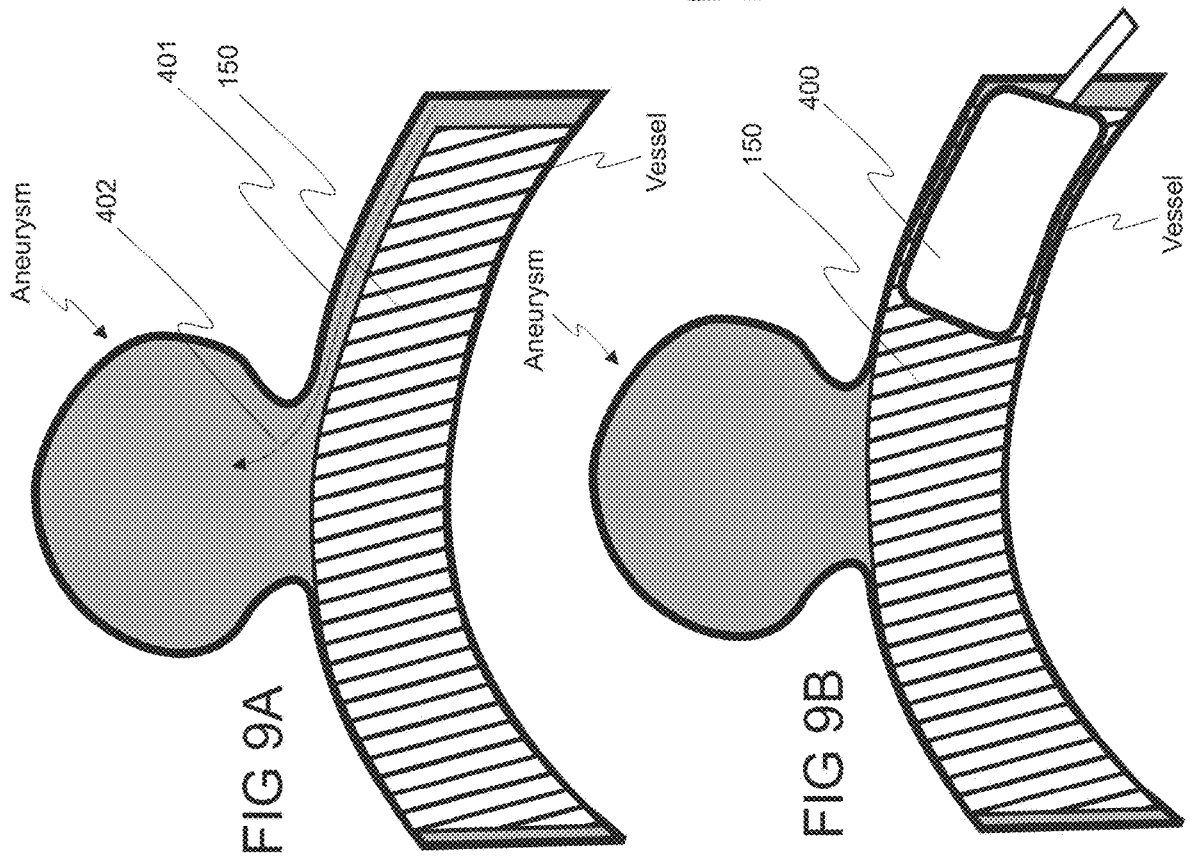

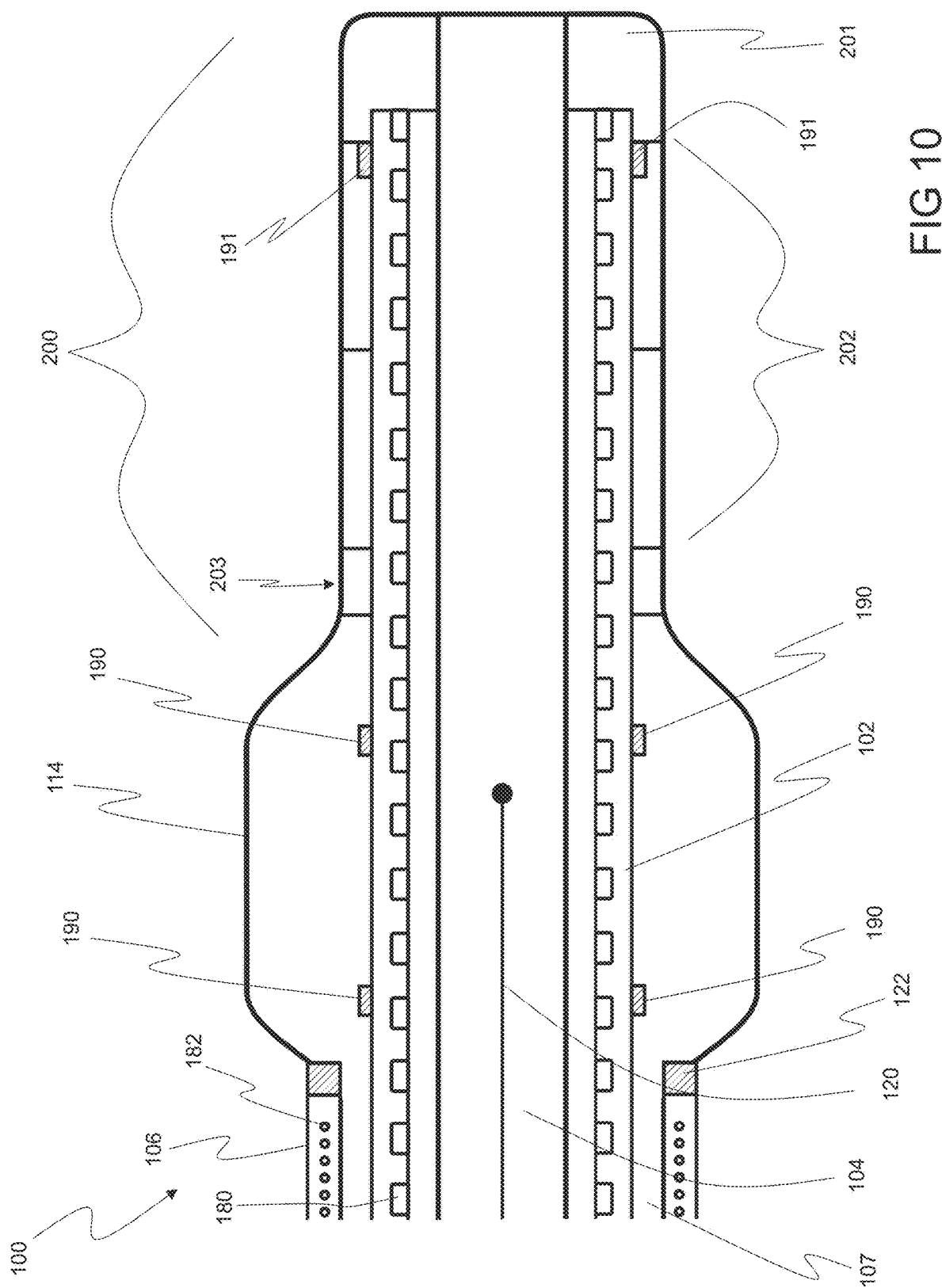

Six Month Post-Implant

Immediate Post-Implant (within 15 mins)

Pre-Implant

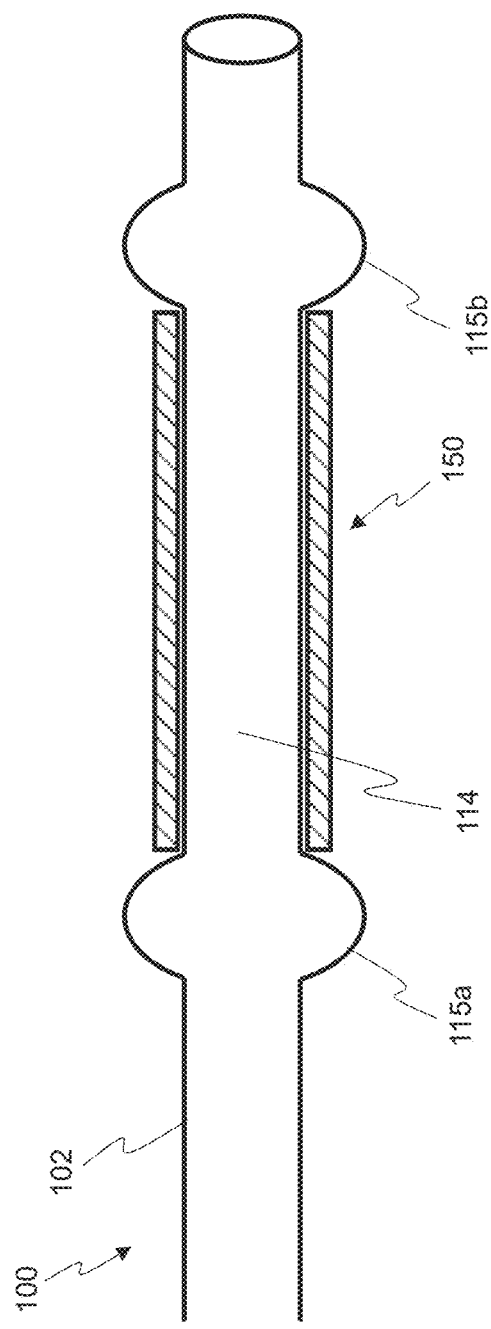
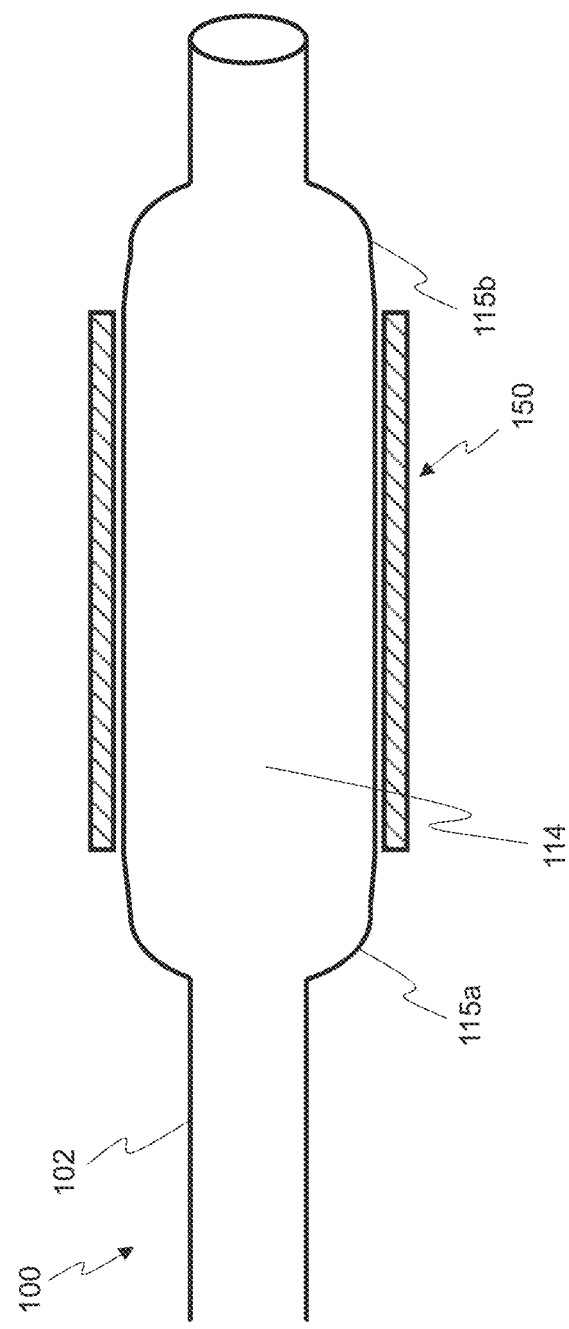

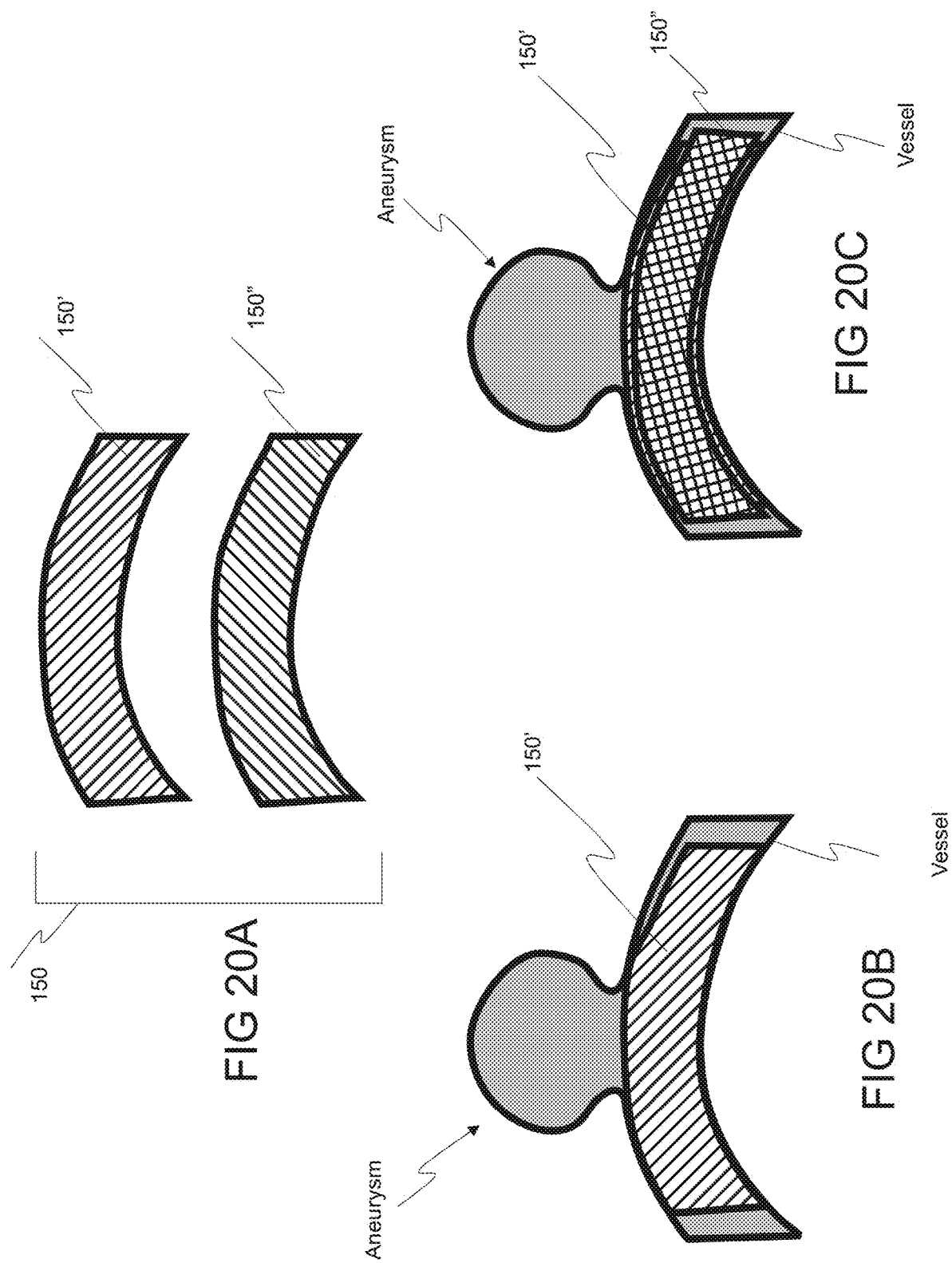

DEVICES AND METHODS FOR TREATING AN ANEURYSM

RELATED APPLICATIONS

This application is the U.S. National Phase under 35 U.S.C. § 371 of International Application No. PCT/US2013/035517, filed Apr. 5, 2013, which claims the benefit of U.S. Provisional Patent Application Ser. No. 61/621,434, filed on Apr. 6, 2012. The entirety of which is incorporated by reference, as if fully set forth herein.

FIELD

The present disclosure relates to a medical device for insertion into a body vessel to treat vessel disease and malformations.

BACKGROUND

Vascular diseases include aneurysms causing hemorrhage, atherosclerosis causing the occlusion of blood vessels, vascular malformations and tumors. Vessel occlusion and rupture of an aneurysm within the brain are causes of stroke. Aneurysms fed by intracranial arteries can grow within the brain to a point where their mass and size alone, without rupture, can cause a stroke or the symptoms of stroke, requiring surgery for removal of the aneurysms or other clinical intervention. Additionally, these expanding vessels can exert pressure on surrounding nerves which can lead to conditions such as diplopia, ptosis, pounding headaches, delirium, and hemi-paresis, just to name a few.

Occlusion of coronary arteries, for example, is a common cause of heart attack. Diseased and obstructed coronary arteries can restrict the flow of blood in the heart and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Conventional open-heart surgery is, of course, very invasive and traumatic for patients undergoing such treatment. Therefore, alternative, less traumatic methods are highly desirable.

One of the alternative methods is balloon angioplasty, a technique in which a folded balloon is inserted into a stenosis, which occludes or partially occludes an artery. The balloon is inflated to open the occluded artery, restoring or otherwise improving blood flow. Another alternative method is atherectomy that is a technique in which occlusive atheromas are cut from the inner surface of the arteries. Both methods suffer from reocclusion with a certain percentage of patients.

A recent preferred therapy for vascular occlusions is placement of an expandable metal wire-frame within the occluded region of blood vessel, to maintain patency after an occlusion treatment. The implant is delivered to the desired location within a vascular system by a delivery means, usually a catheter. These interventional procedures avoid the various complications of surgery, including heart-lung bypass, opening the chest, and general anesthesia.

When inserted and deployed in a vessel, duct or tract (hereinafter "vessel") of the body, for example, a coronary artery after dilatation of the artery by balloon angioplasty, an implant acts as a prosthesis to maintain the vessel open. The implant usually has an open-ended tubular form with interconnected struts as its sidewall to enable its expansion from a first outside diameter, which is sufficiently small to allow the implant to traverse the vessel to reach a site where it is to be deployed, to a second outside diameter sufficiently large enough to engage the inner lining of the vessel for retention at the site. An implant is typically delivered in an unexpanded state to a desired location in a body lumen and then expanded. The implant is expanded via the use of a mechanical device such as a balloon, or the implant may be self-expanding.

Usually a suitable implant for successful interventional placement should possess features of relatively non-allergenic reaction and other biocompatibility, sufficient radiopacity to be visualized with X-ray, freedom from distortion when using magnetic resonance imaging (MRI), sufficient flexibility to be intraluminally advanced to an implantation site, strong resistance to vessel recoil, and sufficient thinness to minimize obstruction to flow of blood (or other fluid or material in vessels other than the cardiovascular system).

Implantable medical devices have been utilized for delivery of drugs or other agents for different clinical applications. Typically, the agents are coated onto the surfaces of the implantable devices or mixed within polymeric materials that are coated onto the surfaces of the implants. Current devices experience uncontrolled release of agent, have limitations on types of agents used, and may comprise a bulky agent delivery mechanism.

There is a need for systems, methods and devices that provide improved treatment of blood vessels, including improved treatment of neurovascular aneurysms.

SUMMARY

The subject technology is illustrated, for example, according to various aspects described below. These are provided as examples and do not limit the subject technology. It is noted that any of the aspects below may be combined in any combination.

According to an embodiment of the present disclosure, a system for treating a diseased vessel comprises an expandable device configured to radially expand from a first position to a second position; a membrane expandable in response to the expansion of the expandable device; and a delivery device configured to position the expandable device such that the exterior surface of the expandable device engages with the inner surface of the vessel and maintains a fluid pathway through said vessel. The system can be used to treat one or more diseased vessels with a diameter ranging between 1.25 mm and 30 mm.

The system may be used to treat various types of aneurysms, including but not limited to: intracranial; fusiform; berry; saccular; carotid-cavernous fistula; and combinations of these. Additionally, the system can be used to treat aneurysms of various sizes, including but not limited to: regular sized aneurysms; large or giant neck aneurysms; wideneck aneurysms; aneurysms arising from a parent vessel wherein the parent vessel comprises a diameter of approximately 2.0 mm to 5.0 mm; and combinations of these. Further, the system can be used to treat a bifurcation and/or trifurcation intracranial aneurysm.

The system is constructed and arranged to near immediately and near completely occlude an aneurysm while maintaining patency in crossed side branches. The system is constructed and arranged to achieve remodeling of a diseased vessel that results in improved hemodynamics within or proximate to the diseased vessel as well as correct the unfavorable hemodynamics that may have caused the aneurysm. The system is constructed and arranged to promote healing, avoid causing a significant inflammatory response, and avoid creating necrotic tissue. In some embodiments, the system achieves delivery of the expandable device in a one-step procedure. In some embodiments, the system may be disposed after a single use.

Embodiments of the system of the present disclosure can be used in other applications including but not limited to: to treat ischemia; to treat a neurovascular disease such as a hemorrhagic aneurysm, atherosclerosis, emboli such as ruptured vulnerable plaque emboli, carotid artery occlusion, and arterio-venous malformations; to treat peripheral aneurysms such as popliteal, renal, and abdominal aortic; to treat myocardial infarction; to treat an arterio-venous fistula; and combinations of these.

In some embodiments, the expandable device is configured to be plastically deformed during a radial expansion from the first position to the second position. In some embodiments, the delivery device comprises a retractable sheath configured to maintain the expandable device in the first position prior to retraction, and to release the expandable device to the second position after retraction, where the expandable device is resiliently biased in the second position. In some embodiments, the expandable device comprises at least two portions wherein the first portion is plastically deformable during the radial expansion from the first position to the second position, and the second portion is resiliently biased in the second position. In some embodiments, the expandable device may expand to a diameter of a vessel in its healthy state plus 0.5 mm, for example 2.0 mm to 5.0 mm.

The expandable device may be constructed and arranged to cover the surface of an aneurysm such that the aneurysm can be treated with a single expandable device, for example, the aneurysm coverage ranges from 65% to 95%.

The expandable device may comprise a frame with a generally tubular structure having an inner surface and an exterior surface, where the exterior surface comprises a plurality of interconnected struts having interstitial spaces therebetween. The frame may be inserted into a vessel and implanted therein. The frame may include at least six points, for example seven points. The frame may comprise a material selected from the group consisting of: stainless steel and/or Nitinol, such as 316L stainless steel; a polymer; and combinations of these. The frame may comprise a coating, for example a radiopaque coating, such as a gold radiopaque coating. The frame may comprise wires having welded ends that are arranged in a braid. The frame may comprise a rigidity sufficient to cause straightening of the diseased vessel as the expandable device is expanded. After expansion of the expandable device, the frame may be reshaped and/or further expanded via a post-dilatation balloon catheter to prevent leaks around the expandable device, for example when the frame comprises at least one plastically deformable portion. In some embodiments, the proximal portion of the expandable device is reshaped and/or further expanded by the post dilatation balloon prior to the distal portion of the expandable device.

The exterior surface of the frame may be encapsulated, completely or partially, for example, by a polymer material configured for atraumatic placement in a vessel. Typically, the polymer coating comprises a soft, super-elastic, biocompliant, ultra-thin material selected from the group consisting of: fluoropolymers; polyimide; silicone; polyurethanes; polyurethane ether; polyurethane ester; polyurethane polycarbonate; polyurethane urea; copolymers of these; and combinations of these. Additionally or alternatively, the frame may include a lubricous coating. The interior surface of the frame may comprise a smooth surface such that micro-turbulence is minimized.

The frame may include at least two wires, typically eight to thirty-eight wires, and more typically eight to fourteen wires. Wire diameter may range from 0.0005" to 0.004", for example 0.003". Wire material may be selected from the group consisting of: metal; shape memory alloys such as Nitinol; shape memory polymers; and combinations of these. In some embodiments, the wires may comprise a composite material, for example, each wire includes an outer tube an inner core that are fused together, where the inner core comprises a radiopaque material, and the outer core comprises a deformation resistance material, or vice versa. Other inner and outer core materials include but are not limited to: metal; shape memory alloy; shape memory polymer; Platinum/Tungsten; Cobalt Chromium; and combinations of these.

The at least two wires may comprise a weave configuration, for example a braided configuration. The braid configuration can be achieved via a one-over-one-under method; a one-over-two-under method; and/or a two-over-two-under method. The braid configuration creates a frame with a diamond cell, where the diamond cell comprises a width ranging from 0.00 mm to 0.26 mm, or ranging from 0.15 mm to 0.053 mm, e.g. 0.13 mm.

In one embodiment, the at least two wires comprise a first wire, a second wire, and a braid angle therebetween. The braid angle may range from 1° to 179°. In some embodiments, the braid angle ranges from 80° to 145°. In some embodiments, the braid angle approximates 90°. The braid angle may be uniform or it may vary about a circumference and a length of the expandable device.

The expandable device may comprise a length of 7.0 mm to 40.0 mm, and can be shortened via a cutting procedure. In some embodiments, the length of the expandable device can comprise a length of the aneurysm neck to be treated plus an additional 15 mm, for example a length ranging from 14 mm to 26 mm. When expanded, the expandable device may comprise an outer diameter ranging from 1.5 mm to 5.0 mm, and said device is constructed and arranged to maintain a relatively constant diameter under systolic pressures after expansion. In some cases, changes in vessel diameter may cause limited diameter changes to the expandable device.

The expandable device may comprise a polymer material, such as a polymer selected from the group consisting of: a polyurethane; a polyurethane ether; a polyurethane ester; a polyurethane polycarbonate; a polyurethane urea; copolymers of these; and combinations of these.

The expandable device may be pre-mounted onto the delivery device. The expandable device can be loaded onto a delivery device comprising a micro-catheter and a delivery wire. In some embodiments, the self-expandable device can be retracted into the micro-catheter after 90% or less of the self-expandable device is advanced from the distal end of the micro-catheter.

The expandable device may comprise a coating, for example, a hydrophilic coating. The system may further include a second expandable device configured to expand from a first position to a second position. In some embodiments, the first expandable device comprises a self-expandable device and the second expandable device comprises a balloon expandable device, for example where the first device provides adequate coverage in a vessel, and the second device provides adequate apposition between the first and second expandable devices and the vessel. The first and second expandable devices may be similar or dissimilar in construction, e.g. materials, braid configuration, coatings, radiopacity, size and the like. The first expandable device may be implanted, and the second expandable device may be implanted in approximately the same position. The first and second devices may be implanted such that they overlap one another, having any amount of overlap, for example where the overlapping portion is proximate an aneurysm. The first and second devices may be implanted in a tandem configuration.

The expandable device may include at least one marker, including but not limited to: radiopaque markers such as markers that can be viewed with X-ray or fluoroscopy; visible markers such as markers that can be viewed with a visible intraluminal camera; infrared markers such as markers that can be viewed with an infrared intraluminal camera; ultrasound markers such as markers that can be viewed with external ultrasound or intravascular ultrasound; magnetic markers such as markers that can be viewed with MRI; and combinations of these. In some embodiments, a first marker can be positioned on a distal portion of the frame, and a second marker can be positioned on a proximal portion of the frame. The proximal and/or distal portion of the frame may include at least one ring where the at least one ring includes at least two teeth constructed and arranged to secure at least one marker within the at least one ring. The at least one ring may be coated with a radiopaque material, for example a gold material.

The system can include a membrane. The membrane may include a polymer such as BioSpan®2F which can be described as a segmented polyurethane including a polytetramethyleneoxide-based aromatic polyurethane urea with mixed aliphatic and cycloaliphatic diamine chain extender. The membrane may include a polymer such as BioSpan® F which can be described as a segmented polyurethane with fluorocarbon as surface modifying endgroups. Alternatively or additionally, the membrane may comprise a polymer material selected from the group consisting of: a fluoropolymers; a polyimide; a silicone; an alkoxy-silicone; a polyurethane; a polyurethane ether; a polyurethane ester; a polyurethane polycarbonate; a polyurethane urea; copolymers of these; and combinations of these. Additional examples of a polymer material include: a biodegradable polylactide; a polyether; a polyethylene glycol (biostable); a poly(DL-lactide-co-caprolactone) (PLC); a poly(DL-lactide-co-glycolide) (PLGA) (typically biodegradable); a polyether of varying composition and molecular weight; a polyester; a polycarbonate diol; a copolymer of these; and combinations of these. In some embodiments, the polymer material has a molecular weight ranging from MW 100-2000. The polymer can comprise at least one chain extender comprising one or more diolsor multi-functional groups comprising one or more bioactive surface modifying groups. Non-limiting examples of chain extenders include: methylene diisocyanate; toluene diisocyanate; hexamethylenediisocyanate; diisocyanates; alkyl-triols such as glycerol and increasing molecular weight analogs; triamines; orthoformic acid; phosphates such as Inositol trisphosphate; Calcitriol; cyclic polyols (Cyclitols); Ciceritol; short chain functionalized amino acids; polyketides characterized by three hydroxyl groups such as Tautomycin; lipidoid C12-200; fluoroalkane; fluoroalkanols; and combinations of these. In some embodiments, the polymer can comprise at least one end group that can be functionalized prior to incorporation into the polymer. In some embodiments, the polymer can comprise a reactively functionalized polymer including: an allyl-alkyl hydroxide or amine; a siloxy-containing reactive functionality; a poly methyoxy or polyethyoxy low molecular weight complex; and combinations of these. The polymers described herein can be configured as nanoparticles; self encapsulating particles (e.g. for multiple drug delivery systems); coatings for stents, catheters, or other medical devices; and combinations of these.

The polymer can comprise one or more radio-lucent or radio-opaque materials selected from the group consisting of: a halogen such as bromine or iodine; a ceramic; a metal such as stainless steel, gold, silver or platinum; and combinations of these. The polymer can be embedded with a gel and/or gels-sol comprising the one or more radio-lucent or radio-opaque materials.

The membrane may include at least a biodegradable portion, for example a first portion of the membrane may biodegrade and a second portion may be relatively stable after implantation over time. Alternatively, the entire membrane may comprise a biodegradable material. The membrane may completely surround an exterior surface of the expandable device, or it may cover at least a portion of the device, for example a circumferential portion. The membrane may comprise a plurality of polymeric strips, such 0.075 mm wide strips positioned less than 100 microns apart. For example, the strips may be between about 0.050 mm and about 0.100 mm wide. By further example, the strips may be between about 50 microns and about 200 microns apart. The membrane may comprise a woven mesh.

In some embodiments, the expandable device can comprise one or more drugs, reagents and/or other agents. For example, one or more drugs and/or other agents can be coated onto a surface of the expandable device, mixed, embedded, or covalently bonded with polymeric materials that are coated onto the surfaces of the expandable device. In some embodiments, one or more drugs and/or other agents can be loaded into a suitable polymer vehicle that can then be bonded to the polymeric coating, e.g. a membrane, on the expandable device. In some embodiments, the membrane can comprise the polymer comprising one or more drugs and/or other agents. In some embodiments, the polymer comprises a dendrimer-type polymer which can be described as a macromolecule, where the dendrimer-type polymer can comprise one or more drugs and/or other agents configured to diffuse from the polymer over a period of time, for example a time period matching the time course of restenosis, such as at least four weeks and up to one year. As used herein, a "dendrimer-type polymer" comprises dendrimers and/or dendrons. As used herein, "dendrimer" means a repetitively branched molecule, including arborols and cascade molecules. A dendrimer may be symmetric around a core and may adopt a spherical three-dimensional morphology. As used herein, "dendron" means a molecule comprising branches from a single chemically addressable focal point.

Non-limiting examples of drugs and/or other agents include: anti-proliferative agents; anti-inflammatory agents; cell regeneration promoting agents; nanoparticles; drug-eluting nanoparticles; nanoparticle gels; and/or restenosis inhibiting agents. The polymer coating can be configured for controlled and long-term drug and/or other agent delivery to the vessel.

The membrane comprises a thickness such that turbulence into side branches in minimized, for example, the membrane may comprise a thickness ranging from 0.0005" (10 um) to 0.005", for example 0.001". In some embodiments, the membrane thickness decreases post-expansion of the expandable device, for example to a thickness ranging from 0.0005" (10 um) to 0.002". The membrane thickness can vary along the length and/or along the circumference of the expandable device.

The membrane may comprise a non-porous and non-permeable material such that blood circulation to the aneurysm is prevented. Additionally or alternatively, the membrane may comprise at least a porous portion comprising pores. The pores may be uniform across the membrane or portion of the membrane, for example, the pores may uniformly sized and spaced. Preferably, the pores are sized and spaced such that blood is not throttled into the aneurysm. The pores may comprise a diameter between 20 microns and 200 microns. The pores may comprise a diameter between 50 microns and 120 microns. The pores may comprise a diameter between 80 microns and 100 microns. Conversely, the pores may be non-uniform across the membrane or portion of the membrane, where non-uniformity can be achieved by varying at least one of the pore size; distance between adjacent pores; or pore shape. For example, the pores may have a smaller diameter at a mid portion of the expandable device and a larger diameter at the proximal and distal portions of the expandable device.

The pores may be drilled, for example via a laser, such that the pores expand from an initial diameter to a final diameter upon expansion of the expandable device. For example, the initial diameter of the pores can range form 20 microns to 50 microns, and the final diameter can range from 50 microns to 120 microns, or 80 microns to 100 microns. Additionally or alternatively, the pores may be drilled to a final diameter, i.e. diameter remains relatively constant upon expansion of the expandable device. For example, the diameter of the pores can range from 50 microns to 120 microns, or 80 microns to 100 microns. In some embodiments, pore size can vary, for example, the pores may have a smaller diameter at a mid portion of the expandable device and a larger diameter at the proximal and distal portions of the expandable device. The pores may be drilled in a geometric shape selected from the group consisting of: circular; elliptical; rectangular; trapezoidal; and combinations of these. The various geometric shapes comprise a major axis, and the length of the major axis may be approximately 50 microns to 120 microns, or 80 microns to 100 microns. Similar to the size of the pores, the shape of the pores may transition from a first shape to a second shape upon expansion of the expandable device, for example a pore may be drilled to comprise a circular shape and expand to comprise an elliptical shape. One or more membrane pores can be drilled so there is little to no contact with the struts of the expandable device.

The membrane comprises an inner surface, where the inner surface may comprise a smooth surface such that micro-turbulence is prevented.

The membrane may be expandable up to 1000%. The membrane may be expandable up to 140%.

The system includes a delivery device comprising a catheter comprising at least one shaft, a guidewire lumen and an inflation lumen, where the catheter includes a distal portion with a profile, for example a profile between 0.045" to 0.060". The guidewire lumen may comprise an entry port positioned 5.5 mm to 6.5 mm from the distal tip of the catheter, and said lumen may be positioned at the geometric center of the catheter shaft. The inflation lumen can be used for inflating a balloon and/or transporting a fluid. The delivery device may comprise two shafts, a first shaft and a second shaft. The first shaft may surround the guidewire lumen and may comprise at least two layers, for example a co-extrusion of Pebax™ 55D and HDPE, or a co-extrusion of Pebax™ 55D and PTFE, typically materials with a durometer ranging from 35D to 72D, more typically 55D. The second shaft may surround the inflation lumen.

The first and second shafts may each comprise a coil, a first and a second coil, that surrounds the guidewire and inflation lumens, respectively. The first coil may reside between the two co-extruded layers of the first shaft. Including the first coil, the first shaft may comprise a durometer ranging from 35D to 72D, typically 55D. Including the second coil, the second shaft may comprise a durometer ranging from 40D to 72D, typically 62D. The first and/or second coil may comprise stainless steel and/or Nitinol, for example 304V stainless steel. The first and second coils comprise a width, a thickness and a pitch. Coil width typically ranges from 0.001" to 0.004", more typically 0.00225". Coil thickness typical ranges from 0.0005" to 0.002", more typically 0.008". Coil pitch typically ranges from 0.004" to 0.012", more typically 0.0058".

The second shaft, having a distal end and a proximal end, can comprise a length such that the second shaft distal end terminates proximal to an inflatable element. For example, where a proximal end of the inflatable element is bonded to the first shaft via a proximal balloon bond, the second shaft distal end is flush with the proximal balloon bond. In another embodiment, the second shaft distal end can extend distal to the inflatable element. For example, where a distal end of the inflatable element is bonded to the first shaft via a distal balloon bond, the second shaft distal end is flush with the distal balloon bond. In this embodiment, the second shaft distal end can be bonded or not bonded to the distal balloon bond. In yet another embodiment, the second shaft distal end can terminate proximal to the distal balloon bond, for example approximately 1 mm proximal to the distal balloon bond. In the cases where the second shaft extends through the inflatable element, the second shaft can comprise at least one hole to assist in inflation and deflation of the inflatable element. The at least one hole can comprise a diameter ranging from approximately 0.005" to 0.025", or ranging from approximately 0.010" to 0.015". In some embodiments the shaft comprises one to twenty holes. In some embodiments, the second shaft comprises five to ten holes. The second shaft can comprise two or more holes that can be arranged uniformly or non-uniformly along the second shaft, for example holes can comprise similar or dissimilar size and spacing.

The delivery device may comprise a working length of at least 140 cm, for example greater than or equal to 145 cm.

The delivery device may comprise a coating, including but not limited to: a hydrophilic coating; a lubricous coating; and combinations of these.

The delivery device may comprise a guidewire rapid exchange device. The delivery device may comprise a co-axial design, comprising co-axial shafts.

The delivery device comprises a distal segment and a proximal portion, and the distal segment may be more flexible than said proximal portion. The distal segment may be approximately 9 mm in length.

The delivery device may include at least one marker, for example a marker positioned on a distal portion of the delivery device. The at least one marker comprises a marker selected from the group consisting of: radiopaque markers such as markers that can be viewed with X-ray or fluoroscopy; visible markers such as markers that can be viewed with a visible intraluminal camera; infrared markers such as markers that can be viewed with an infrared intraluminal camera; ultrasound markers such as markers that can be viewed with external ultrasound or intravascular ultrasound;

magnetic markers such as markers that can be viewed with MRI; and combinations of these.

The delivery device may include an inflatable element configured to expand the expandable device from the first position to the second position. The inflatable element may be attached to the distal end of the shaft such that the inflatable element extends approximately 1 mm to 3 mm past the distal end of the shaft. The inflatable element may expand from a first position to a second position at an opening pressure and a rated burst pressure such that the second position comprises a controlled diameter, for example a diameter of 2.0 mm to 0.0 mm. The opening pressure may range from 3.5 atm to 6 atm, and the rated burst pressure may range from 10 atm to 14 atm.

The inflatable element may comprise at least one marker, for example a distal marker and a proximal marker. The spacing between the distal and proximal marker may depend on the size on the expandable device. The marker spacing for a short expandable device, e.g. 15 mm long, may be approximately 18 mm, and at least approximately 17.5 mm. The marker spacing for a moderate expandable device, e.g. 20 mm long, may be approximately 23.5 mm, and at least approximately 23 mm. The marker spacing for a long expandable device, e.g. 25 mm long, may be approximately 28.5 mm, and at least approximately 28 mm. The marker spacing for an extra-long expandable device, e.g. 30 mm long, may be approximately 33.5 mm, and at least approximately 33 mm.

The inflatable element may comprise a proximal portion, a mid portion, and a distal portion, where the proximal and distal portions are configured to be expanded such that the outer diameter of the proximal and distal portions is greater than that of the mid portion. A tubular conduit, e.g. a Polyimide conduit, a reinforced PTFE conduit, or a polished stainless steel conduit, can be placed around the proximal and/or distal portions such as to define the desired outer diameter of said portions. Alternatively or additionally, a similarly constructed tubular conduit can be placed around the expandable device to prevent expansion of said device during the expansion of the proximal and/or distal portions of the inflatable element.

The inflatable element may comprise a balloon, for example a balloon having at least one fold where the at least one fold is oriented such that the balloon refolds by torqueing the delivery device in a particular direction. The balloon can be configured as a 6-fold balloon; a 5-fold balloon; a 3-fold balloon; or a spiral-fold balloon. The balloon can comprise a material selected from the group consisting of: irradiated polyethylene; polyethylene terephthalate; polyvinylchloride; nylon such as Nylon 12, L2140, L25, L2125, and L2101; copolymer nylon such as Pebax™; and combinations of these. The balloon can comprise a distal taper length and/or a proximal taper length, e.g. 1.5 mm to 5 mm.

The system may further comprise a post-dilatation balloon configured to eliminate a false lumen between a vessel wall and the expandable device. In some embodiments, the post-dilatation balloon comprises a shaft comprising an inflation lumen constructed and arranged similarly to the second shaft of the delivery device, as has been described herein.

The system may further comprise a catheter configured to introduce the delivery device including the expandable device in a vessel, for example a 6F guide catheter.

The system may further comprise a guidewire, for example a 0.014" guidewire.

The system may further comprise a tubular member, for example a shaped mandrel having a curved portion and a looped proximal end. The curved portion may comprise a 45° bend. The shaped mandrel may comprise a radius ranging from 0.29" to 0.33", e.g. 0.315". The shaped mandrel may comprise an outer diameter ranging from 0.01" to 0.02", e.g. 0.015". The shaped mandrel may comprise a length ranging from 19.0" to 20.0", e.g. 19.5".

According to another aspect of the present disclosure, a method for treating a diseased vessel comprises accessing a target vessel via a delivery device and expanding an expandable device from a first position to a second position radially outward such that an exterior surface of the expandable device engages with an inner surface of the vessel so as to maintain a fluid pathway though the vessel, where the delivery device is configured to position the expandable device, and where the expandable device comprises a membrane expandable from a first position to a second position in response to the expansion of the expandable device.

The expandable device may be expanded via an inflatable element. The inflatable element may be attached to the distal end of the shaft such that the inflatable element extends approximately 1 mm to 3 mm past the distal end of the shaft. The inflatable element may expand from a first position to a second position at an opening pressure and a rated burst pressure such that the second position comprises a controlled diameter, for example a diameter of 2.0 mm to 5.0 mm. The opening pressures may range from 3.5 atm to 6 atm, and the rated burst pressure may range from 10 atm to 14 atm.

The inflatable element may comprise a balloon, for example a balloon having at least one fold where the at least one fold is oriented such that the balloon refolds by torqueing the delivery device in a particular direction. The balloon can be configured as a 6-fold balloon; a 5-fold balloon; a 3-fold balloon; or a spiral-fold balloon. The balloon can comprise a material selected from the group consisting of: irradiated polyethylene; polyethylene terephthalate; polyvinylchloride; nylon such as Nylon 12, L2140, L25, L2125, and L2101; copolymer nylon such as Pebax™; and combinations of these.

To prevent deployment of the expandable device prior to reaching the target vessel, the method may further comprise expanding a proximal portion and a distal portion of the inflatable element, where the proximal and distal portions are configured to be expanded such that the outer diameter of the proximal and distal portions is greater than that of the mid portion. A tubular conduit, e.g. a Polyimide conduit, a reinforced PTFE conduit, or a polished stainless steel conduit, can be placed around the proximal and/or distal portions such as to define the desired outer diameter of said portions. Alternatively or additionally, a similarly constructed tubular conduit can be placed around the expandable device to prevent expansion of said device during the expansion of the proximal and/or distal portions of the inflatable element.

The expansion of the proximal and/or distal portion of the inflatable element may be via thermal energy. In some embodiments, the expansion occurs via a cold process, for example, via the introduction of pressurized Nitrogen. In some embodiments, the expansion occurs via the introduction of heat for a duration of time. For example, the inflatable element can be placed in an over set to 50° C. to 70° C. for a duration of 30 seconds to 15 minutes, or the inflatable element can be placed an over set to 55° C. to 65° C. for a duration of 5 minutes to 10 minutes. In the heat induced method, pressurized Nitrogen may be added to the oven, for example at a pressure ranging from 5 psi to 60 psi, or at a pressure ranging from 10 psi to 50 psi. Upon reaching the desired location within the vessel, the inflatable element may be further inflated such that the outer diameter of the inflatable element approximately matches an inner diameter of the expandable element in preparation for deployment of the expandable device.

The expandable device may be self-expandable. In some embodiments, the self-expandable device is expanded via a delivery device comprising a retractable sheath. In some embodiments, the self-expandable device is expanded by movement of a wire, such that the device is deployed from a micro-catheter.

The expandable device may comprise both balloon expandable and self-expanding portions.

The method further comprises inserting the expandable device into the vessel, where the expandable device comprises an exterior surface and an inner surface. The exterior surface may be smooth such that insertion into the vessel is atraumatic and micro-turbulence is prevented or minimized. This can be achieved via a coating, for example a membrane. The membrane may be comprised of a polymer and/or lubricous materials. Similarly, the inner surface may be smooth such that frictional surface micro-turbulence is prevented or minimized. The expandable device may straighten the vessel after said device is expanded from the first position to the second position.

The method may further comprise expanding the expandable device such that the expanded diameter matches that of a healthy vessel plus 0.5 mm, for example 2.0 mm to 5.0 mm. In some embodiments, the expandable device can be over-expanded such that the device inner diameter matches that of the vessel inner diameter.

The method may further comprise maintaining a relatively constant diameter of the expandable device under systolic pressures after expansion.

The method may further comprise visualizing the delivery device and/or the expandable device, for example using a marker such as a radiopaque marker. Various imaging means can include MRI, Dyna CT, Angio CT, angiography or fluoroscopy. Said visualization can be used to confirm the position of the delivery deice and/or the expandable device before, during and/or after the expansion of the expandable device.

The method may further comprise delivering one or more drugs, reagents and/or other agents to the vessel. For example, one or more drugs and/or other agents can be coated onto a surface of the expandable device, mixed, embedded, or covalently bonded with polymeric materials that are coated onto the surfaces of the expandable device. In some embodiments, one or more drugs and/or other agents can be loaded into a suitable polymer vehicle that can then be bonded to the polymeric coating, e.g. a membrane, on the expandable device. In some embodiments, the membrane can comprise the polymer comprising one or more drugs and/or other agents. In some embodiments, the polymer comprises a dendrimer-type polymer which can be described as a macromolecule, where the dendrimer-type polymer can comprise one or more drugs and/or other agents configured to diffuse from the polymer over a period of time, for example a time period matching the time course of restenosis, such as at least four weeks and up to one year. Non-limiting examples of drugs and/or other agents include: anti-proliferative agents; anti-inflammatory agents; cell regeneration promoting agents; nanoparticles; drug-eluting nanoparticles; nanoparticle gels; and/or restenosis inhibiting agents. The polymer coating can be configured for controlled and long-term drug and/or other agent delivery to the vessel.

The method may further comprise molding the expandable device via a post-dilatation balloon post-expansion from the first position to the second position such that no leak is observed, i.e. space between the expandable device and the vessel is reduced or eliminated.

Multiple steps may be performed prior to the delivery of the implantable device, for example air may be purged from the delivery device. An access site may be prepared, where the access site can be selected from the group consisting of: femoral artery; radial artery; and brachial artery. An inflatable element may be attached to the delivery device. The delivery device may be tracked over a tubular member, for example a shaped mandrel such as to improve tracking of the delivery device. A guidewire may be positioned in a target vessel such that the delivery device can be loaded onto a proximal end of the guidewire and advanced over the guidewire to a vessel.

Subsequent to implantation of the expandable device, the inflatable element can be deflated, and the delivery device can be removed from the vessel.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 2A, 2B, 2C, 2D, 2E, 2F, and 2G illustrate various embodiments of a self-expanding implant made of wires, consistent with embodiments of the present disclosure;

FIGS. 4A, 4B, and 4C illustrate an implant including various coverings, consistent with embodiments of the present disclosure;

FIG. 7 illustrates the hemodynamics proximate an implanted device, consistent with embodiments of the present disclosure;

FIGS. 9A, 9B, and 9C illustrate an implanted device, prior to, during, and subsequent to post-implantation plastic deformation, consistent with embodiments of the present disclosure;

FIG. 10 illustrates a distal portion of an implant delivery device, consistent with embodiments of the present disclosure;

FIG. 17A illustrates a distal portion of a delivery device including a balloon, where the proximal and distal ends of the balloon have been expanded such that an implant is stabilized on the delivery device, prior to implantation, consistent with embodiments of the present disclosure;

FIG. 17B illustrates the balloon of FIG. 17A further expanded for deployment and implantation of the implant, consistent with embodiments of the present disclosure;

FIG. 20A illustrates an implant including a first expandable device and a second expandable device, consistent with embodiments of the present disclosure;

FIG. 20B illustrates the first expandable device of FIG. 20A implanted within a vessel, consistent with embodiments of the present disclosure; and FIG. 20C illustrates the second expandable device of FIG. 20A also implanted within the vessel of FIG. 20B, consistent with embodiments of the present disclosure.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Reference will now be made in detail to embodiments of the present disclosure, examples of which are illustrated in the accompanying drawings. The same reference numbers will be used throughout the drawings to refer to the same or like parts.

Figure 1:
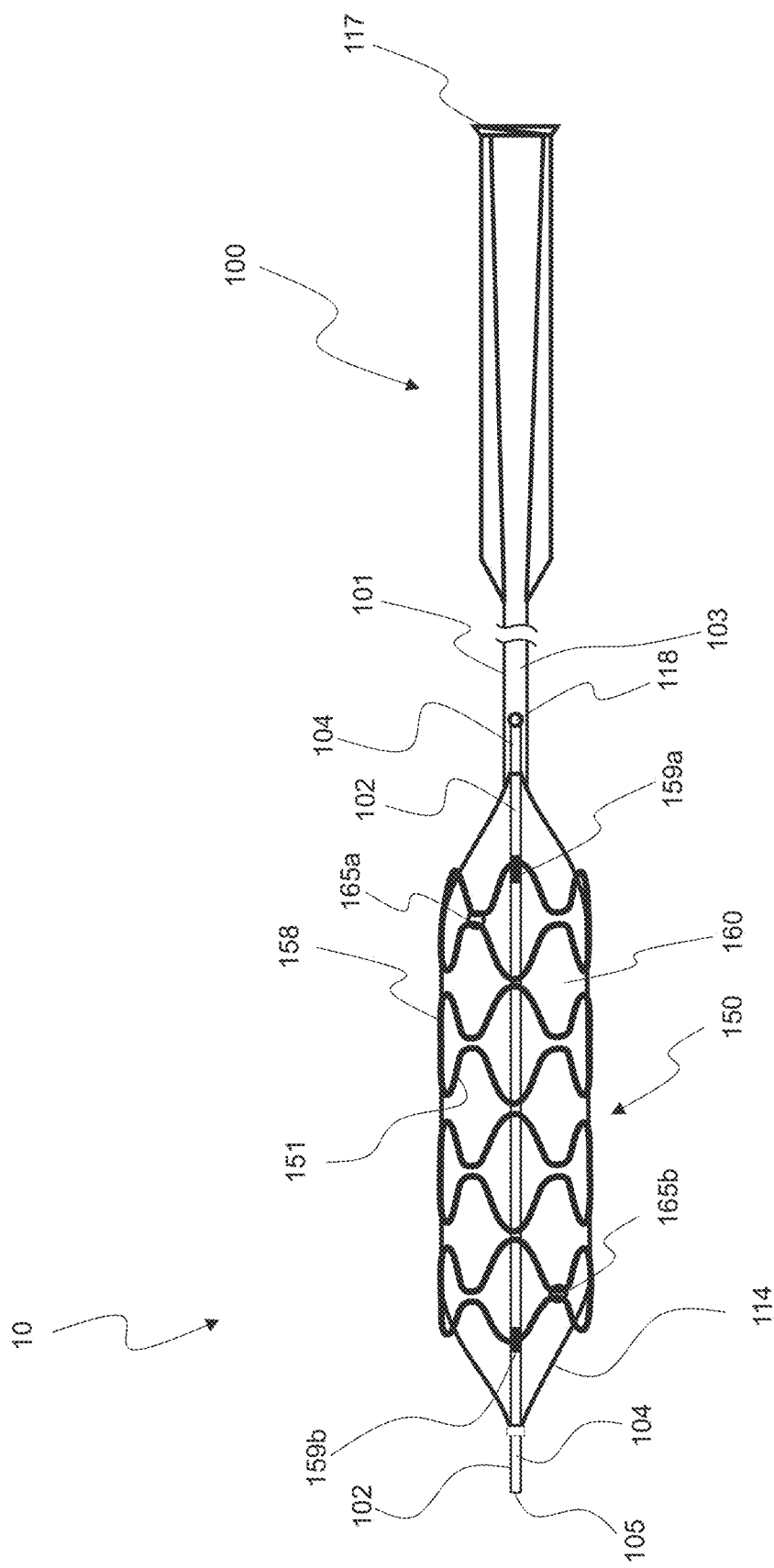
FIG. 1 illustrates a schematic of a system for treating a diseased vessel, consistent with embodiments of the present disclosure.

FIG. 1 illustrates a schematic of a system, consistent with embodiments of the present disclosure. System 10 may be used to treat a diseased vessel, for example, an intracranial aneurysm, typically arising from a parent vessel with a diameter of approximately 2.0 mm to 5.0 mm, with a single mechanically expandable device, for example, implant 150. The implants described herein provide enhanced surface coverage of a diseased vessel ranging from 65% to 95%. Vessels with a large range of diameter may be treated by system 10 and implant 150, such as vessels with diameters between 1.25 mm and 30 mm. Additionally, system 10 may be used to treat an aneurysm or other vessel malformation selected from the group consisting of: regular sized aneurysm; large or giant neck aneurysm; wideneck aneurysm; fusiform aneurysm; berry aneurysm; saccular aneurysm; carotid-cavernous fistula; and combinations of these. Further, system 10 may be configured to treat a bifurcation or trifurcation intracranial aneurysm between at least two bodily vessels, for example, upon the introduction of at least a second device to the treatment site. System 10 may be configured to provide immediate and complete occlusion of an aneurysm and a subsequent remodeling of a vessel that results in improved hemodynamics while maintaining patency in crossed side branches. Angiographic evidence has shown an immediate reduction of blood flow into the aneurysm upon deployment of implant 150. In some cases, complete stasis of blood flow occurs within 15 minutes to one hour, as the mural thrombus, consisting of platelets and fibrin, forms. Typically, imaging performed during a twenty four hour follow-up (e.g. DynaCT and/or AngioCT imaging), has shown complete exclusion of the aneurysm. After implantation, macrophages infiltrate the clot, and circulating regenerator cells begin to adhere to implant 150, permanently sealing off the neck of the aneurysm. The thrombus matures over the next 2-3 weeks as fibroblasts enter the clot and differentiate into myofibroblasts. These myofibroblasts express the contractile protein α-smooth muscle actin(α-SMA) which causes the aneurysm to contract in a disorganized fashion and into a subendothelial mass of connective tissue. In some cases, complete contraction of the aneurysm has been observed (e.g. via MRI) within six months. Further, system 10 is biocompatible and shows no significant inflammatory response, necrosis, or adverse histological event. Using system 10, an aneurysm may be treated with a single clinical procedure. System 10 is typically a single use system (i.e. used to treat one patient).

System 10 may be used in a variety of applications such as for implantation in one or more vessels, typically vessels between 2.5 mm and 5.0 mm in diameter. System 10 may be used to treat ischemia, such as oxygen depravation due to atherosclerotic stenosis or an embolic event such as the rupture or potential rupture of vulnerable plaque. System 10 may be used to treat a vascular malformation, such as an aneurysm, an arteriovenous malformation, or an arteriovenous fistula. Implant locations include but are not limited to: neurovascular sites, such as to treat a hemorrhagic or other intracranial brain aneurysms; in-situ vessels of the heart, such as to treat an occluded coronary artery; grafts proximate the heart, such as to treat a saphenous vein graft previously placed in a coronary artery bypass procedure; central vascular locations, such as to treat an abdominal aortic aneurysm; and peripheral sites, such as to treat an aneurysm in a popliteal or renal artery.

System 10 includes delivery device 100 configured to position a mechanically expandable device, implant 150, in a vessel such that the exterior surface of implant 150 is expanded to engage the inner surface of the vessel so as to maintain the flow of fluid, e,g. blood, through the vessel. Implant 150 typically includes membrane 160 which may expand in response to the expansion of implant 150. Membrane 160 or another portion of device 100 may include a coating, such as a hydrophilic coating and/or a coating configured to release one or more drugs or other agents, described further below. One or more drugs, reagents or other agents can be coated onto one or more surfaces of device 100. Alternatively or additionally, one or more agents can be mixed, embedded, or covalently bonded with polymeric materials that are coated onto one or more surfaces of device 100. Alternatively or additionally, one or more agents can be loaded into a suitable vehicle (e.g. a polymer solution) that can subsequently be bonded to device 100. Membrane 160 is typically a porous membrane, such as the porous membrane described in reference to FIGS. 4A and 16 herebelow.

Implant 150, having a generally tubular structure, includes frame 158 where frame 158 includes a plurality of struts 151 and spaces therebetween. Implant 150 can be self-expandable (e.g. resiliently biased in the expanded state), implant 150 can be balloon expandable (e.g. plastically deformable via an inserted balloon), or implant 150 may include at least a first portion that is self-expandable and at least a second portion that is balloon expandable, as is described in detail herebelow. In a typical embodiment, implant 150 can expand to the "healthy" (e.g. non diseased) diameter of a vessel, plus an additional 0.5 mm. In vessels with healthy diameters between 2.75 mm and 4.0 mm, implant 150 can be expanded to approximately 3.25 mm to 4.5 mm, respectively. In some embodiments, implant 150 can expand to a diameter of a healthy vessel plus a value less than 0.5 mm, or less than 0.25 mm. In some embodiments, implant 150 can be expanded such implant 150 inner diameter approximates the inner diameter of the vessel.

The length of implant 150 may be selected to be the length of an aneurysm neck plus 15 mm. For example, a first end of implant 150 can be positioned 5 mm proximal to a proximal end of the aneurysm neck, and a second end of implant 150 can be positioned 10 mm distal to the distal end of the aneurysm neck. Once radially expanded, implant 150 may be configured to maintain a relatively constant diameter under systolic pressures. In some embodiments, changes in vessel diameter may cause limited diameter changes to implant 150. In some instances, an aneurysm may have a small neck, e.g. 1.5 mm to 2.0 mm, and in this case, device 100 can have a length of approximately 12 mm to 17 mm, typically 14 mm. Implant 150 length and material characteristics may be chosen such that a vessel in which implant 150 is to be implanted does not straighten more than would be well tolerated by the vessel.

While implant 150 may have a variety of forms and configurations, FIG. 1 illustrates a shape in which adjacent strut crests undergo wide separation upon expansion, and portions of struts 151 transition to a transverse, almost fully lateral orientation relative to the longitudinal axis of implant 150. In one embodiment, frame 158 is formed from a stainless steel material and/or Nitinol material, for example 316L stainless steel. Frame 158 provides a rigidity such that frame 158 slightly straightens the vessel upon expansion of implant 150, resulting in improved blood flow, including correction of the unfavorable hemodynamics that may have caused the aneurysm. Additionally, frame 158 is plastically deformable or otherwise may be reshaped by a post-dilatation balloon, not shown, but configured to further expand implant 150, such as to ensure that no leak is observed between the vessel wall and implant 150, as is described in detail in reference to FIGS. 9A-9C herebelow. Frame 158 can also include at least one marker to increase visibility, for example a radiopaque marker, or one or more portions of frame 158 may be constructed of radiopaque materials. In one embodiment, frame 158 includes more than two markers, for example, two markers positioned on the distal end of frame 158 and two markers positioned on the proximal end of frame 158.

Frame 158 includes an interior surface which is smooth and continuous, thus eliminating or minimizing frictional surface micro-turbulence. Also, frame 158 may include an exterior surface completely encapsulated with a polymer coating, not shown, but configured to minimize vessel wall injury, such as injury caused during delivery and when compressed during cardiac cycles. The polymer coating may further protect from an undesired frame 158 material effects, such as a heavy metal ion response, for example, a Nickel allergic reaction. The polymer coating is preferably a soft, super-elastic, bio-compliant, ultra thin polymer selected from the group consisting of: fluoropolymers, polyimides, silicones, polyurethanes, polyurethanes ethers, polyurethane esters, polyurethane polycarbonate, polyurethane ureas, mixtures and copolymers thereof, and combinations of these. Additionally, the polymer coating may ensure that the exterior surface does not include any acute points or sharp edges such that frame 158 is atraumatic to the vessel wall, e.g. does not cut the endothelium. In some embodiments, a polymer coating is not included on proximal rings 165a and/or distal rings 165b, such as to allow distal and/or proximal ends of implant 150 to expand further (e.g. not be constrained by a polymer coating), ensuring better adaptation to the vessel wall. In addition, the removal (or not including) of the polymer coating from rings 165a and 165b and/or the struts 151 proximate to rings 165a and/or 165b can allow blood to flow through struts 151 without disturbing flow. Further, uncoated struts 151 and/or proximal rings 165a and/or distal rings 165b may help anchor implant 150 to the vessel wall. In some embodiments, the polymer coating may take the form of a membrane, for example, membrane 160. In other embodiments, a polymer coating surrounding all or a portion of frame 158 is included in addition to membrane 160. In some embodiments, rings 165a and/or 165b may be coated with a radiopaque material, for example a gold material.

Membrane 160 may comprise a polymer material. Polymers may be selected from the group consisting of: fluoropolymers, polyimides, silicones, polyurethanes, polyurethanes ethers, polyurethane esters, polyurethane polycarbonate, polyurethane ureas, mixtures and copolymers thereof, and combinations of these. Membrane 160 may be biodegradable, or it may include portions that are biodegradable and portions that remain relatively stable after implantation. In one embodiment, membrane 160 may completely surround the exterior surface (i.e. full length and circumference) of implant 150. In another embodiment, membrane 160 surrounds a portion of the full length of implant 150, around the full or partial circumference of implant 150. In yet another embodiment, membrane 160 covers a portion of the circumference of implant 150, along a partial or full length of implant 150. In yet another embodiment, membrane 160 may be in the form of strips; such as in the configurations shown in FIGS. 3A-3C herebelow.

In a typical embodiment, membrane 160 has a thickness such that turbulence into side branches is minimized. For example, membrane 160 thickness may range from 0.0005" to 0.005", typically 0.001". In some embodiments, membrane 160 thickness decreases post-expansion of implant 150. For example, membrane 160 thickness can range from 0.001" to 0.002" pre-expansion and range from 0.0005" to 0.002" post-expansion. Membrane 160 thickness can vary along the length and/or along the circumference of implant 150. Membrane 160 may be a non-porous, solid polymer. Conversely, membrane 160 may be porous, and the pore size may be relatively fixed or variable. It may be desirable to include pores with a size such that blood is not "throttled" into the aneurysm, but rather flows in a "mist" or "cloud" like flow, as shown in reference to FIG. 7 herebelow. To achieve this limited flow, typically pore size ranges from 20 microns to 200 microns when implant 150 is expanded. In some embodiments, pores can be uniformly spaced throughout membrane 160, such as with a distance between adjacent pores ranging from 20 microns to 200 microns when implant 150 is expanded. A detailed description and illustration of a porous membrane is in reference to FIGS. 4A and 16 herebelow. Membrane 160 may be configured as a vehicle for the introduction of therapeutic drugs or other agents, such as agents delivered into an aneurysm to enhance the blockage of blood flow into the aneurysm, to promote healing, or to otherwise improve the overall benefit of implant 150 placement. For example, one or more drugs, reagents and/or other agents can be coated onto a surface of implant 150, mixed, embedded, or covalently bonded with polymeric materials that are coated onto the surfaces of implant 150. In some embodiments, one or more drugs and/or other agents can be loaded into a suitable polymer vehicle that can then be bonded to the polymeric coating, e.g. membrane 160, on implant 150. In some embodiments, membrane 160 can comprise the polymer comprising one or more drugs and/or other agents. In some embodiments, the polymer comprises a dendrimer-type polymer which can be described as a macromolecule, where the dendrimer-type polymer can comprise one or more drugs and/or other agents configured to diffuse from the polymer over a period of time, for example a time period matching the time course of restenosis, such as at least four weeks and up to one year. Non-limiting examples of drugs and/or other agents include: anti-proliferative agents; anti-inflammatory agents; cell regeneration promoting agents; nanoparticles; drug-eluting nanoparticles; nanoparticle gels; and/or restenosis inhibiting agents. The polymer coating can be configured for controlled and long-term drug and/or reagent delivery to the vessel.

In some embodiments, frame 158 and membrane 160 comprise a single, self-supporting structure, such as a polymer tube (e.g. without including a metal frame). The tubular structure may comprise a polymer selected from the group consisting of: fluoropolymers, polyimides, silicones, polyurethanes, polyurethanes ethers, polyurethane esters, polyurethane polycarbonate, polyurethane ureas, mixtures and copolymers thereof, and combinations of these.

In some embodiments, membrane 160 comprises a polymer or group of polymers, such as the material BioSpan® 2F, developed by Polymer Technology Group of Berkeley, Calif., USA. BioSpan® 2F Segmented Polyurethane is a polytetramethyleneoxide-based aromatic polyurethaneurea with mixed aliphatic and cycloaliphatic diamine chain extender. BioSpan® 2F includes Surface-Modifying End Groups (SME™), which are surface-active oligomers covalently bonded to the base polymer during synthesis. In some embodiments, membrane 160 may comprise BioSpan® F, also developed by Polymer Technology Group of Berkeley, Calif., USA. BioSpan® F is a segmented polyurethane with fluorocarbon as surface modifying endgroups. Additional examples of a polymer material includes: a biodegradable polylactide; a polyether; a polyethylene glycol (biostable); a poly(DL-lactide-co-caprolactone) (PLC); a poly(DL-lactide-co-glycolide) (PLGA) (typically biodegradable); a polyether of varying composition and molecular weight; a polyester; a polycarbonate diol; a copolymer of these; and combinations of these. In some embodiments, the polymer material has a molecular weight ranging from MW 100-2000. The polymer can comprise at least one chain extender comprising one or more diols or multi-functional group comprising one or more bioactive surface modifying groups. Non-limiting examples of chain extenders include: methylene diisocyanate; toluene diisocyanate; hexamethylenediisocyanate; diisocyanates; alkyl-triols such as glycerol and increasing molecular weight analogs; triamines; orthoformic acid; phosphates such as Inositol trisphosphate; Calcitriol; cyclic polyols (Cyclitols); Ciceritol; short chain functionalized amino acids; polyketides characterized by three hydroxyl groups such as Tautomycin; lipidoid C12-200; fluoroalkane; fluoroalkanols; and combinations of these. In some embodiments, the polymer can comprise at least one end group that can be functionalized prior to incorporation into the polymer. In some embodiments, the polymer can comprise a reactively functionalized polymer including: an allyl-alkyl hydroxide and amine; a siloxy-containing reactive functionalities; a poly methyoxy and polyethyoxy low molecular weight complex; and combinations of these. The polymers described herein can be configured as nanoparticles; self encapsulating particles (e.g. for multiple drug delivery systems); coatings for stents such as stent 150, 150' and/or 250 described herein, catheters, or other medical devices; and combinations of these. The inclusion of drugs and/or other agents in polymers as described herein is known to those of skill in the art.

The polymers described herein can be made to include radio-lucent or radio-opaque properties by various methods including the addition of a halogen such as bromine or iodine; a ceramic; a metal such as stainless steel, gold, silver or platinum as non-limiting examples; and combinations of these. In some embodiments, gels and/or gel-sols containing these materials, e.g. as nanoparticles, can be embedded in the polymer and/or combined onto the surface in sufficient concentration. Additionally or alternatively, one or more markers can be placed along implant 150 and/or delivery device 100 as described herein.

System 10 includes delivery device 100. Delivery device 100 comprises an interventional catheter construction including shaft 101 and shaft 102. Shaft 101 includes lumen 103, and shaft 102 includes lumen 104. Lumen 104 exits through a side wall of shaft 101 at port 118. Lumen 103 is in fluid communication with an inflatable element, balloon 114. Port 117, typically a luer connector, provides fluid communication to lumen 103, such as to inflate balloon 114 with gas or liquid, typically a 50/50% saline/contrast mixture. Port 118 is positioned in a distal portion of device 100, and is sized and constructed to allow a guidewire, not shown but typically a 0.014" guidewire, to enter the side of shaft 101, and travel through lumen 104 of shaft 102, exiting the distal tip 105 of device 100 (i.e. a rapid exchange guidewire configuration). In an alternate embodiment, device 100 is an over-the-wire system, such that a guidewire can be introduced through port 117 on the proximal end of device 100 and exit distal tip 105. All or a portion of shaft 101, shaft 102 and balloon 114 may be lubricous and/or include a lubricious coating such as a hydrophilic coating. In one embodiment, the distal portion of device 100 is formed of more flexible materials than that of the mid and proximal portions of device 100. The more flexible distal portion may comprise a length sufficient to navigate through particular vessel tortuousity, such as the tortuousity in vessels proximate the brain, while the stiffer mid and proximal portions of device 100 provide column support sufficient for advancement of device 100 to the desired locations. For example, the length of a more flexible distal portion of device 100 may range from 32 cm to 38 cm, typically 36 cm.

Delivery device 100 may include one or more markers, such as a marker selected from the group consisting of: radiopaque markers such as markers that can be viewed with X-ray or fluoroscopy; visible markers such as markers that can be viewed with a visible intraluminal camera; infrared markers such as markers that can be viewed with an infrared intraluminal camera; ultrasound markers such as markers that can be viewed with external ultrasound or intravascular ultrasound; magnetic markers such as markers that can be viewed with MRI; and combinations of these. In the illustrated embodiment, shaft 102 includes two markers 159a and 159b where marker 159a is positioned on shaft 102 correlating to a proximal portion of balloon 114 and/or implant 150 and marker 159b is positioned on shaft 102 correlating to a distal portion of balloon 114 and/or implant 150.

Shaft 101 may comprise multiple layers, such as two layers comprising a co-extrusion of Pebax™ 55D and HDPE. Shaft 102 may comprise multiple layers as well, such as two equally thick layers of nylon, for example Grilamid nylon. Shafts 101 and/or 102 may comprise a ribbon coil, such as is described in reference to FIG. 10 herebelow, such as to reinforce lumens 103 and/or 104 respectively, allowing construction of shafts 101 and/or 102 with softer materials. For example, shaft 101 may include a ribbon coil or other reinforcing coil and may be constructed of materials with a durometer ranging from 32D to 72D, and preferably of materials with a durometer of approximately 55D. Shaft 102 may include a ribbon or other reinforcing coil, and may be constructed of materials with a durometer ranging from 40D to 72D, and preferably of materials with a durometer of approximately 62D. The inner walls of shafts 101 and/or 102, defining lumens 103 and 104, respectively, may comprise PTFE and/or include a PTFE liner, such as to improve transport of fluids or devices through the lumens.

System 10 can further include a guide catheter, not shown, but typically a 6F (0.070" ID) guide catheter employed to introduce delivery device 100 into a vessel.

Figure 12:
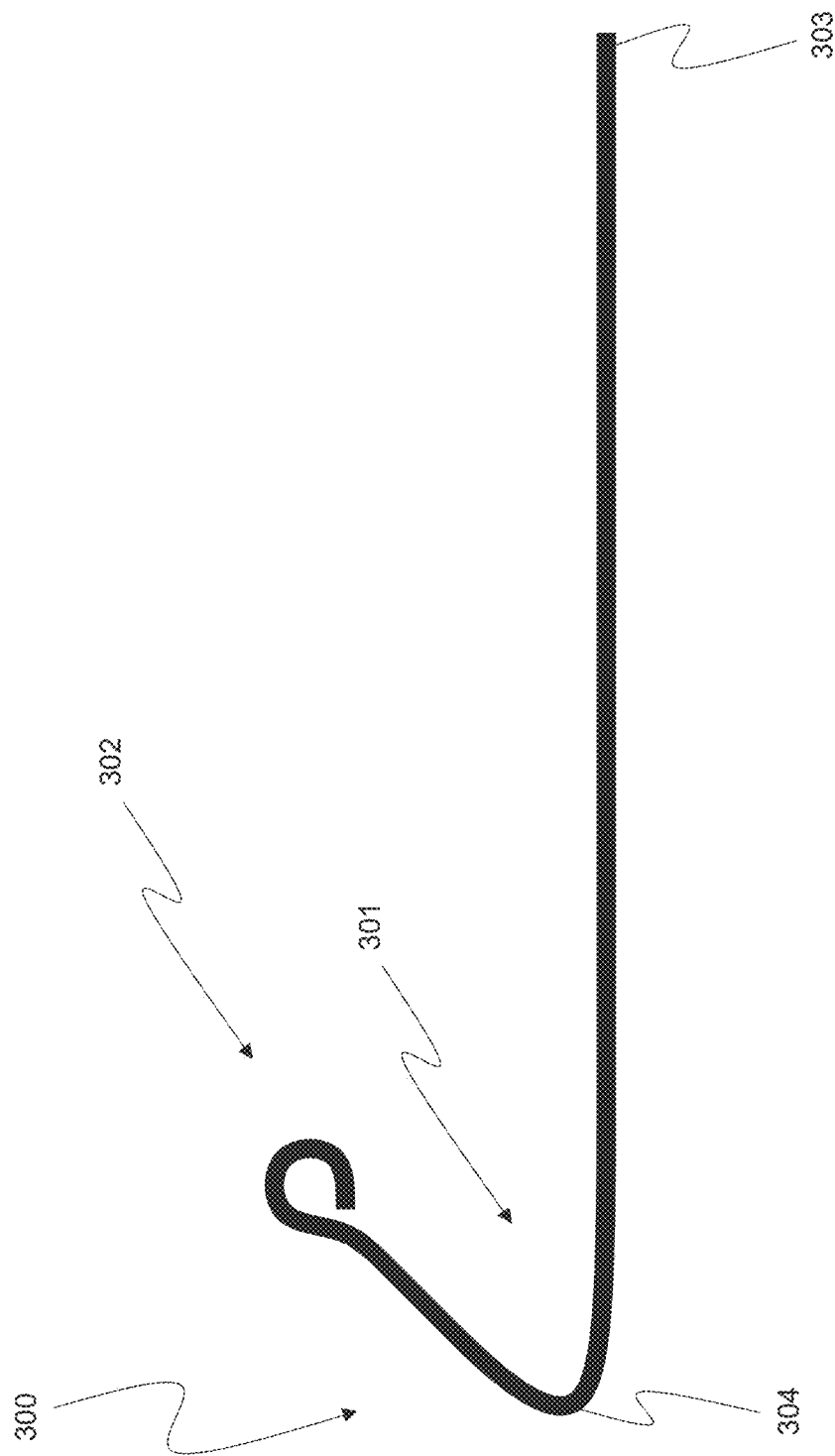
FIG. 12 illustrates a shaped mandrel including a curved portion, consistent with embodiments of the present disclosure.

System 10 may include a shaped mandrel, shown and described in reference to FIG. 12 herebelow. The shaped mandrel, which may include a curved portion, can be used in a preparatory step which includes inserting the shaped mandrel into lumen of device 100. In one embodiment, implant 150 is tracked back and forth over the mandrel curved portion, such as to relieve stresses and/or otherwise improve trackability of device 100 over a vessel-inserted guidewire.

Balloon 114 is configured to expand implant 150 radially outward from a first radially compact position to a second, expanded position, where the expanded position is shown in FIG. 1. In an alternative embodiment, implant 150 is allowed to self-expand, as is described in reference to FIG. 15 herebelow, with or without the assistance of balloon 114. In some embodiments, balloon 114 is attached to the distal portion of shaft 102 having a working length of approximately 1 mm to 3 mm longer than the length of implant 150. In some embodiments, the combined lengths of shafts 101 and 102, the working length of delivery device 100, is at least 140 cm long, and more typically 145 cm long. Balloon 114 expands from the compacted position to the expanded position at a given pressure such that the diameter of implant 150 in its expanded position is controlled. In some embodiments, the controlled diameter ranges from 2.0 mm to 5.0 mm, i.e. the diameter of the vessel implant 150 is to be inserted. In this embodiment, the opening pressure, i.e. pressure at which implant 150 is fully open, ranges from 3.5 atm to 6.0 atm, and the rated burst pressure of balloon 114, i.e. maximum pressure, ranges from 10 atm to 20 Btm. In some embodiments, implant 150 can be over-expanded such that one or more inner diameters of implant 150 matches that of the vessel inner diameter (e.g. the inner diameter of the majority of the length of implant 150 matches that of the corresponding vessel inner diameter).

Balloon 114 can include at least one fold. In one embodiment, balloon 114 can be a 3-fold balloon. In another embodiment, balloon 114 can be a 5-fold balloon. In yet another embodiment, balloon 114 can be a 6-fold balloon. By increasing the amount of folds in balloon 114, it will decrease the profile and assist in the removal of balloon 114 from implant 150 after deployment, especially in tortuous anatomy. In yet another embodiment, balloon 114 can be a spiral-fold balloon, also decreasing the balloon profile. Specifically, when a spiral is pulled, it reduces in diameter, thus assisting in the removal from implant 150 when in tortuous anatomy. Exemplary balloon 114 configurations are shown in detail in FIGS. 6A-6D herebelow.

Balloon 114 may be formed of suitable materials such as: irradiated polyethylene; polyethylene terephthalate; polyvinylchloride; nylon such as Nylon-12 L2140, L25, L2125, and L2101; and copolymer nylons, such as Pebax™; and combinations of these.

Balloon 114 can include at least one marker, not shown, but for example, a distal marker and a proximal marker selected from the group consisting of: radiopaque markers such as markers that can be viewed with X-ray or fluoroscopy; visible markers such as markers that can be viewed with a visible intraluminal camera; infrared markers such as markers that can be viewed with an infrared intraluminal camera; ultrasound markers such as markers that can be viewed with external ultrasound or intravascular ultrasound; magnetic markers such as markers that can be viewed with MRI; and combinations of these. In one embodiment, balloon 114 includes two markers where the distance between the first marker and a distal end of implant 150 and the distance between the second marker and a proximal end of the implant 150 ranges from 0.5 mm to 1.5 mm, and preferably 0.5 mm. System 10 may be provided with a choice of lengths of implant 150. In one embodiment, system 10 is provided with four lengths of implant 150, termed herein as short, moderate, long and extra-long. In the case of the short implant, implant 150 is approximately 15.0 mm long and the space between the inside edges of the first and second marker of delivery system 100, i.e. balloon 114 marker spacing, is approximately 18 mm, with a minimum of approximately 17.5 mm. In the case of the moderate implant, implant 150 is approximately 20.0 mm long and the balloon 114 marker spacing is approximately 23.5 mm, with a minimum of 23.0 mm. In the case of the long implant, implant 150 is approximately 25.0 mm long and the balloon 114 marker spacing is approximately 28.5 mm, with a minimum of approximately 28.0 mm. In the case of the extra-long implant, implant 150 is approximately 30.0 mm long and the balloon 114 marker spacing is approximately 33.5 mm with a minimum of approximately 33.0 mm. One exemplary purpose of the balloon markers is to identify the working length of balloon 114, where the marker spacing is selected based upon the size of implant 150 to prevent the ends of implant 150 from flaring, thus minimizing the risk of implant 150 being delivered prior to the desired placement in a vessel.

In one embodiment, system 10 includes a distal portion with a cross-sectional profile that ranges from 0.045" to 0.060", such as to be inserted into a guide catheter, not shown, but typically a 6F guide catheter having an inner diameter of 0.070".

Figure 2A:
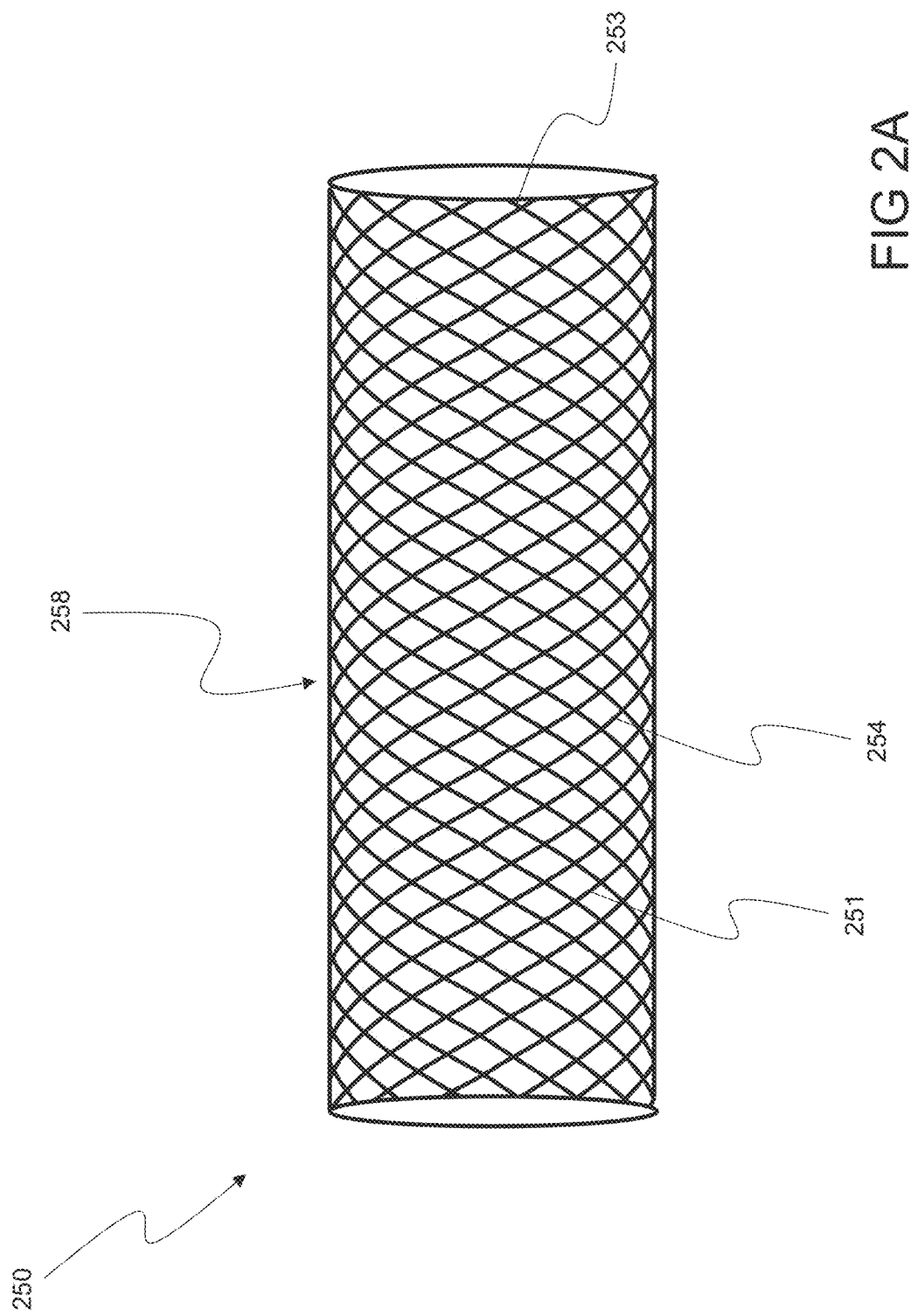
Figure 2B:
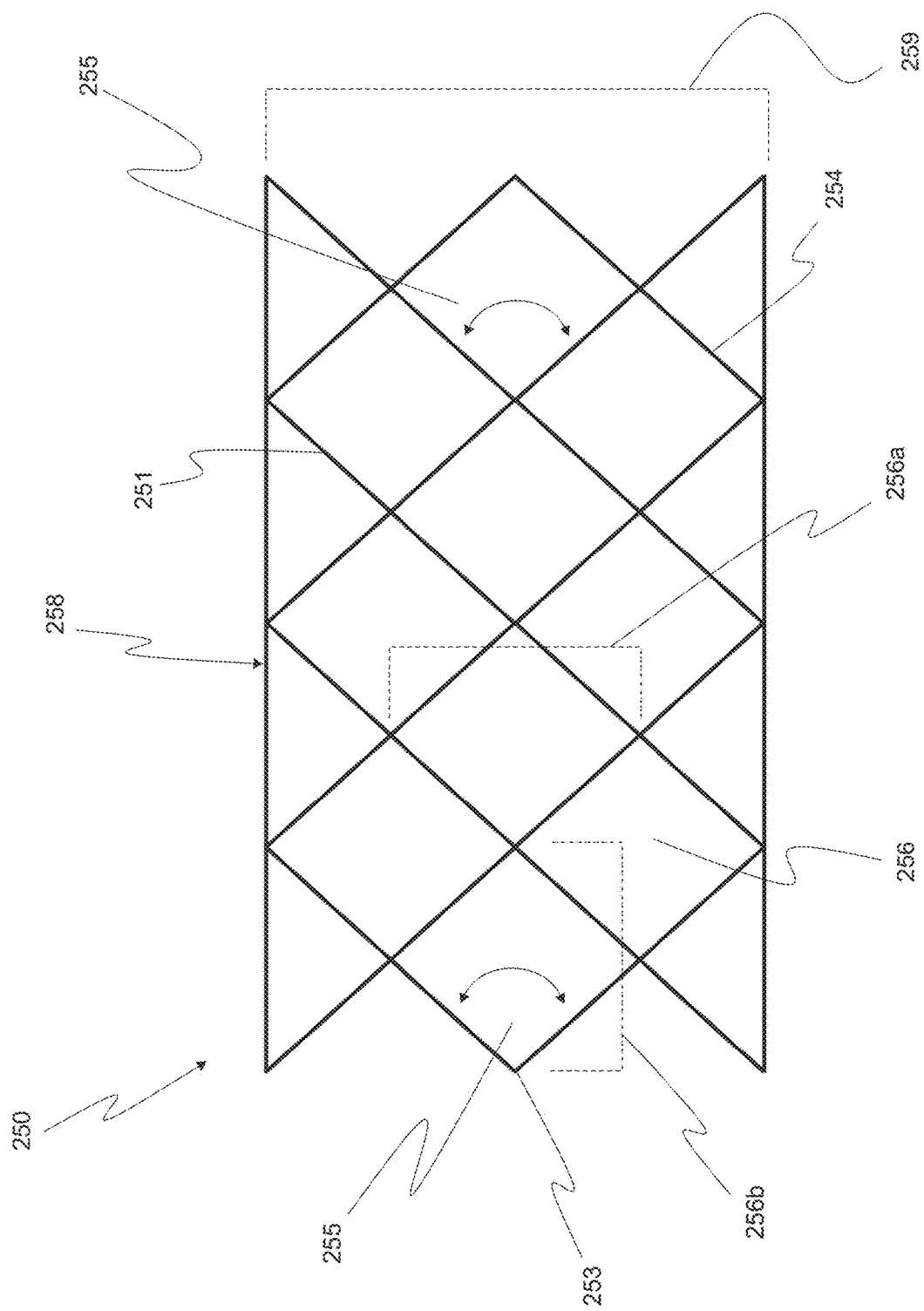

FIGS. 2A and 2B illustrate a self-expanding implant that is made of wires. Implant 250 includes frame 258 with braided pattern shown and including struts 251 with welded ends 253. In some embodiments, ends 253 are not welded, but are encapsulated in a polymer coating, for example, the polymer coating described with reference to FIG. 1 herein, to ensure ends 253 contain no sharp edges and are otherwise atraumatic to a vessel wall. Implant 250 is designed such that it has a smaller profile as compared to balloon-expandable (i.e. plastically deformable) implants. Implant 250 is relatively flexible along its longitudinal axis to facilitate delivery through tortuous body lumens, but when expanded transitions to a radial stiffness sufficient to maintain patency of a body lumen, such as a blood vessel. Implant 250 may include a polymer coating covering at least a portion of implant 250, as described in FIG. 1 hereabove. Additionally or alternatively, implant 250 may include a membrane, such as membrane 160 described in reference to FIG. 1 hereabove. A delivery device configured for delivery of a self-expanding implant, such as the sheathed delivery device 100' described in reference to FIG. 15 herebelow, can be used to deliver implant 250.

Various design attributes can be selected such that self-expanding implant 250 demonstrates the desired flexibility and compliance, for example attributes including but not limited to: the number of wires; braiding angle; weave configuration; and combinations of these. By selecting the appropriate design attribute ranges and combinations, implant 250 resists ovalization and kinking in tortuous body lumens, provides the desired radial force when deployed, and provides the proper support to a polymer coating and/or membrane.

In the embodiment illustrated in FIG. 2B, implant 250 comprises an eight-wire configuration. However, any number of wires may be used, for example up to 48 wires, but typically 8 to 14 wires. Generally, as the number of wires 254 increase, the stiffness of the braid increases, and the effective area available to optimize and modify pores decreases. In one embodiment, wire 254 can be one or more metals. In another embodiment, wire 254 can be one or more shape memory polymers or shape memory alloys, for example, a 0.003" Nitinol wire. In yet another embodiment, wire 254 can be a composite wire comprising a radiopaque element and/or a superelastic shape memory material. In the case of a composite wire, wire 254 can be a drawn filled tube such as a drawn filled tube created by: heating an outer tube; drawing the outer tube over an inner core; lowering the temperature of the outer tube; causing the outer tube to contract, compress, and fuse to the inner core. The outer tube can be a radiopaque material, such as Platinum/Tungsten, fused with a deformation resistant material, such as Nitinol. Additionally or alternatively, the outer tube can be Nitinol fused with a Platinum/Tungsten inner core. Preferably, based upon the selected inner and outer core materials, the resulting implant displays radiopaque and/or deformation resistant properties. Alternative metals, polymers and/or encapsulated metals and polymers may be used for wire 254, for example: stainless steel; Cobalt Chromium such as encapsulated Cobalt Chromium; encapsulated materials; and combinations of these. In a typical embodiment, the diameter of wire 254 ranges from 0.0005" to 0.004", and more typically, 0.003".

Also illustrated in FIG. 2B, implant 250 includes multiple braid angles, such as braid angle 255, illustrated here at 90°. Braid angle 255 defines the angle that exists between two wires 254 that are wound in opposite directions, parallel with the linear axis of the braid. Braid angle 255 is related to device flexibility and the resistance to folding of a polymer and/or membrane along the inside edges of implant 250, such as when placed in a tight curvature of a body lumen. Braid angle 255 may range from 1° to 179°, typically ranging from 80° to 145°, and more typically a braid angle approximating 90°, 125° or 135°. In one embodiment, braid angle 255 remains constant throughout implant 250. Additionally or alternatively, implant 250 can include varying or multiple braid angles 255. A smaller braid angle, causes wires 254 to straighten such that implant 250 is biased toward a near linear shape, as compared to a larger braid angle, such as a 135° braid angle. As the braid angle 255 approaches approximately 180°, the flexibility of the device is increased, however each wire 254 is more closely positioned to each sequential wire 254, such as would be observed in a closed wound coil. This closely spaced configuration results in an increased risk of occluding sidebranches on the inside edges of the vessel. When the braid angle is approximately 135°, the wires 254 have sufficient spacing relative to each other, such as on the inside edge of a curve, to minimize the risk of the sidebranches being completely covered by sequential wires and/or insufficient wire spacing, thus maximizing the chance of sidebranch patency. Further, a smaller braid angle 255 results in a decreased elongation and stretching of a polymer coating and/or a surrounding membrane when implant 250 is collapsed prior to delivery, such as when implant 250 is in a delivery device, for example, delivery device 100' described in reference to FIG. 15 herebelow. Accordingly, a lower frictional force is exerted on the delivery device during delivery, resulting in implant 250 deploying gently, causing less trauma on a vessel wall. Still further, a smaller braid angle has less radial strength, thus conforming to pulsating systolic/diastolic phases and vessel wall movement. The braid angle may be determined based on the number of wires 254, the diameter of implant 250, and/or the braid pitch, each of which cooperate to achieve the desired implant properties.

Weave configuration also contributes to the flexibility and deformation resistance of implant 250. In the embodiment illustrated in FIGS. 2A and 2B, wires 254 are woven, or braided, in a one-over-one-under configuration, meaning one wire is placed above one wire and under the sequential wire. Additionally or alternatively, one-over-two-under and two-over-two under configurations can be used. In the case of one-over-one-under, wires 254, typically in an eight to fourteen wire configuration, create relatively larger diamond cells 256 with increased overall flexibility of implant 250. When implant 250 in this configuration is placed to treat an aneurysm, the surface area of a surrounding membrane is greater across the surface of the aneurysm, while the surface area of frame 258 decreases across the aneurysm. As shown, braid angle 255 is 90°, such that diamond cell height 256a and width 256b are approximately the same, 0.13 mm. Accordingly, as braid angle 255 increases, diamond cell height 256a increases and diamond cell width 256b decreases. Typical diamond cell widths range from 0.00 mm to 0.26 mm, and more typically from 0.053 mm and 0.15 mm.

Typically, implant 250 outer diameter 259 ranges from 1.5 mm to 5.0 mm, and implant 250 length ranges from 7.0 mm to 40.0 mm. However, the braided design of frame 258 enables implant 250 to be cut to any desired length, such as when 258 is cut by a clinician, in a sterile setting, during a clinical implant procedure.

The design parameters and materials discussed above may be selected and combined such that the resulting implant displays the desired flexibility and deformation resistance.

FIGS. 2C-G illustrate various exemplary embodiments of self-expanding implant 250 made of wires, consistent with the concepts disclosed in FIGS. 2A and 2B. Implant 250 of each of FIGS. 2C-G can include the wire pattern as shown in the associated drawing. In some embodiments, implant 150 of FIGS. 2C-G are plastically deformable and/or include plastically deformable sections, such as can be expanded by an internal balloon.

Figure 3A:
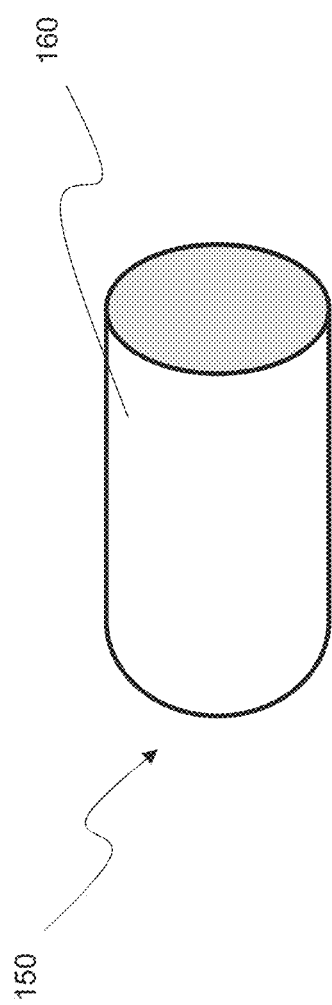
FIGS. 3A, 3B, and 3C illustrate an implant including a membrane covering various portions of the implant, consistent with embodiments of the present disclosure.
Figure 3B:
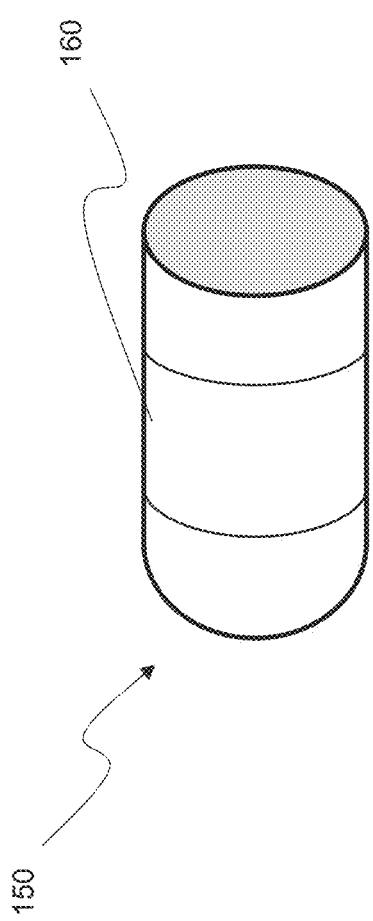
Figure 3C:
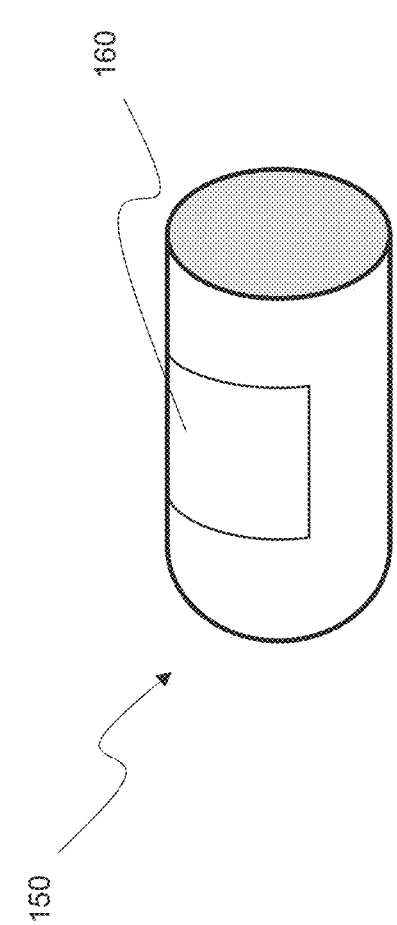

FIGS. 3A through 3C illustrate an implant including a membrane covering various portions of the implant. As shown in FIG. 3A-3C, membrane 160 is shown completely covering implant 150, covering a full circumferential partial length of implant 150, and covering a partial circumferential partial length of implant 150, respectively. Membrane 160 expands radially with implant 150 and is configured to minimally restrict and minimally alter the expansion characteristics of implant 150. For example, membrane 160 has a minimum effect on the mechanical properties of implant 150 such as flexibility, trackability, expandability, recoil, and/or shortening. Membrane 160 may be configured to expand up to 1000%. In a typical embodiment, membrane 160 expands up to approximately 140%. Membrane 160 comprises materials that are stable in normal shelf life conditions as well as being stable during and subsequent to sterilization (e.g. EtO sterilization). Membrane 160 is prevented from sticking to a balloon material (e.g. a nylon balloon material), such as preventing sticking otherwise caused by crimping of implant 150 onto a balloon, for example, balloon 114 described in reference to FIG. 1 hereabove, sticking caused during manufacturing, sticking caused after a sterilization process and/or after a period of time between sterilization and ultimate use. Membrane 160 is able to tolerate temperature variations of up to 60° C. The edges of membrane 160 are aesthetically acceptable, and have smooth, not rough edges. Also, membrane 160 may be non-porous or porous and include therapeutic drugs, reagents and/or other agents as described in detail in FIG. 1 hereabove.

FIGS. 4A through 4C illustrate an implant including various coverings. FIG. 4A illustrates implant 150 including a permeable membrane 160 including pores 161 and spaces 162. Typically, pore size ranges from 20 microns to 200 microns. Further, pores 161 can be uniformly spaced throughout membrane 160 with a pore spacing 162, i.e. distance between adjacent pores, ranging from 20 microns to 200 microns. In one embodiment, pores 161 are created by drilling holes into a solid film. In some embodiments, pores 161 have an initial diameter that expands to a final diameter, for example, pores 161 can be drilled such that pore size is initially approximately 20 microns to 50 microns and expands to a final diameter of approximately 80 microns to 100 microns. In alternate embodiments, pore size does not expand from the initial size, in other words, pores 161 are drilled to a final diameter, such as a final diameter of between 20 microns and 200 microns, typically at a final diameter of approximately 100 microns. In some embodiments, pore 161 size can vary along the length and/or about a circumference of implant 150, for example, pores 161 may have a smaller diameter at a mid portion of implant 150 and a larger diameter at the proximal and distal portions of implant 150. Pores 161 may include various geometric shapes, for example, round; elliptical; rectangular; trapezoidal; triangular; and combinations of these. In one embodiment, pores 161 are manufactured as round holes, such that as implant 150 transitions from an unexpanded state to an expanded state pores 161 transition from round to elliptical geometries. Alternatively or additionally, one or more pores 161 may be manufactured as an elliptical holes, such that as implant 150 transitions from an unexpanded state to an expanded state these one or more pores 161 transition from an elliptical shape to a round or different elliptical shape. One or more pores 161 can be positioned (e.g. drilled) such that there is little to no contact with struts 151 of implant 150.

FIG. 4B illustrates implant 150 including polymer strips 163. Strips 163 can be wrapped circumferentially around implant 150, as shown, and interlaced above and below the struts of implant 150. Typically, strips 163 are less than 0.075 mm wide, and the distance between adjacent strips is typically less than 100 microns. Alternatively or additionally, polymer strips 163 can be arranged longitudinally about implant 150.

FIG. 4C illustrates implant 150 including woven polymer mesh 164. Woven mesh 164 can be formed from a sheet and wrapped around implant 150. The mesh size of the sheet is approximately 0.025 mm to 0.050 mm, while the thickness of the polymer is less than 100 microns.

The polymer used to create the coverings illustrated in FIGS. 4A-4C may be selected from the group consisting of: fluoropolymers, polyimides, silicones, polyurethanes, polyurethanes ethers, polyurethane esters, polyurethane polycarbonate, polyurethane ureas, mixtures and copolymers thereof, and combinations thereof.

Figure 5A:
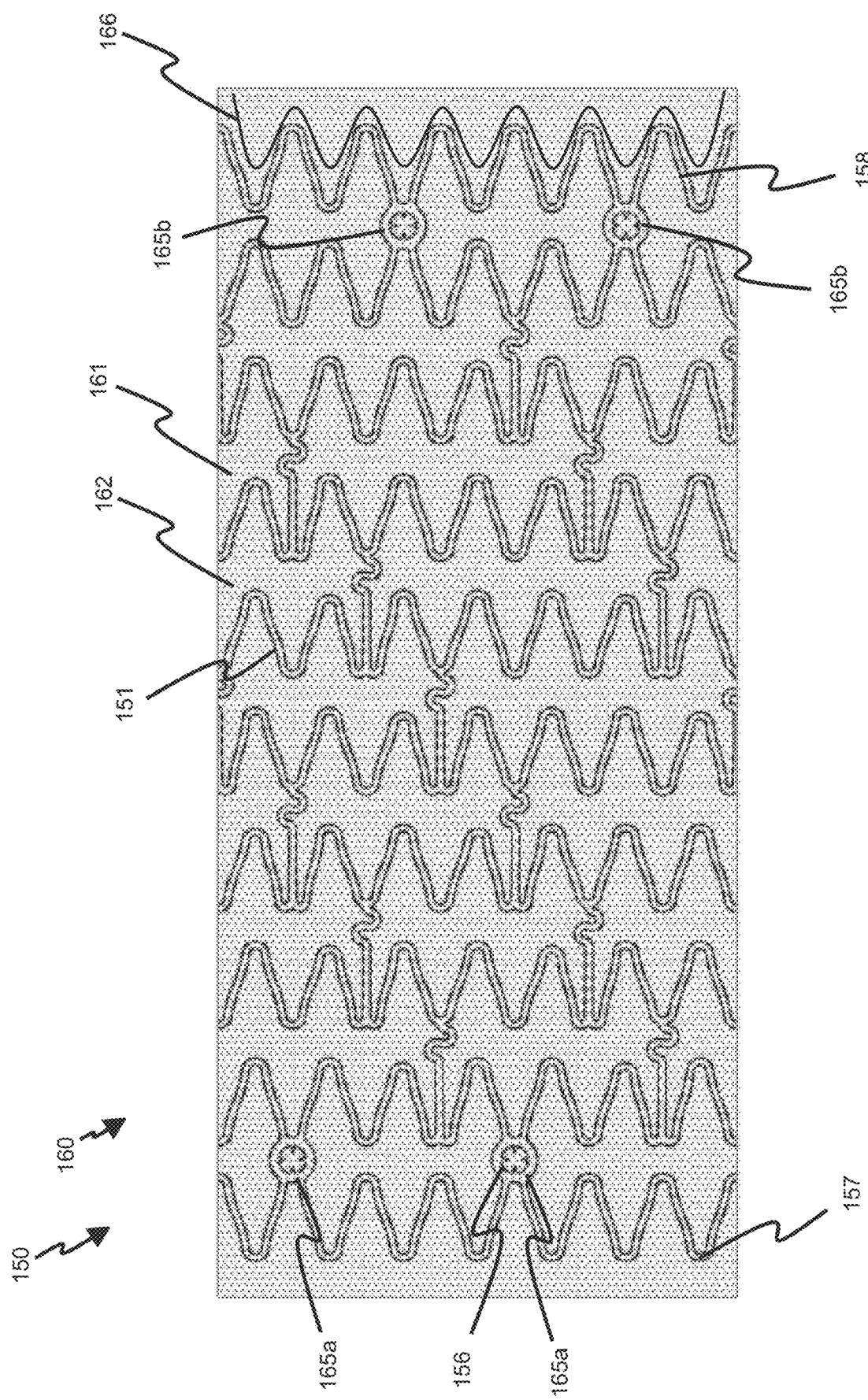
FIG. 5A illustrates an implant including a membrane, shown in an unrolled state to more clearly show the configuration of the implant elements, consistent with embodiments of the present disclosure.
Figure 5B:
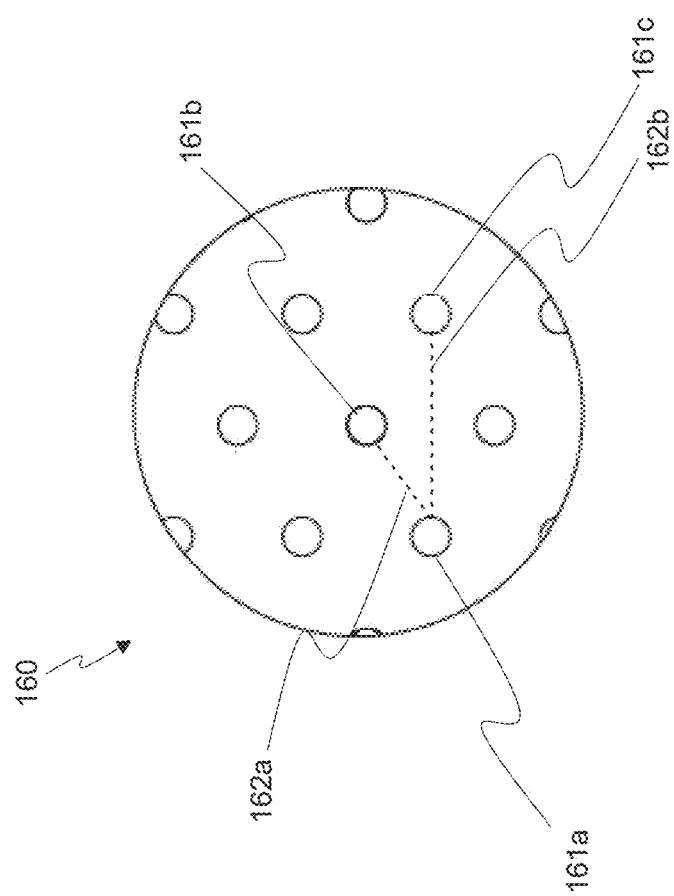
FIG. 5B illustrates a detailed view of a portion of the membrane of FIG. 5A, consistent with embodiments of the present disclosure.

FIG. 5A illustrates an implant including a membrane, shown in an unrolled state to more clearly show the configuration of the implant elements, consistent with embodiments of the present disclosure. FIG. 5B illustrates a detailed view of the membrane of FIG. 5A. Preferably, implant 150 is an initially solid tubular member, defining a longitudinal axis and a circumference. The walls of the tubular member are selectively removed by high precision cutting, e.g. laser cutting, chemical etching, water jet cutting, or standard tool machining, to provide frame 158 which includes struts 151. Additionally or alternatively, frame 158 may be formed from a flat sheet of material that is rolled and fused along two edges. Frame 158, as shown, includes seven bend points 157 along each circumferential segment as shown. Frame 158 can include a number of bend points along each circumferential segment, such as is required to achieve the desired frame size and characteristics, for example, in some embodiments, frame 158 includes six bend points 157.

In the illustrated embodiment, frame 158 is covered by permeable membrane 160 which includes pores 161 and spaces 162. Typically, pore 161 sizes ranges from 20 microns to 200 microns (e.g. a 20 micron to 200 micron diameter or equivalent diameter). Further, pores 161 can be uniformly spaced throughout membrane 160 with a pore spacing 162, i.e. distance between the edges of adjacent pores, typically ranging from 20 microns to 200 microns. Pores 161 may be created by drilling or otherwise forming holes into a solid film. In some embodiments, pores 161 have an initial diameter that expands to a final diameter, for example, pores 161 can be drilled such that pore size is approximately 20 microns and expand to a final diameter of 100 microns. In alternate embodiments, pore size does not expand from the initial size, in other words, pores 161 are manufactured to a final diameter. Pores 161 may be various geometric shapes, for example, circular; elliptical; rectangular; triangular; trapezoidal, and combinations of these.

Subsequent to covering frame 158 with membrane 160, membrane 160 can be trimmed, for example, manually, along trim line 166. In one embodiment, the distance between trim line 166 and frame 158 ranges from 10 microns to 15 microns, typically approximately 12 microns. In some embodiments, proximal rings 165a and distal rings 165b do not include membrane 160, allowing distal and proximal ends of implant 150 to expand further, such as to ensure better adaptation to a vessel wall. Additionally, rings 165a and 165b, without polymer, can provide anchoring or other retention forces between implant 150 and the vessel wall. In the illustrated embodiment, rings 165a and 165b can include teeth 156 configured to secure a marker in place, marker not shown but typically a radiopaque marker.

As shown in FIG. 5B, the distance between adjacent pores is characterized by a first bridge distance 162a and a second bridge distance 162b. The first bridge distance 162a defines the distance from the edge of pore 161a to the edge of adjacent pore 161b. The second bridge distance 162b defines the distance from the edge of pore 161a to the edge of adjacent pore 161c. In one embodiment, each pore and its respective first bridge distance is equal throughout membrane 160. In an alternate embodiment, each pore and its respective first bridge distance is not equal throughout membrane 160, for example, to achieve a membrane with a non-uniform porosity. Similarly, each pore and its respective second bridge distance may be equal or not equal throughout membrane 160. In one embodiment, the first bridge distance 162a can be equal to the second bridge distance 162b. In another embodiment, the second bridge distance 162b is greater than the first bridge distance 162a. In one non-limiting example, the first bridge distance 162a is approximately 70 microns, and the second bridge distance 162b is approximately 100 microns. In another non-limiting example, the first bridge distance 162a is approximately 70 microns, and the second bridge 162b distance is approximately 140 microns.

Implant 150 can be balloon expandable, self-expanding, or include both balloon expandable and self-expanding portions, as described herein. Further, implant 150 can be implanted and expanded via delivery device, for example delivery device 100 described herein. A secondary expansion device, such as a second balloon device, may be used to modify the placement of (e.g. to further expand) implant 150.

Figure 6B:
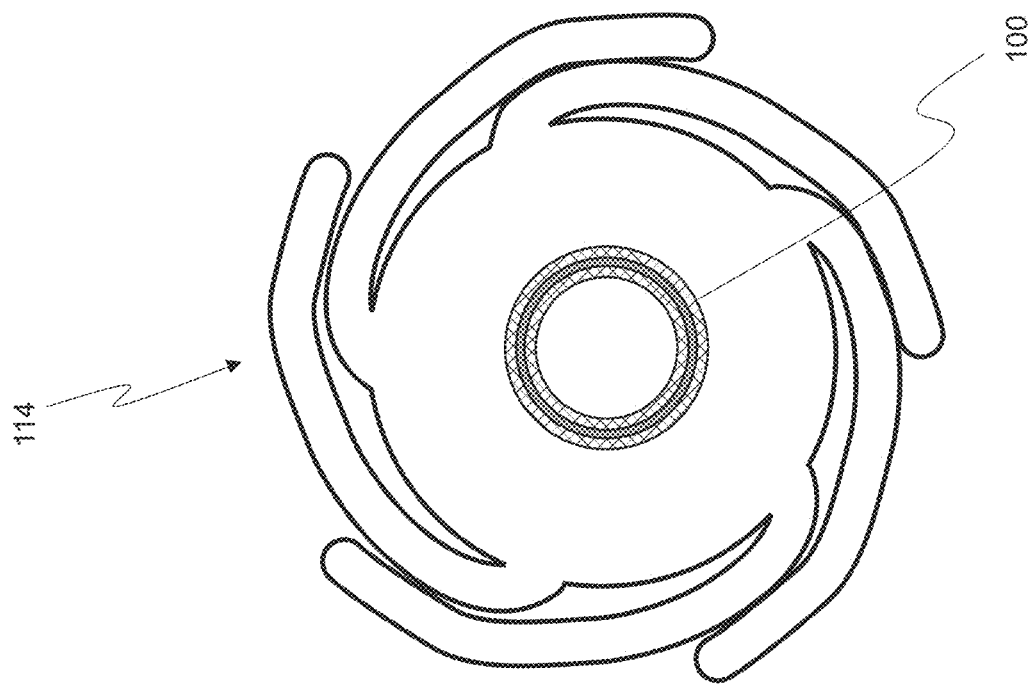
FIGS. 6A, 6B, 6C, and 6D illustrate various balloon configurations used to expand an implant, consistent with embodiments of the present disclosure.
Figure 6A:
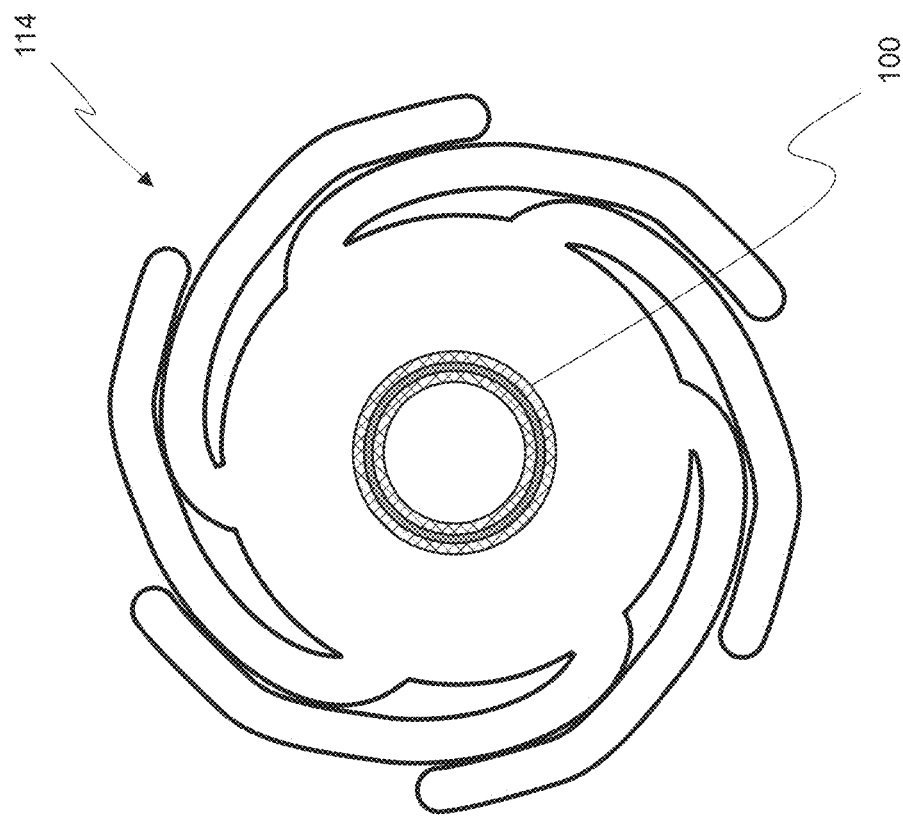
Figure 6D:
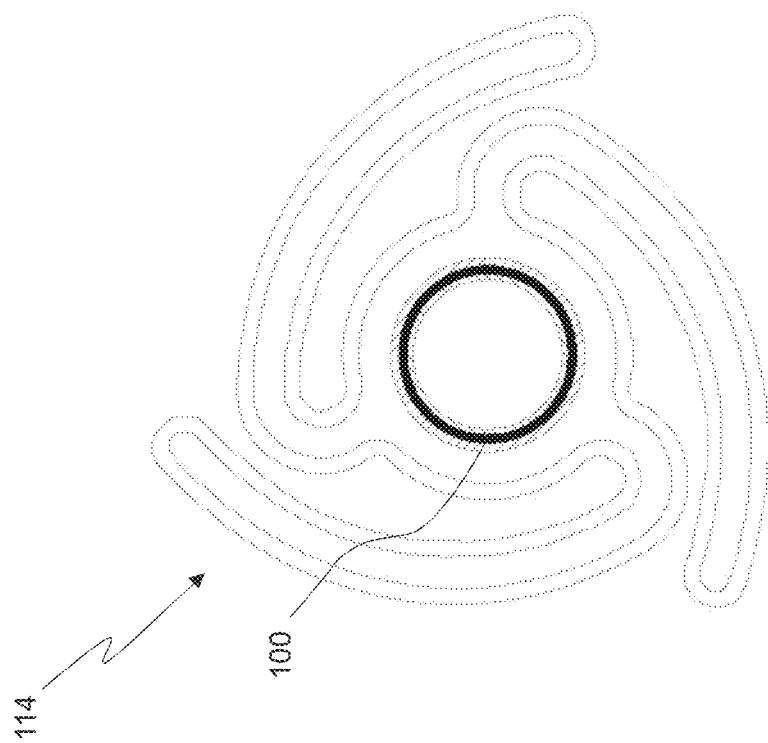
Figure 6C:
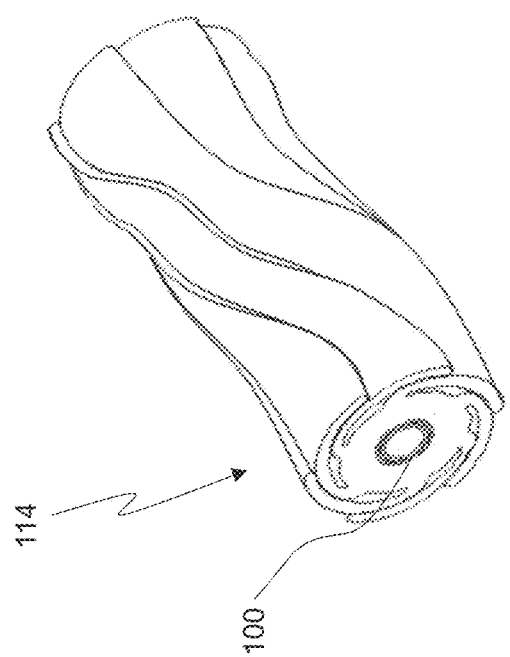

FIGS. 6A through 6D illustrate various balloon configurations used to expand an implant. FIG. 6A illustrates a 6-fold balloon; FIG. 6B illustrates a 5-fold balloon; FIG. 6C illustrates a spiral-fold balloon; and FIG. 6D illustrates a 3-fold balloon. By increasing the amount of folds in balloon 114, the unexpanded balloon profiles decreases, such as to assist in the removal of the balloon in tortuous anatomy. Similarly, the spiral-fold balloon also decreases balloon 114 profile. For example, when the spiral is pulled, it reduces in diameter, thus assisting in the removal through tortuous anatomy. Also, balloon 114 folds can be oriented such that a user, e.g. a physician, properly refolds balloon 114 by rotating delivery device 100 in a particular direction. Balloon 114 folds can be heat set such that when balloon 114 is deployed, an pre-deployed configuration memory is included in the balloon fold material, for example a resilient bias toward the pre-deployed configuration.

In some embodiments, balloon 114 can include optimized balloon folds, not shown, but result in better refolding of balloon 114 after the associated implant, such as implant 150 of FIG. 1 hereabove, is deployed. The optimized balloon folds assist in removal of balloon 114 after implant 150 deployment and balloon 114 deflation. The optimized folds are achieved by optimizing dies of a balloon folding device and/or the heat set parameters using in the folding of the balloon. Specifically, the balloon fold processing involves first pleating the manufactured (e.g. blown) balloon (e.g. pleating performed for a particular time at a particular temperature), then wrapping the folds (e.g. wrapping performed for a particular time at a particular temperature), and annealing the wrapped balloon (e.g. annealing performed for a particular time at a particular temperature). Desired balloon properties can be achieved by varying these processing parameters, singly or in combination.

Balloon 114 diameter can range from 3.25 mm to 4.5 mm. In some embodiments, balloon 114 includes tapered proximal and distal ends. In some embodiments, the distal and/or proximal taper length is approximately 1.5 mm to 5.0 mm. Balloon 114 taper angle can range from 14° to 67°. Balloon 114 may be formed of suitable materials such as: irradiated polyethylene; polyethylene terephthalate; polyvinylchloride; nylon; and copolymer nylons, such as Pebax™; and combinations thereof. In some embodiments, balloon 114 includes Nylon 12, L2140 which has a high tensile strength, high rated burst pressure and maintains a heat set fold under high inflation pressures, such as 12 atmospheres of pressure. Balloon 114 properties can vary along the length of the balloon. Non-limiting examples of balloon 114 properties include: taper angle, taper length, and wall thickness. Balloon 114 may include more than one taper angle, causing the taper length to shorten, such that balloon 114 is more easily withdrawn after implant placement and balloon 114 deflation. Additionally or alternatively, balloon 114 wall thickness can be greater along the tapered length of balloon 114.

FIG. 7 illustrates the hemodynamics resulting after deployment of an implant, wherein a mist-like flow of blood enters the aneurysm, consistent with embodiments of the present disclosure. As described above, it is desirable for implant 150 to include a membrane with pores of a size such that blood is not "throttled" into the aneurysm, but rather flows in a "mist" or "cloud" like flow. To achieve this restriction of flow, typically, membrane 160 pore sizes range from 20 microns to 200 microns. Further, the pores can be uniformly spaced throughout membrane 160 with a distance between adjacent pores ranging from 20 microns to 200 microns.

Figure 8:
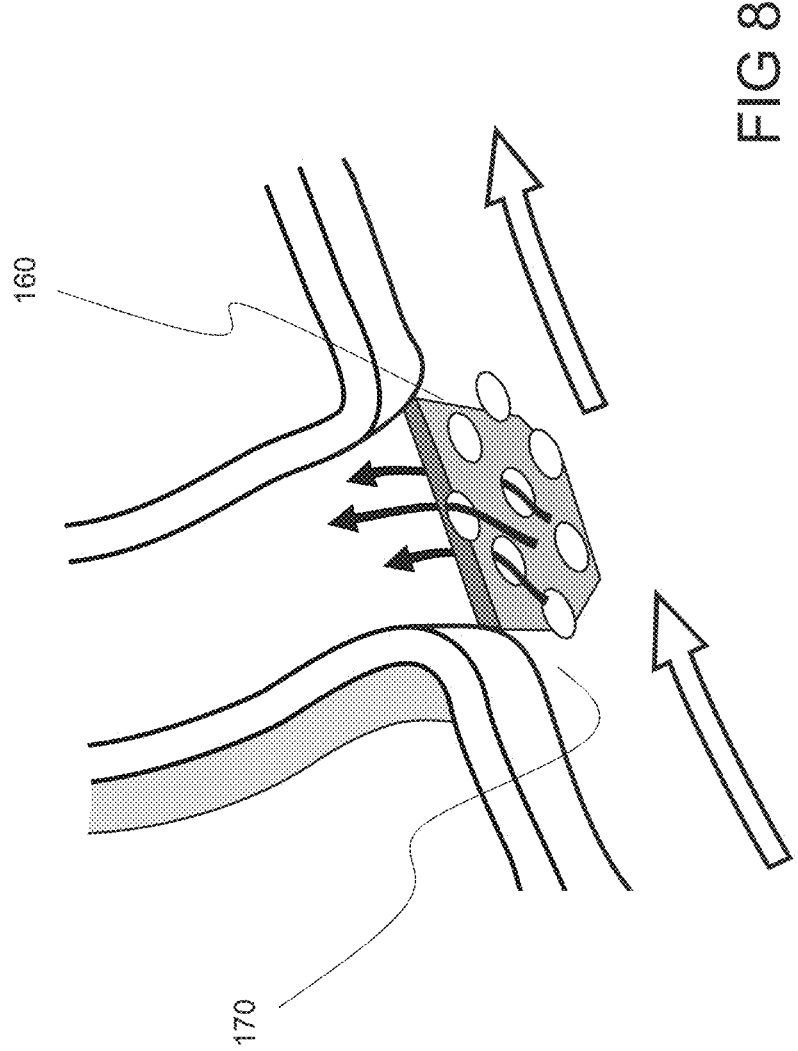
FIG. 8 illustrates the hemodynamics proximate another implanted device, consistent with embodiments of the present disclosure.

FIG. 8 illustrates the hemodynamics after deployment of an implant, wherein turbulent flow to a side branch is minimized, consistent with embodiments of the present disclosure. For purposes of clarity, the implant is removed, and only a portion of membrane 160 is illustrated. Membrane 160 has a thickness such that turbulence into side branches is minimized. In a typical embodiment, membrane 160 thickness ranges from 0.0005" to 0.005", and more typically 0.001". As shown in FIG. 8, angle 170 created by membrane 160 with the vessel wall is related to the thickness of membrane, i.e. the thinner the membrane, the smaller the angle, thus turbulence into the side branches is minimized.

FIG. 9A illustrates an implant after deployment in a vessel proximate an aneurysm. FIG. 9B illustrates a post dilatation balloon further expanding the implant of FIG. 9A. FIG. 9C illustrates the implant of FIG. 9A subsequent to the expansion of FIG. 9B. Implant 150 can be plastically deformed or otherwise expanded, at any time after initial deployment, typically in the same clinical procedure as the implantation or in a second procedure, such as a procedure performed within 1 week or within 6 months of the implantation procedure. The expansion may be performed using a standard or customized balloon catheter device, such as post-dilatation balloon 400 configured to increase the diameter of one or more portions of implant 150, such as to mate the outer surface of implant 150 with the vessel wall (e.g. to eliminate false lumens 401 or other pathways around the external surface of implant 150). In some embodiments, post dilatation balloon 400 is positioned and operated to expand a proximal portion of implant 150 prior to expanding a distal portion of implant 150. An angiography procedure may be performed after this expansion procedure to confirm a lack of blood flow 402 around implant 150 (i.e. blood flow that was present prior to the expansion procedure). If leaks or false lumens 401 are observed to remain, an additional expansion procedure may be performed. Post-dilatation balloon 400 may comprise a length to allow the user to inflate short discrete segments of implant 150, thus minimizing vessel straightening. The length of post-dilatation balloon 400 may be selected such that the balloon is approximately 1 mm or 2 mm longer than the diameter of the largest diameter vessel encountered. In one embodiment, post-dilatation balloon 400 is a 7 mm long balloon to be used in a 5 mm vessel, such as when the balloon diameter has a tolerance of 1 mm.

FIG. 10 illustrates a sectional view of the distal portion of a delivery device including an implant, consistent with embodiments of the present disclosure. Delivery device 100 may comprise a similar construction to device 100 of FIG. 1, with the addition of an additional shaft 106 which surrounds shaft 102 as shown, and travels proximally to surround shaft 101, not shown but depicted in FIG. 1. Space 107 resides between shaft 106 and shaft 102, such as a space in fluid communication with a port on the proximal end of device 100, not shown but typically a luer or other standard connector for attachment to a source of balloon inflation fluid. A guidewire lumen 104 resides within shaft 102, and is typically configured in a rapid exchange configuration wherein lumen 104 exits the side of device 100 in or proximate to a distal portion of device 100. In the illustrated embodiment, shaft 101, having a proximal end and a distal end, comprises a length such that shaft 101 distal end terminates proximal to balloon 114 such as at a location flush with proximal balloon bond 122.

In one embodiment, shaft 102 comprises a multi-layer construction, such as two layers comprising a co-extrusion of Pebax™ 55D and PTFE. In another embodiment, the two layers comprise a co-extrusion of Pebax™ 55D and HDPE. Shaft 102 includes ribbon coil 180 configured to provide one or more functions including but not limited to: preventing collapse of shaft 102 (e.g. occluding lumen 104); preventing undesired bending such as to provide better guidewire movement within lumen 104 when shaft 102 is placed in tortuous vessel anatomy; providing improved pushability of (e.g. ability to smoothly advance) device 100; reducing the risk of kinking such as when implant 150 is deployed in an acute curve or other vessel tortuousity commonly experienced in neurovasculature; and providing improved uniformity of deployment of implant 150. Coil 180 may include one or more markers, e.g. radiopaque or other visualizable markers, thus increasing visibility of shaft 102. In this embodiment, shaft 102 durometer may be softer than shaft 102 without the reinforcement provided by coil 180. For example, with coil 180, shaft 102 durometer may range from 35D to 72D, preferably 55D. The width of coil 180 may range from 0.001" to 0.004"; coil 180 thickness may range from 0.0005" to 0.002"; and coil pitch may range from 0.004 to 0.012". Coil 180 material may be stainless steel 304V and may include dimensions of 0.00225" wide by 0.0008" thick, with a 0.0058" pitch. Coil 180 may be wrapped within lumen 104 of shaft 102, or be placed between two layers of shaft 102, such as between a PTFE layer and a Pebax™ 55D nylon outer jacket. In another embodiment, shaft 102 can include a HDPE layer and a Pebax™ 55D nylon outer jacket. In yet another embodiment, shaft 102 includes three layers in addition to coil 180. For example, the three layers of shaft 102 may include a PTFE layer, a Pebax™ layer, and a bonding layer of urethane positioned therebetween.

Space 107 is typically in fluid communication with a lumen of a proximal shaft, such as lumen 104 of shaft 102 of FIG. 1, and is configured to allow fluid to enter balloon 114 such as to radially expand balloon 114 to deploy implant 150 in a body lumen such as a blood vessel. Shaft 106, which surrounds space 107, may comprise multiple layers, such as two equally thick layers of Grilamid Nylon. Shaft 106 may be reinforced with coil 182, providing similar benefits to that of shaft 102 by coil 180. In addition, coil 182 preserves the roundness of shaft 106, thus minimizing the potential for space 107 to "ovalize" or otherwise fully or partially occlude. In other words, it is desirable for space 107 to maintain its shape so that inflation and deflation of balloon 114 occurs uniformly. Shaft 106, with coil 182 included, may comprise a durometer ranging between 40D to 72D, preferably 62D. Coil 182 may be sandwiched in between the two layers of Grilamid Nylon making up shaft 106. In one embodiment, shaft 106 inner diameter is approximately 0.031", and its outer diameter is approximately 0.037". The width of coil 182 may range from 0.001" to 0.004"; coil 180 thickness may range from 0.0005" to 0.002"; and coil pitch may range from 0.006" to 0.012". In some embodiments, coil 182 may be stainless steel 304V, with dimensions of approximately 0.00125" diameter with a 0.010" pitch.

Distal navigation segment 200 is positioned as shown, on a distal portion of device 100. Distal navigation segment 200 is constructed and arranged such that at least a portion of tip 201 can advance around a tight turn, then providing a smooth transition of the remaining more proximal components of delivery device 100. Distal navigation segment 200 can be created by extending shaft 102 a length of approximately 6.0 mm+/−0.5 mm beyond a bonded portion of the distal end of balloon 114, distal bond 203. The segment of shaft 102 extending beyond distal bond 203 is segment 202, which may include a reinforcing layer, e.g. a third layer when shaft 102 proximal portion comprises two layers. In the illustrated embodiment, the third layer includes a 5 mm length segment of Pebax™ 2533 and a 5 mm segment of Pebax™ 3533, bulking shaft 102 from an initial outer diameter to larger final outer diameter, for example, from an initial diameter of 0.022" to a final diameter of 0.027". Therefore, in the multilayer construction of shaft 102 described above, distal navigation segment 200 may include an inner layer of HDPE, a middle layer of Pebax™ 55D, and an outer layer of Pebax™ 2533/3533, such as to result in a 0.027" outer diameter and a total length of 12 mm. Additionally or alternatively, the inner layer may include PTFE. In an alternate embodiment, distal navigation segment 200 may be 6 mm in length and include a single polymer with a durometer ranging from 25D to 55D, preferably 35D. As described above, distal navigation segment 200 further includes a distal tip, typically, a relatively flexible, floppy tip 201. In one embodiment, floppy tip 201 includes Pebax™ 63D, is approximately 3 mm in length, and provides a less traumatic cushion tip while maintaining sufficient durability. The final dimensions also account for a 0.25 mm to 1.5 mm overlap for shaft 102 to mate with the outer layer of Pebax™ 2533. In this configuration, the total distance beyond distal bond 203 is approximately 9 mm, which includes 6 mm for extension 202 and 3 mm for tip 201, including overlaps. Delivery device 100 may include one or more markers 191, typically radiopaque markers configured to enhance visibility or other visualizable markers as are described herein. Similarly, balloon 114 may include one or more markers 190, typically radiopaque markers configured to enhance visibility or other visualizable markers.

In another embodiment, distal navigation segment 200 may include a softer material, such as Pebax™ 40D, enabling the diameter of the segment 200 to be larger, typically similar to the distal end of shaft 106, while providing sufficient flexibility. Distal navigation segment 200, such as when comprising Pebax™ 40D, may be fused with tip 201 and shaft 102, with segment 200 remaining sufficiently flexible.

Figure 11:
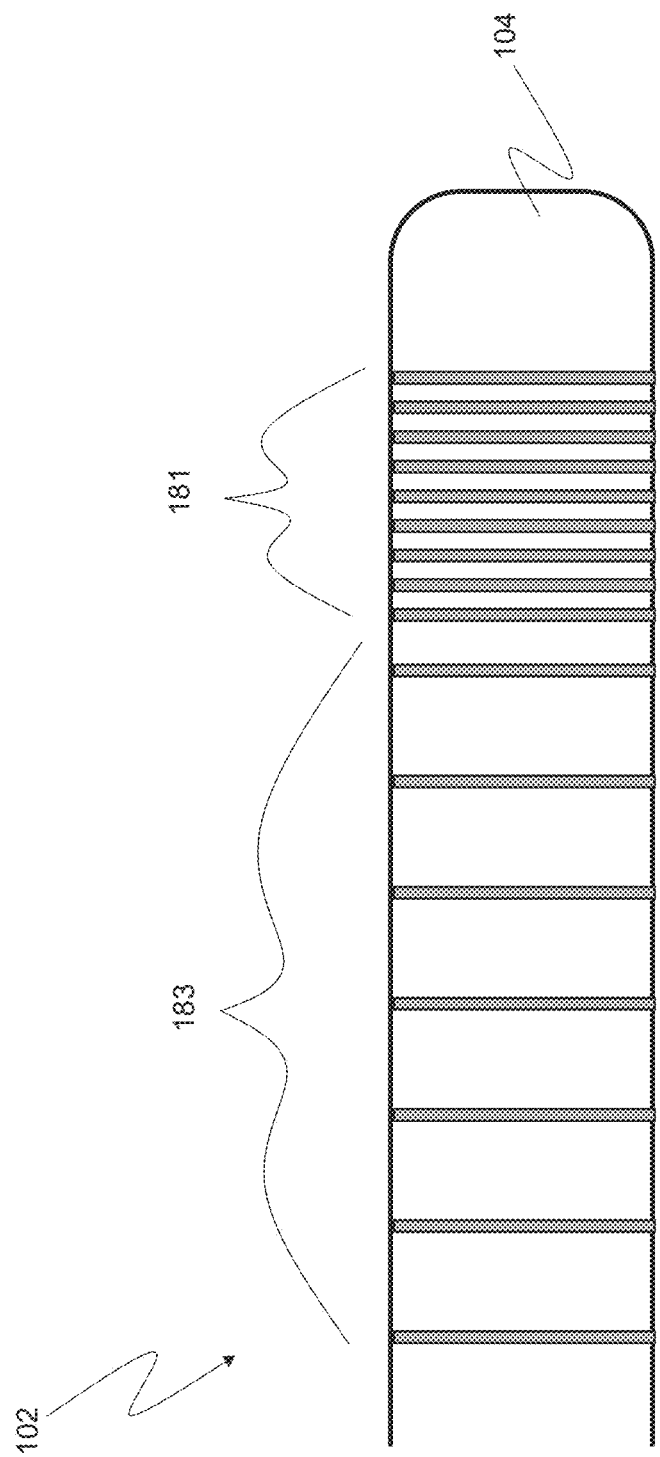
FIG. 11 illustrates a shaft of a delivery device including a coil with an axially compressed distal end, consistent with embodiments of the present disclosure.

FIG. 11 illustrates a shaft of a delivery device including a coil with spacing between coils decreasing as they approach the shaft distal end, consistent with embodiments of the present disclosure. A distal portion of shaft 102, typically similar to a distal portion of shaft 102 of FIG. 10, includes coil portions 183 and 181, wherein coil portion 181 is positioned more distal than coil portions 183. Shaft 102 includes lumen 104, such as a guidewire lumen constructed and arranged to slidingly receive a 0.014" guidewire. Coil portion 181 includes coils spaced such that the portion of shaft 102 proximate coil portion 181 may be flexed in a tighter bend than the portion of shaft 102 proximate coil portion 183. Coil portion 181 typically comprises a length of 0.040". In an alternate embodiment, a radiopaque marker can replace or be integrated into coil portion 181 and/or coil portion 183.

FIG. 12 illustrates a shaped mandrel for insertion into an implant delivery device, consistent with embodiments of the present disclosure. Mandrel 300 includes bend portion 301, including an inflexion point, bend 304, typically a 45° bend that can be employed during a preparatory step in preparing an implant delivery device for insertion into a diseased vessel to be treated. Prior to delivery of an implant, such as implant 150 or implant 250 described in detail herein, the distal end of a delivery device, such as delivery device 100 described in detail herein and including implant 150 or implant 250, is placed over shaped mandrel 300 (i.e. shaped mandrel 300 is placed in a guidewire lumen, lumen 103 of system 10 of FIG. 1). Mandrel 300 is shaped, constructed and otherwise configured to relieve stresses in, to modify the shape of and/or to otherwise improve the trackability of the implant delivery device when advanced over an intravascularly placed guidewire. Testing has shown 40% reduction in tracking forces and greater can be achieved after insertion and removal of mandrel 300. Shaped mandrel 300 can be constructed of a semi-rigid material, such as a metal such as stainless steel 304V. Shaped mandrel 300 can include an approximate 45° bend 301 and a bend radius ranging from 0.29" to 0.33", preferably 0.315". The outer diameter of shaped mandrel 300 is sized for insertion into a lumen of a delivery device and typically ranges from 0.01" to 0.02", preferably 0.015". The length of shaped mandrel 300 can range from 19.0" to 20.0", preferably 19.5". The 45° bend 301 can be positioned approximately 18.0" from the straight (non-looped) end. Mandrel 300 may include a coating such as a hydrophilic coating, for example a hydrophilic coating activated upon dipping mandrel 300 in a saline solution. Mandrel 300 can include looped end 302 constructed and arranged to prevent mandrel 300 from entering the distal end of the implant delivery device. According to the illustrated embodiment, shaped mandrel distal end 303 is inserted into the distal end of a delivery device, including an implant therein. The delivery device is advanced up to and around curve 304 so that the entire implant tracks through the curve so that the distal end of the delivery device tracks up to looped end 302. The delivery device and the implant are pulled back through the curve. Subsequently, mandrel 300 is rotated 120° and the delivery device is tracked forward and back over curve 304 once again, and finally, the implant is rotated another 120° and tracked over curve 304 and back again. As a result, all three 120° planes of the implant are stress relieved.

Figure 13:
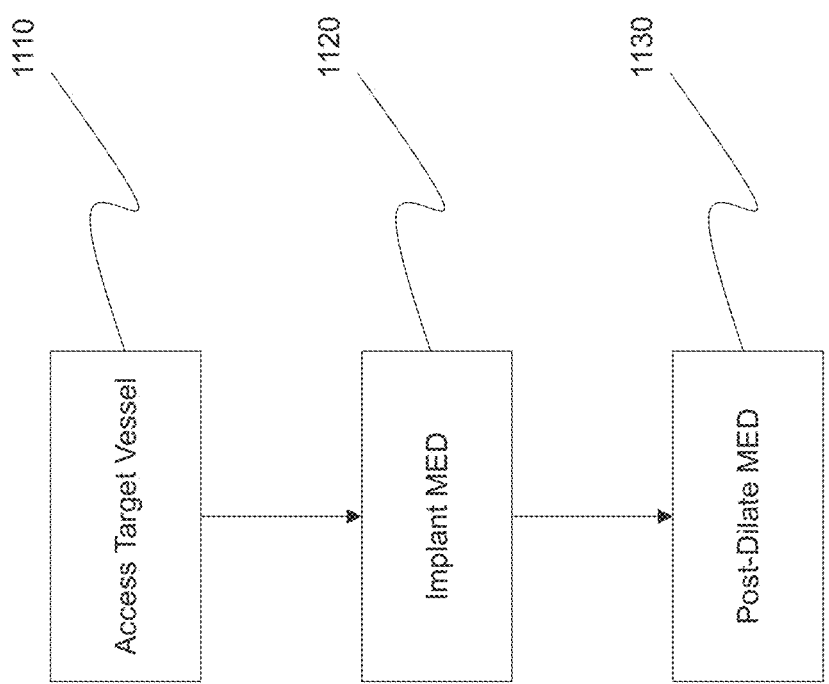
FIG. 13 illustrates a flow chart of a method for treating a diseased vessel, consistent with embodiments of the present disclosure.

FIG. 13 illustrates a method for treating a diseased vessel using the system of the present disclosure. The delivery device and implant employed in the illustrated method can be the delivery device and implant discussed in reference to the Figures hereabove. Additionally, the implant may include a membrane as discussed in reference to the Figures hereabove. In STEP 1110, a target vessel is accessed using a delivery device where the delivery device is configured to position a mechanically expandable device, e.g. an implant, in a vessel. In STEP 1120, the implant is deployed and expanded such that an exterior surface of the implant engages with the inner surface of a vessel so as to maintain a fluid pathway through the vessel while obstructing blood flow to an aneurysm. Prior to accessing a target vessel, the delivery device can be tracked over a shaped mandrel to relieve stresses and improve trackability, for example, shaped mandrel 300 described in reference to FIG. 12 hereabove. In one embodiment, the delivery device and/or mandrel is exposed to fluid, such as by dipping in saline prior to insertion in the patient, to activate a hydrophilic coating. The delivery device is purged of air (e.g. with saline) prior to insertion of the guidewire.

STEP 1110 further includes preparing an access site, where the access site may be selected from the group consisting of: femoral artery; brachial artery and radial artery. Also in this step, a distal portion of a guidewire, typically a 0.014" guidewire, is positioned in the target vessel. While maintaining the position of the guidewire in the vessel, the delivery device is loaded onto a proximal end of the guidewire. The implant may be pre-mounted on the delivery device, or the implant may be applied to the delivery device in the clinical setting. Angiography and/or fluoroscopy can be performed to confirm proper placement of the guidewire. The delivery device is advanced over the guidewire to the target vessel. Angiography and/or fluoroscopy may be performed to confirm positioning of the distal portion of the delivery device and/or the pre-deployed location of the implant. In some embodiments, the implant is advanced to a location distal to the target deployment location for the implant, followed by gently retracting the delivery device to position the implant at the target location. This technique can be employed to ensure any potential slack is relieved, thus reducing the possibility of movement during inflation of a deploying balloon and/or retraction of a sheath (e.g. a sheath surrounding a self-expanding implant). In a next step, an inflatable element, e.g. a balloon integral to the delivery device, may be inflated. Prior to inflation, the balloon and its inflation lumen may be purged of air, such as with a small 4-cc snub-nose flushing syringe.

STEP 1120 may include inflating balloon such that the implant reaches the desired diameter, i.e. diameter of the vessel, typically, 2.0 mm to 5.0 mm, such as when the implant is a plastically deformable device. In some embodiments, the implant can be expanded such that the implant inner diameter matches that of the vessel inner diameter (e.g. expanded with a balloon with a diameter slightly greater than the vessel inner diameter). The opening pressure, i.e. pressure at which the implant is fully open, may be approximately 5 atm. In an alternative embodiment, the implant comprises a self-expanding implant, and the implant is deployed by pulling back a retractable sheath, as is described in reference to FIG. 17 herebelow. A balloon may be included, underneath the sheath and pre-deployed implant, such that additional deploying forces can be exerted on the self-expanding implant, after initial deployment. In yet another embodiment, the implant can include both self-expanding portions and balloon-expandable portions. For example, the implant can be deployed in a vessel via a delivery device including a retractable sheath (as described in FIG. 15 herebelow), self-expand to contact the vessel wall, and then certain portions of the implant can be further expanded via a balloon such as a balloon included within the same delivery device, or a balloon included on a second device.

Contact between the implant and the vessel wall is desired and can be confirmed via MRI, Dyna CT, Angio CT, angiography and/or fluoroscopy. After the implant is expanded to the desired diameter, the balloon can be deflated completely. A vacuum can be applied with the inflation device and held until most of the contrast solution is removed from the system and the balloon folds are folded. In a next step, the delivery device may be removed over the guidewire.

In STEP 1130, the implant can optionally be further plastically deformed and/or otherwise radially expanded post-deployment, such as by using a post-dilatation balloon configured to increase the diameter of a specific portion of the implant. One or more expansion steps may be performed until the correct mating with the vessel walls is achieved, e.g. to eliminate false lumens, such that no leak is observed. In some embodiments, the post dilatation balloon can be positioned and operated to expand a proximal portion of the implant prior to expanding a distal portion of the implant. In one embodiment, STEP 1130 is performed immediately after STEPs 1110 and 1120 are performed, i.e. during the same procedure. Additionally or alternatively, STEP 1130 can be performed during a second procedure, for example a procedure performed one day, one week, one month, or six months later, and any combinations of these. Finally, the guidewire is removed after all access to the deployed implant is complete.

Figure 14C:
FIGS. 14A, 14B, and 14C illustrate angiographic images of an aneurysm, prior to, and 15 minutes and six months after placement of an implant, respectively, consistent with embodiments of the present disclosure.
Figure 14B:
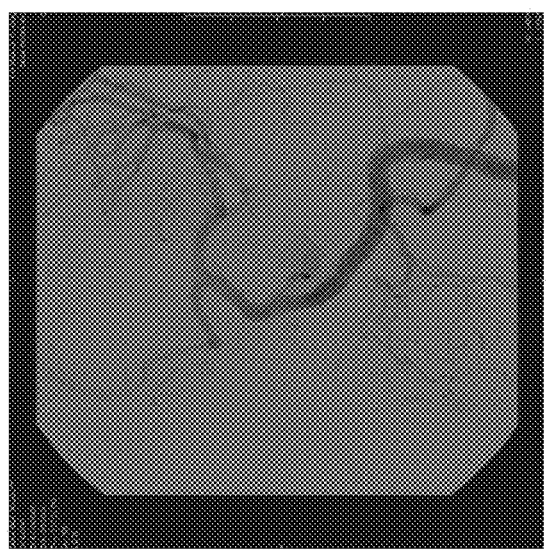
Figure 14A:
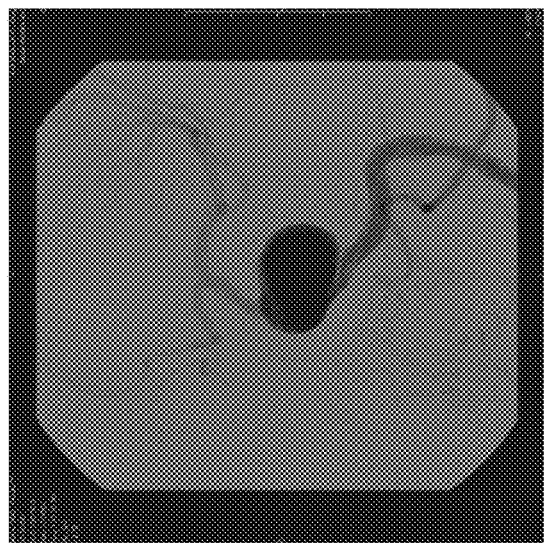

FIGS. 14A-C illustrate an angiograph of an aneurysm prior to, 15 minutes and six months after deployment of an implant, respectively, consistent with embodiments of the present disclosure. As illustrated, after implantation of a single implant of embodiments of the prevent disclosure, the aneurysm is safely and effectively occluded.

Figure 15:
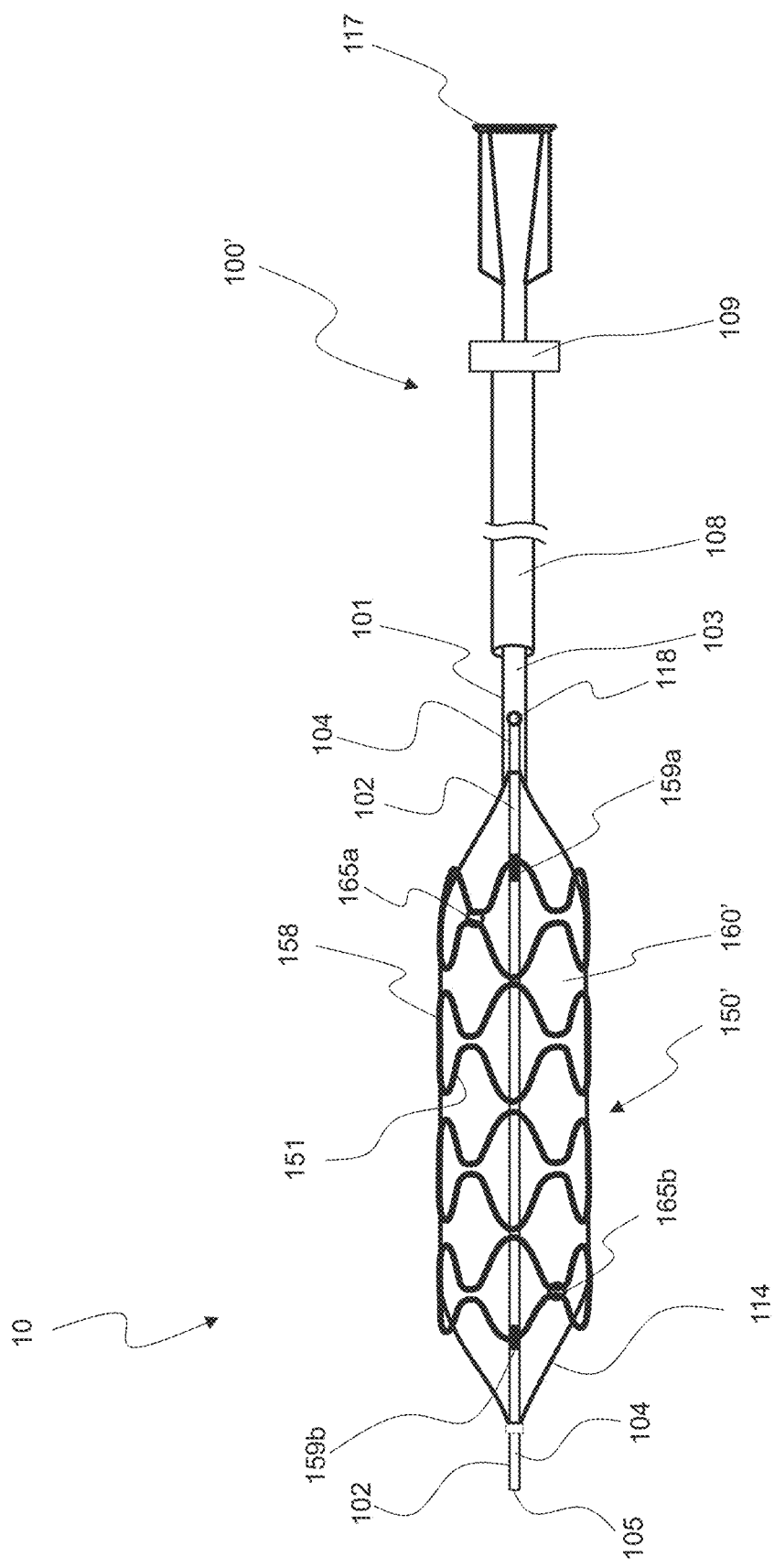
FIG. 15 illustrates a delivery device with a self-expanding implant and retracted delivery sheath, consistent with embodiments of the present disclosure.

FIG. 15 illustrates a delivery device including a self-expanding implant and a retractable delivery sheath, consistent with embodiments of the present disclosure. System 10 comprises delivery device 100' and self-expanding implant 150'. Sheath 108 is configured to surround self-expanding implant 150' in its radially compact state. Sheath 108 is shown after having been retracted, such as by pulling back flange 109, fixedly attached to sheath 108, and allowing implant 150' to self-expand to the expanded condition shown. Delivery device 100' may further include a balloon, balloon 160' also shown having been radially expanded, such as via fluid introduced through port 117 as described in reference to FIG. 1 hereabove. Alternatively, delivery device 100' may not include a balloon.

Other components of delivery device 100' are typically similar to and described in detail in reference to the same numbered components of delivery device 100 of FIG. 1.

Figure 16:
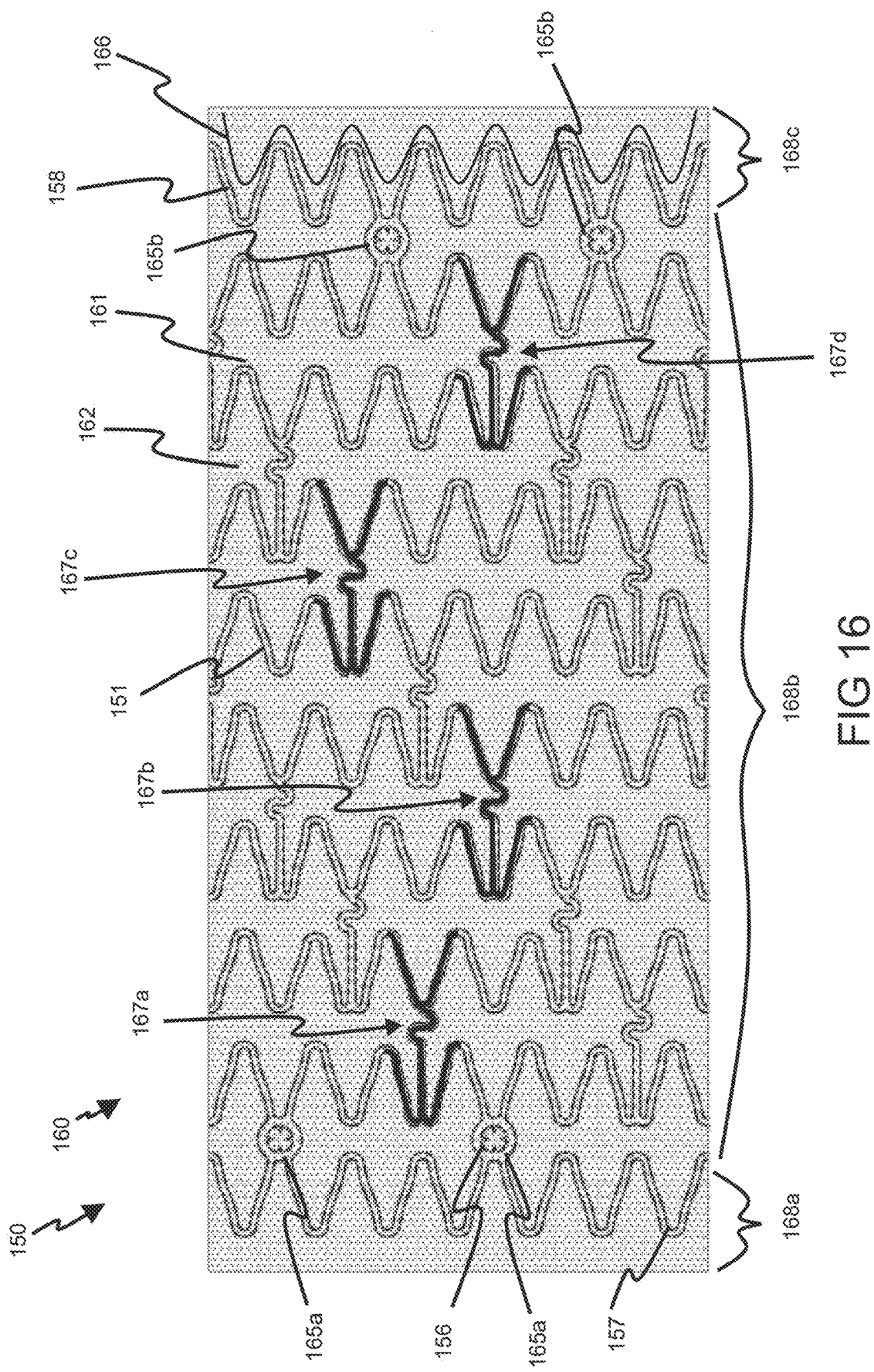
FIG. 16 illustrates an implant including a membrane, unrolled to more clearly show the configuration of the implant elements, consistent with embodiments of the present disclosure.

FIG. 16 illustrates an implant including a membrane, unrolled to more clearly show the configuration of the implant elements. Preferably, implant 150 is an initially solid tubular member, defining a longitudinal axis and a circumference. The walls of the tubular member are selectively removed by high precision cutting, e.g. laser cutting, chemical etching, water jet cutting, or standard tool machining, to provide frame 158, including struts 151. Additionally or alternatively, implant 150 may be formed from a flat sheet of material that is rolled and axially fused together after creating frame 158.

In the illustrated embodiment, frame 158 includes four portions, portions 167*a-d*, where portions 167*a-d* comprise properties that can be similar from portion to portion, or can vary from portion to portion. In one non-limiting embodiment, portions 167*a* and 167*b* can be plastically deformed during the radial expansion of implant 150 while portions 167*b* and 167*c* can be resiliently biased when implant 150 is in an expanded state. Other properties than can be varied from portion 167*a* through portion 167*d* include but are not limited to: flexibility; rigidity; biodegradability; and combinations of these. These properties can be achieved via the materials used and/or coatings. For example, portions 167*a* and 167d can comprise a more rigid material to achieve more rigid ends of implant 150, and portions 167b and 167c can include a more flexible material. Additionally or alternatively, portions 167a and 167d can include a coating, for example a lubricious coating, while portions 167b and 167c do not include a coating. These properties or any other physical, chemical, or mechanical property can be combined in any way so as to achieve the desired implant 150.

In the illustrated embodiment, frame 158 is covered by permeable membrane 160 which includes pores 161 and spaces 162. Similar to frame 158, membrane 160 can include portions, for example portions 168a-c. In one embodiment, membrane 160 has a uniform porosity, for example, portions 168a-c include pores 161 comprising approximately the same diameter as well as approximately the same distance between adjacent pores 161. In an alternative embodiment, membrane 160 has a non-uniform porosity, for example pore size and/or distance between adjacent pores 161 varies from portion 168a to portion 168b to portion 168c. Alternatively or additionally, pore geometry can vary across membrane portions 168a-c. For example, portion 168a can include round pores, portion 168b can include elliptical pores, and portion 168c can include pores in a rectangular, slit shape. In another non-limiting example, portion 168a and portion 168c includes round holes, while portion 168b includes elliptical pores. In this embodiment, a first porosity can be achieved at the ends of implant 150 and a second, different porosity can be achieved at the mid portion of implant 150. In some embodiments, membrane 160 is configured to deliver a drug(s), reagent(s) and/or other agent(s) to a vessel simultaneous with or after implantation of implant 150. Portions 168a-c can include the same or different drugs or agents configured to be released simultaneously or sequentially. For example, membrane portion 168a can include a first drug configured to be released immediately after implantation of implant 150, and portion 168b includes a second drug configured to be released one day after implantation, and portion 168c includes a third drug configured to be released one month after implantation. In an alternative embodiment, the entire membrane can include a drug(s) and/or agent(s). Alternatively or additionally, membrane 160 can include a coating, for example a lubricious coating included in portion 168a, b, and/or c, or the coating can cover the entire implant 150.

FIG. 17A illustrates a distal portion of a delivery device including a balloon, where the proximal and distal ends of the balloon have been expanded such that an implant is stabilized on the delivery device prior to implantation. In FIG. 17A, both the proximal and distal ends of the balloon have been expanded, however in some embodiments, only one of the proximal or the distal end is expanded. FIG. 17B illustrates the balloon of FIG. 17A further expanded for deployment and implantation of the implant. Delivery device 100 includes balloon 114 located on the distal portion of shaft 102. To stabilize implant 150 on delivery device 100 prior to implantation, balloon 114 distal and proximal ends have been pressurized such as to create balloon shoulders 115b and 115a, respectively, resulting in a "dogbone" shaped balloon 114. Balloon shoulders 115a and 115b can be created via the introduction of thermal energy, for example via a cold process, i.e., the introduction of a cold fluid, or via a heat induced process, i.e., the introduction of heat.

The cold process comprises wrapping and crimping implant 150 onto balloon 114, followed by inflating balloon 114 with pressurized nitrogen into a die. Typically, balloon 114 is inflated so that its inner diameter is approximately 0.070"-0.073". Subsequently, implant 150 is crimped onto balloon 114.

The heat induced process comprises crimping implant 150 onto balloon 114, followed by placing a tubular conduit around implant 150 to prevent implant 150 from expanding during the expansion of shoulders 115a and 115b, the tubular conduit not shown but can comprise at least one of Polyimide, reinforced PTFE, or polished stainless steel. Optionally, an additional tubular conduit, also not shown but can be placed over at least one of the distal end or proximal end of balloon 114 to define the final outer diameter of balloon shoulders 115b and 115a, respectively. Subsequently, balloon 114 including implant 150 is placed in an oven and pressurized with Nitrogen where balloon 114 is molded into the "dogbone" shape. In one embodiment, oven temperature ranges from 50° to 70° C., typically from 55° to 65°; bake time ranges from 30 seconds to 15 minutes, typically from 5 minutes to 10 minutes; and Nitrogen pressure ranges from 5 psi to 60 psi, typically from 10 psi to 50 psi. After the pressurization and heat set process, the tubular conduit is removed from implant 150, as well as any optional tubular conduits placed around balloon distal and proximal ends.

Upon reaching the desired implantation location, balloon 114 can be further expanded such that the outer diameter of balloon 114 approximately matches the inner diameter of implant 150, and implant 150 can be implanted at the vessel location, as shown in FIG. 17B.

Figure 18A:
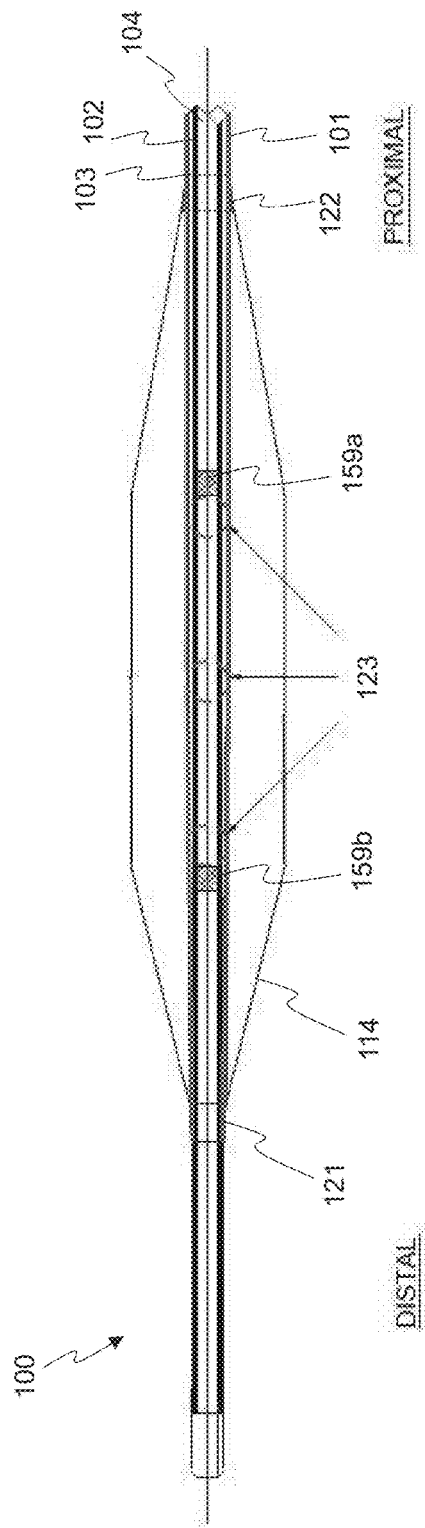
FIGS. 18A and 18B illustrate a distal portion of an implant delivery device including an extended shaft, consistent with embodiments of the present disclosure.
Figure 18B:
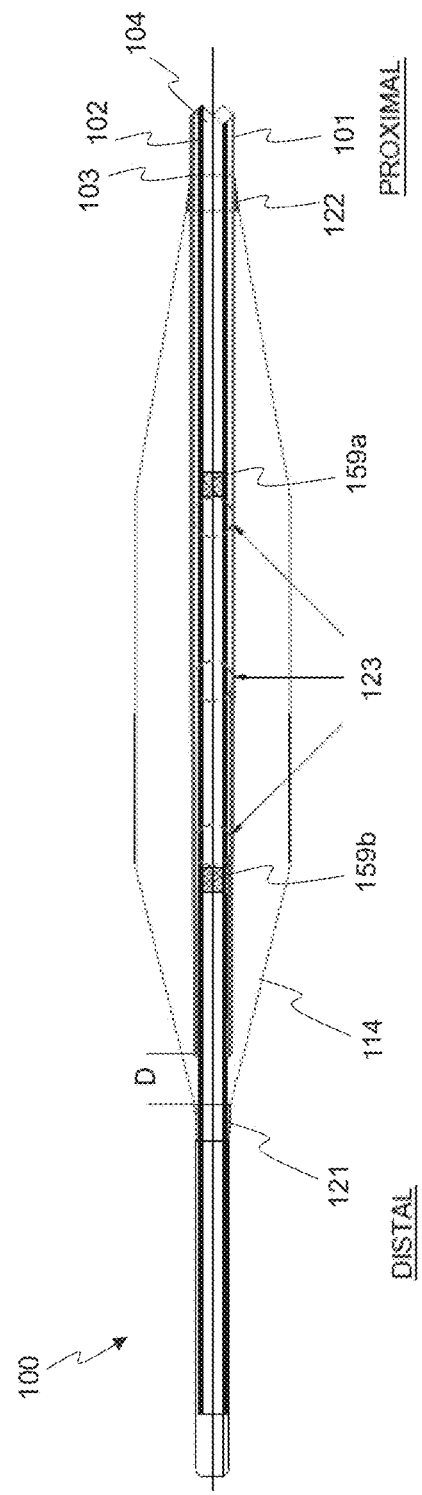

FIGS. 18A and 18B illustrate a distal portion of an implant delivery device including an extended shaft. The delivery device, such as delivery device 100 described herein, includes shaft 101 including lumen 103, typically an inflation lumen in fluid communication with balloon 114, configured to be operably inflated by delivery of fluid through lumen 103. In some embodiments, for example the embodiment illustrated in FIG. 10, shaft 101, having a proximal end and a distal end, comprises a length such that shaft 101 distal end terminates proximal to balloon 114 such as at a location flush with proximal balloon bond 122. In FIG. 18A, shaft 101 distal end extends beyond balloon 114 such as to a location flush with distal balloon bond 121. In this embodiment, shaft 101 distal end can either be fixedly attached to distal balloon bond 121, or configured to allow relative motion between shaft 101 distal end and distal balloon bond 121. In FIG. 18B, shaft 101 terminates proximal to distal balloon bond 121 at a distance D. In some embodiments, D is approximately 1 mm proximal to the proximal edge of distal balloon bond 121. By extending shaft 101 distal to balloon 114, movement of shaft 102 into lumen 103 of shaft 101 is minimized as delivery device 100 is tracked through a vessel, specifically when distal balloon bond 121 experiences friction.

In the embodiments shown in FIGS. 18A and 18B, shaft 101 can include at least one hole 123 to assist in inflation and deflation of balloon 114. Shaft 101 can include one to twenty holes 123, and in some cases between five and ten holes 123. Holes 123 can comprise various cross sectional shapes, hole sizes and multiple hole patterns. For example, holes 123 can comprise a diameter ranging from approximately 0.005" to 0.025", or from approximately 0.010" to 0.015". Multiple holes 123 can be drilled in a desired hole pattern, for example a diamond shaped pattern of holes where holes 123 are uniformly sized and spaced. Additionally or alternatively, holes 123 can be drilled in a non-uniform pattern along shaft 101, for example by varying hole size, shape and/or spacing.

A post-dilatation balloon as has been described herein, can comprise an extended inflation shaft and lumen, constructed and arranged similar to shaft 101 of delivery device 100 of FIGS. 18A and/or 18B.

Figure 19A:
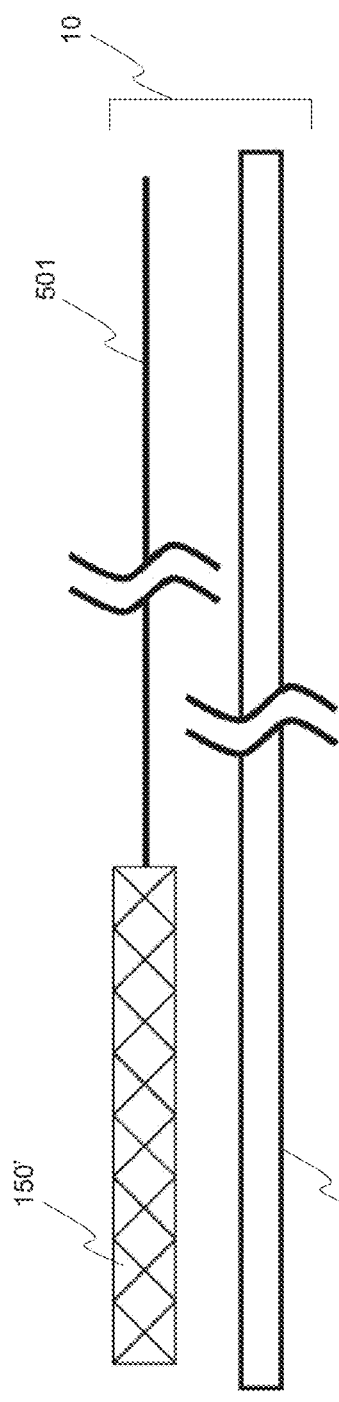
FIG. 19A illustrates a self-expanding implant with a delivery wire and a micro-catheter configured for delivery and expansion of the implant, consistent with embodiments of the present disclosure.
Figure 19B:
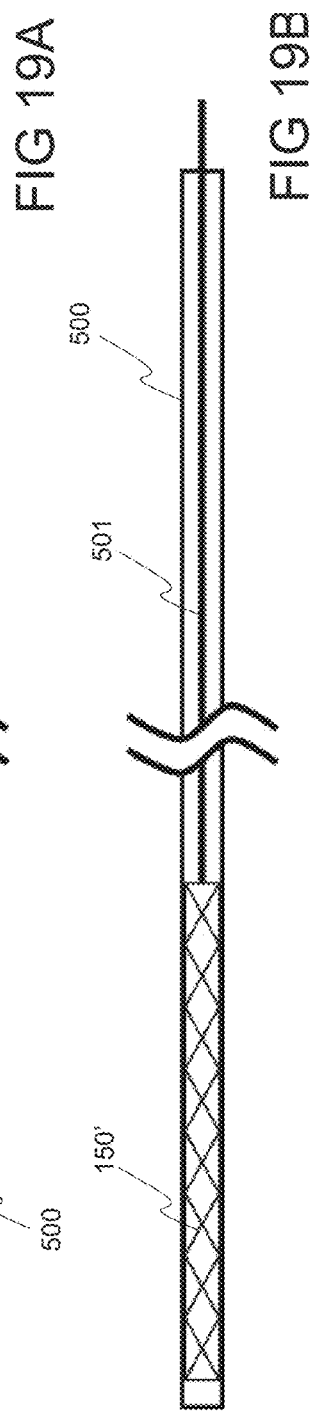
FIG. 19B illustrates the implant of FIG. 19A loaded onto the micro-catheter, consistent with embodiments of the present disclosure.
Figure 19C:
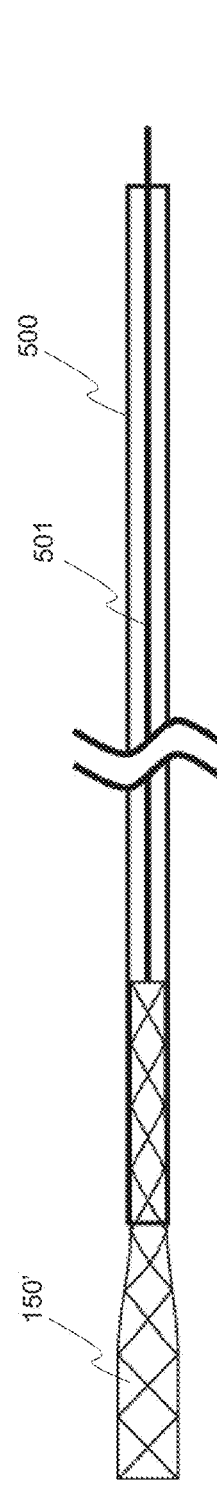
FIG. 19C illustrates the implant of FIG. 19A partially deployed and partially expanded, consistent with embodiments of the present disclosure.
Figure 19D:
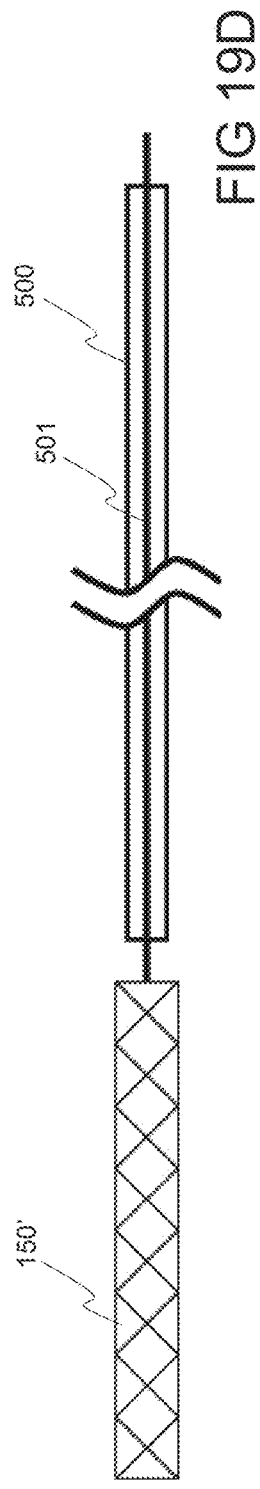
FIG. 19D illustrates the implant of FIG. 19A fully deployed and expanded, where the delivery wire is retracted into the micro-catheter, consistent with embodiments of the present disclosure.

FIG. 19A illustrates a system comprising an implant with a delivery wire and a micro-catheter configured for delivery and expansion of the implant; FIG. 19B illustrates the implant of FIG. 19A loaded into the micro-catheter; FIG. 19C illustrates the implant of FIG. 19A partially deployed and partially expanded; and FIG. 19D illustrates the implant of FIG. 19A fully deployed and fully expanded, with the delivery wire is retracted into the micro-catheter. The embodiment shown in FIGS. 19A-D can be implanted in a curved vessel, for example as shown in FIGS. 9A-C, however embodiments are shown in a simple linear configuration with exaggerated lines for illustrative clarity.

System 10 includes implant 150', delivery wire 501 and micro-catheter 500. System 10 can be configured for treatment of an aneurysm located in a blood vessel. such as a blood vessel in the brain of a patient. Implant 150' can comprise a self-expanding implant, or comprise one or more self-expanding portions as have been described herein. Implant 150' can be delivered to a vessel via micro-catheter 500 and delivery wire 501. Delivery wire 501 can be operably attached to implant 150' and configured to advance and/or retract implant 150' to and from micro-catheter 500. Implant 150' can be loaded into micro-catheter 500 by manually compacting implant 150' and inserting it into micro-catheter 500, and advancing delivery wire 501 and implant 150' to the position shown in FIG. 19B. To deploy and expand implant 150', delivery wire 501 is further advanced distally such that implant 150' begins to exit the distal end of micro-catheter 50, such as to the position shown in FIG. 19C. In some embodiments, implant 150' can be retracted back within micro-catheter 500 when implant 150' is less than or equal to approximately 90% deployed (i.e. up to approximately 90% of the length of implant 150' is external to micro-catheter 500). Recapturing of implant 150' after partial deployment can be performed to reposition implant 150' or to abandon implantation of implant 150'. Full deployment of implant 150' is achieved by advancing delivery wire 501 until implant 150' has fully exited micro-catheter 500. When implant 150' is fully deployed, as shown in FIG. 19D, and in a desired positioned within a vessel, delivery wire 501 can be configured to detached from implant 150', such as a detachment caused by an operator. Subsequently, micro-catheter 500 and delivery wire 501 can be removed from the vessel.

In some embodiments, delivery wire 501 and micro-catheter 500 are constructed and arranged similar to the transport wire and micro-catheter included in the Asperio Thrombectomy System provided by Acandis Aperio GMBH & Co. KG of Pforzheim, Germany. Alternatively or additionally, delivery wire 501 and micro-catheter 500 are constructed arranged as described in U.S. patent application Ser. No. 13/320,148, entitled "Medical Device for Releasing in a Hollow Organ and Insertion System for Medical Devices" and filed Dec. 1, 2011, incorporated herein by reference in its entirety.

FIG. 20A illustrates an implant comprising a first expandable device and a second expandable device; FIG. 20B illustrates the first expandable device implanted within a vessel, and FIG. 20C illustrates the second expandable device also implanted within the vessel of FIG. 20B. In some embodiments, the first expandable device, implant 150', comprises a self-expanding device, and the second expandable device, implant 150, comprises a balloon expandable device. Implant 150 comprises first implant 150' and second implant 150". In some embodiments, implant 150' and implant 150" comprise different materials (e.g. one is self-expanding and one is plastically deformable), different geometries (e.g. different lengths, diameters and/or pore size), and/or other construction differences. In some embodiments, implant 150' and implant 150" are configured to perform different functions prior to, during and/or after implantation. For example, implant 150' can be configured to provide adequate coverage of a vessel wall, and implant 150" can be configured to provide adequate apposition between implant 150' and/or implant 150" and the vessel wall. As shown in FIG. 20B, implant 150' has been deployed in the vessel, however adequate apposition has not been achieved. Subsequently, implant 150" can be deployed and expanded, as shown in FIG. 20C, achieving adequate apposition of implant 150' and 150" with the vessel wall.

In some embodiments, implant 150' may be implanted, and implant 150" may be implanted in approximately the same position (e.g. the mid-portion of each is aligned at the same location in the vessel). In the illustrated embodiment, implant 150" is longer than implant 150' and implanted such that implant 150 extends past both the proximal and distal ends of implant 150'. In some embodiments, implant 150' and implant 150" may be implanted such that they overlap one another, having any amount of overlap, for example where the overlapping portion is proximate an aneurysm. In some embodiments, implant 150' and implant 150" may be implanted in a tandem configuration.

As stated above, implant 150' and implant 150" may be similar or dissimilar in construction, e.g. similar or dissimilar materials, braid configuration, size, coatings, radiopacity, inclusion of radiopaque markers, and the like. Implant 150 and implant 150' can embody any of the configurations described herein.

The present application incorporates by reference the entirety of U.S. Non-Provisional application Ser. No. 10/580,139, filed Dec. 13, 2004 and published on May 3, 2007 as U.S. Pub. No. 2007/0100430; U.S. Non-Provisional application Ser. No. 11/586,899, filed Oct. 25, 2006 and published on May 3, 2007 as U.S. Pub. No. 2007/0100426; U.S. Non-Provisional application Ser. No. 11/786,023, filed Apr. 9, 2007 and published on Nov. 1, 2007 as U.S. Pub. No. 2007/0255388; and U.S. Non-Provisional application Ser. No. 12/279,335, filed Feb. 13, 2006 and published on Feb. 26, 2009 as U.S. Pub. No. 2009/0054966.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A system for treating a diseased vessel comprising:
   an expandable device constructed and arranged to radially expand from a first position to a second position, the expandable device comprising at least two portions wherein the first portion is plastically deformable during the radial expansion from the first position to the second position and the second portion is resiliently biased in the second position;
   a membrane expandable in response to the expansion of the expandable device and comprising a plurality of polymeric strips wrapped circumferentially around and secured to the expandable device, the membrane comprising at least one porous portion comprising one or more pores;
   a delivery device constructed and arranged to position the expandable device such that the exterior surface of the expandable device engages with the inner surface of the vessel and maintains a fluid pathway through said vessel, wherein the delivery device comprises a catheter assembly having a proximal portion and a distal segment, more flexible than the proximal portion, wherein the catheter assembly includes,
      a first shaft including an inflation lumen,
      a second shaft including a guidewire lumen exiting through a sidewall of the first shaft, and
      a third shaft surrounding the guidewire lumen, wherein the second shaft further comprises a first coil surrounding the guidewire lumen and disposed within a wall of the second shaft,
      a second coil is disposed within a body of the third shaft, and
      a first marker positioned on the second shaft at a proximal end of the expandable device, and a second marker positioned on the second shaft at a distal end of the expandable device;
   and
   at least one proximal ring located at the proximal end of the expandable device and at least one distal ring located at the distal end of the expandable device, each of the at least one proximal ring and the at least one distal ring configured to anchor the expandable device to a vessel wall,
      wherein the membrane is not included on one or both of the at least one proximal ring and the at least one distal ring, thereby permitting the proximal end or the distal end that does not include the membrane to be radially displaced more than portions of the expandable device that include the membrane, and the at least one proximal ring and the at least one distal ring include teeth configured to secure the first marker and the second marker included in the delivery device.

2. The system of claim 1, wherein the system is constructed and arranged to treat an intracranial aneurysm arising from a parent vessel wherein the parent vessel comprises a diameter of approximately 2.0 mm to 5.0 mm.

3. The system of claim 1, wherein the expandable device is constructed and arranged to be plastically deformed during the radial expansion from the first position to the second position.

4. The system of claim 1, wherein the expandable device is resiliently biased in the second position.

5. The system of claim 1, wherein the expandable device is loaded onto the delivery device, the delivery device comprising a micro-catheter and a wire.

6. The system of claim 1, wherein the system further comprises a second expandable device constructed and arranged to radially expand from a first position to a second position.

7. The system of claim 6, wherein the first expandable device comprises a self-expandable device and the second expandable device comprises a balloon-expandable device.

8. The system of claim 1, wherein the expandable device comprises an expanded outer diameter ranging from 2.0 mm to 5.0 mm.

9. The system of claim 1, wherein the expandable device comprises a length ranging from 7.0 mm to 40.0 mm.

10. The system of claim 1, wherein the expandable device comprises eight to thirty-eight wires.

11. The system of claim 10, wherein the at least eight to thirty-eight wires comprise at least two wires with a diameter between 0.0005" and 0.004".

12. The system of claim 11, wherein the at least two wires comprise wires with a diameter of approximately 0.003".

13. The system of claim 1, wherein the expandable device comprises a wire frame having a material selected from the group consisting of: metal; shape memory alloy; shape memory polymer; platinum; tungsten; cobalt chromium; and combinations thereof.

14. The system of claim 1, wherein the expandable device comprises a frame comprising at least two wires in a weave configuration.

15. The system of claim 14, wherein the weave configuration defines a diamond cell with a width less than or equal to 0.26 mm.

16. The system of claim 15, wherein the diamond cell width ranges from 0.053 mm to 0.15 mm.

17. The system of claim 16, wherein the diamond cell width approximates 0.13 mm.

18. The system of claim 1, wherein the first marker and the second marker are selected from the group consisting of: radiopaque markers that can be viewed with X-ray or fluoroscopy; visible markers that can be viewed with a visible intraluminal camera; infrared markers that can be viewed with an infrared intraluminal camera; ultrasound markers that can be viewed with external ultrasound or intravascular ultrasound; magnetic markers that can be viewed with MRI; and combinations thereof.

19. The system of claim 1, wherein the expandable device comprises at least one of: a polymer; a membrane comprising a polymer; or a polymer coating, wherein the polymer is selected from the group consisting of: a fluoropolymer; a polyimide; a silicone; a polyurethane; a polyurethane ether; a polyurethane ester; a polyurethane polycarbonate; a polyurethane urea; a biodegradable polylactide; a polyether; a polyethylene glycol (biostable); a poly(DL-lactide-co-caprolactone) (PLC); a poly(DL-lactide-co-glycolide) (PLGA); a polyester; a polycarbonate diol; a copolymer of these; or combinations thereof.

20. The system of claim 19, wherein the polymer comprises at least one chain extender selected from the group consisting of: methylene diisocyanate; toluene diisocyanate; hexamethylenediisocyanate; diisocyanates; alkyl-triols; triamines; orthoformic acid; phosphates; calcitriol; cyclic polyols; ciceritol; short chain functionalized amino acids; polyketides characterized by three hydroxyl groups; lipidoid C12-200; fluoroalkane; fluoroalkanols; and combinations thereof.

21. The system of claim 19, wherein the polymer comprises at least one end group wherein the at least one end group is functionalized prior to incorporation into the polymer.

22. The system of claim 19, wherein the polymer comprises a reactively functionalized polymer selected from the group consisting of: an allyl-alkyl hydroxide or amine; a siloxy-containing reactive functionality; a poly methyoxy or polyethyoxy low molecular weight complex; and combinations thereof.

23. The system of claim 1, wherein the expandable device comprises one or more radio-lucent or radio-opaque materials selected from the group consisting of: a halogen; a ceramic; a metal; a gel comprising a radio-lucent and/or radiopaque material; a gels-sol comprising a radio-lucent and/or radiopaque material; and combinations of these.

24. The system of claim 1, wherein at least a portion of the membrane comprises a biodegradable material.

25. The system of claim 1, wherein the expandable device comprises one or more agents selected from the group consisting of: a drug; a reagent; and combinations thereof.

26. The system of claim 25, wherein the polymer comprises a dendrimer-type polymer, the dendrimer-type polymer comprising dendrimers or dendrons.

27. The system of claim 25, wherein the one or more agents is selected from the group consisting of: anti-proliferative agents; anti-inflammatory agents; cell regeneration promoting agents; restenosis inhibiting agents; nanoparticles; drug-eluting nanoparticles; nanoparticle gels; and combinations thereof.

28. The system of claim 1, wherein the membrane comprises a thickness of 0.0005" to 0.005".

29. The system of claim 1, wherein the delivery device comprises a distal portion with a diametric profile between 0.045" to 0.060".

30. The system of claim 1, wherein the delivery device further comprises an inflatable element constructed and arranged to expand the expandable device from the first position to the second position.

31. The system of claim 1, further comprising a post-dilatation balloon constructed and arranged to eliminate a lumen between a vessel wall and the expandable device.

32. The system of claim 31, wherein the post-dilatation balloon is configured to expand a proximal portion of the expandable device prior to expanding a distal portion of the expandable device.

* * * * *